US007371207B2

(12) United States Patent
Jelinsky et al.

(10) Patent No.: US 7,371,207 B2
(45) Date of Patent: May 13, 2008

(54) ESTROGEN RECEPTOR α REGULATED GENE EXPRESSION, RELATED ASSAYS AND THERAPEUTICS

(75) Inventors: Scott Alan Jelinsky, Acton, MA (US); Heather Anne Harris, Phoenixville, PA (US); Eugene Lee Brown, Newton, MA (US); Mark James Evans, Radnor, PA (US); Donald Edward Frail, Wildwood, MO (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/511,064

(22) PCT Filed: Apr. 10, 2003

(86) PCT No.: PCT/US03/11240

§ 371 (c)(1),
(2), (4) Date: Apr. 20, 2005

(87) PCT Pub. No.: WO03/087336

PCT Pub. Date: Oct. 23, 2003

(65) Prior Publication Data

US 2005/0202432 A1 Sep. 15, 2005

Related U.S. Application Data

(60) Provisional application No. 60/371,682, filed on Apr. 12, 2002.

(51) Int. Cl.
*C40B 40/00* (2006.01)
(52) U.S. Cl. .......................... 506/13; 435/6; 536/23.1; 536/24.31; 536/23.5; 506/9
(58) Field of Classification Search ..................... None
See application file for complete search history.

(56) References Cited

U.S. PATENT DOCUMENTS 5,508,164 A 4/1996 Kausch
5,747,253 A * 5/1998 Ecker et al. .................. 435/6

OTHER PUBLICATIONS

Melia et al., Endocrinology 139(2):688-695 (1998).*
Chern et al., Nephron 85:258-266 (2000).*
Kuiper et al., Frontiers in Neuroendocrinology 19:253-286 (1998).*
Grodstein, F., Manson, J.E., Colditz, G A., Willett, W. C., Speizer, F. E. & Stampfer, M. J. (2000); A prospective, observational study of postmenopausal hormone therapy and primary prevention of cardiovascular disease. Annals of Internal Medicine 133, 933-41.
Barrett-Connor, E., Slone, S., Greendale, G., Kritz-Silverstein, D., Espeland, M., Johnson, S. R., Waclawiw, M. & Fineberg, S. E. (1997); The postmenopausal estrogen/progestin interventions study: primary outcomes in adherent women. Maturitas 27, 261-74.

Godsland, I. F. (2001); Effects of postmenopausal hormone replacement therapy on lipid, lipoprotein, and apolipoprotein (a) concentrations: analysis of studies published from 1974-2000. Fertility & Sterility 75, 898-915.
Nanda, K., Bastian, L. A., Hasselblad, V. & Simel, D. L. (1999); Hormone replacement therapy and the risk of colorectal cancer: a meta-analysis. Obstetrics & Gynecology 93, 880-8.
Kawas, C., Resnick, S., Morrison, A., Brookmeyer, R., Corrada, M., Zonderman, A., Bacal, C., Lingle, D. D. & Metter, E. (1997); A prospective study of estrogen replacement therapy and the risk of developing Alzheimer's disease: the Baltimore Longitudinal Study of Aging. Neurology 48, 1517-21.
Worzala, K., Hiller, R., Sperduto, R. D., Mutalik, K., Murabito, J. M., Moskowitz, M., D'Agostino, R. B. & Wilson, P. W. (2001); Postmenopausal estrogen use, type of menopause, and lens opacities: the Framingham studies. Archives of Internal Medicine 161, 1448-54.
Kuiper, & G, Carlsson, B., Grandien, K., Enmark, E., Haggblad, J., Nilsson, S. & Gustafsson, J. A. (1997) Endocrinology 138, 863-70.
Hill, A. A., Hunter, C. P., Tsung, B. T., Tucker-Kellogg, G & Brown, E. L. (2000); Genomic analysis of gene expression in *C. elegans*, Science 290, 809-12.
Shughrue, P., Scrimo, P., Lane, M., Askew, R. & Merchenthaler, I. (1997): The distribution of estrogen receptor-beta mRNA in forebrain regions of the estrogen receptor-alpha knockout mouse. Endocrinology 138, 5649-52.
Evans, M. J., Eckert, A., Lai, K., Adelman, S. J. & Hamish, D. C. (2001); Reciprocal antagonism between estrogen receptor and NF-kappaB activity in vivo. Circulation Research 89, 823-830.
Kraichely, D. M., Sun, J., Katzenellenbogen, J. A. & Katzenellenbogen, B. S. (2000); Conformational changes and coactivator recruitment by novel ligands for estrogen receptor-alpha and estrogen receptor-beta: correlations with biological character and distinct differences among SRC coactivator family members. Endocrinology 141, 3534-45.
Lubahn, D. B., Moyer, J. S., Golding, T. S., Couse, J. F., Korach, K. S. & Smithies, O. (1993); Alteration of reproductive function but not prenatal sexual development after insertional disruption of the mouse estrogen receptor gene. Proceedings of the National Academy of Sciences of the United States of America 90, 11162-6.

(Continued)

*Primary Examiner*—J. Douglas Schultz
*Assistant Examiner*—J. S. Lundgren
(74) *Attorney, Agent, or Firm*—Darby & Darby P.C.

(57) ABSTRACT

A plurality of genes modulated by estrogen or other agents, such as hormones or combinations of hormones, in various types of tissue is described. One embodiment of the disclosure relates to a plurality of genes, which demonstrates certain patterns of expression differing qualitatively or quantitatively, with and without exposure to estrogen and/or other hormone compositions. Methods of using these genes in identifying candidate agents that exert at least some of the biological effects of estrogen and/or other hormone, and pharmaceuticals and related therapies also is disclosed. The use of the plurality of genes in methods of monitoring, in gene chips and in kits also is disclosed.

5 Claims, 10 Drawing Sheets

OTHER PUBLICATIONS

Pendaries, C., Darblade, B., Rochaix, P., Krust, A., Chambon, P., Korach, K. S., Bayard, F. & Arnal, J. F. (2002); The AF-1 activation-function of ERalpha may be dispensable to mediate the effect of estradiol on endothelial NO production in mice. Proceedings of the National Academy of Sciences of the United States of America 99, 2205-2210.

Couse, J. F., Curtis, S. W., Washburn, T. F., Lindzey, J., Golding, T. S., Lubahn, D. B., Smithies, O. & Korach, K. S. (1995); Analysis of transcription and estrogen insensitivity in the female mouse after targeted disruption of the estrogen receptor gene. Molecular Endocrinology 9, 1441-54.

Berry, M., Metzger, D. & Chambon, R (1990); Role of the two activating domains of the oestrogen receptor in the cell-type and promoter-context dependent agonistic activity of the anti-oestrogen 4-hydroxytamoxifen. EMBO Journal 9, 2811-8.

Hall, J. M. & McDonnell, D. P. (1999); The estrogen receptor beta-isoform (ERbeta) of the human estrogen receptor modulates ERalpha transcriptional activity and is a key regulator of the cellular response to estrogens and antiestrogens. Endocrinology 140, 5566-78.

Weihua, Z., Saji, S., Makinen, S., Cheng, G., Jensen, E. V., Waamer, M. & Gustafsson, J. A. (2000); Estrogen receptor (ER) beta, a modulator of ERalpha in the uterus. Proceedings of the National Academy of Sciences of the United States of America 97, 5936-41.

Trogan, E., Choudhury, R. P., Dansky, H. M., Rong, J. X., Breslow, J. L. & Fisher, E. A. (2002); Laser capture microdissection analysis of gene expression in macrophages from atherosclerotic lesions of apolipoprotein E-deficient mice. Proceedings of the National Academy of Sciences of the United States of America 99, 2234-2239.

Evans, M. J., Lai, K., Shaw, L. J., Harnish, D. C. & Chadwick, C. C. (2002); Estrogen receptor alpha inhibits IL-1beta induction of gene expression in the mouse liver. Endocrinology, 143(7):2559-70.

McIntire, J. J., Umetsu, S. E., Akbari, O., Potter, M., Kuchroo, V. K., Barsh, G. S., Freeman, Q J., Umetsu, D. T. & DeKruyff, R. H. (2001); Identification of Tapr (an airway hyperreactivity regulatory locus) and the linked Tim gene family. Nature Immunology 2, 1109-16.

Ichimura, T., Bonventre, J. V., Bailly, V., Wei, H., Hession, C. A., Cate, R. L. & Sanicola, M. (1998): Kidney injury molecule-1 (KIM-1), a putative epithelial cell adhesion molecule containing a novel immunoglobulin domain, is up-regulated in renal cells after injury. Journal of Biological Chemistry 273, 4135-42.

Davidoff, M., Caffier, H. & Schiebler, T. H. (1980); Steroid hormone binding receptors in the rat kidney. Histochemistry 69, 39-48.

Aitken, J. M., Lindsay, R. & Hart, D. M. (1974); The redistribution of body sodium in women on long-term oestrogen therapy. Clinical Science-& Molecular Medicine 47, 179-87.

Pirani, B. B., Campbell, D. M. & MacGillivray, I. (1973); Plasma volume in normal first pregnancy. Journal of Obstetrics & Gynaecology of the British Commonwealth 80, 884-7.

Stachenfeld, N. S., DiPietro, L., Palter, S. F. & Nadel, E. R. (1998); Estrogen influences osmotic secretion of AVP and body water balance in postmenopausal women. American Journal of Physiology 274, R187-95.

Verlander, J. W., Tran, T M., Zhang, L., Kaplan, M. R. & Hebert, S. C. (1998); Estradiol enhances thiazide-sensitive NaCl cotransporter density in the apical plasma membrane of the distal convoluted tubule in ovariectomized rats. Journal of Clinical Investigation 101, 1661-9.

Farmer, M. K., Robbins, M. J., Medhurst, A. D., Campbell, D. A., Ellington, K., Duckworth, M., Brown, A. M., Middlemiss, D. N., Price, G. W. & Pangalos, M. N. (2000); Cloning and characterization of human NTT5 and v7-3: two orphan transporters of the Na+/Cl—dependent neurotransmitter transporter gene family. Genomics 70, 241-52.

Reddy, M. M., Light, M. J. & Quinton, P. M. (1999); Activation of the epithelial Na+ channel (ENaC) requires CFTR Cl− channel function. Nature 402, 301-4.

Fu, G. K., Lin, D., Zhang, M. Y., Bikle, D. D., Shackleton, C. H., Miller, W. L. & Portale, A. A. (1997); Cloning of human 25-hydroxyvitamin D-1 alpha-hydroxylase and mutations causing vitamin D-dependent rickets type 1. Molecular Endocrinology 11, 1961-70.

Tanaka, Y., Castillo, L. & DeLuca, H. F. (1976); Control of renal vitamin D hydroxylases in birds by sex hormones. Proceedings of the National Academy of Sciences of the United States of America 73, 2701-5.

McKane, W. R., Khosla, S., Burritt, M. F., Kao, P. C., Wilson, D. M., Ory, S. J. & Riggs, B. L. (1995); Mechanism of renal calcium conservation with estrogen replacement therapy in women in early postmenopause—a clinical research center study. Journal of Clinical Endocrinology & Metabolism 80, 3458-64.

Grey, A. B., Stapleton, J. P., Evans, M. C., Tatnell, M. A. & Reid, I. R. (1996); Effect of hormone replacement therapy on bone mineral density in postmenopausal women with mild primary hyperparathyroidism. A randomized, controlled trial. Annals of Internal Medicine 125, 360-8.

Johnson, J. A. & Kumar, R. (1994); Renal and intestinal calcium transport: roles of vitamin D and vitamin D-dependent calcium binding proteins. Seminars in Nephrology 14, 119-28.

Hajjar, K. A. (2001); Homocysteine: a sulph'rous fire. Journal of Clinical Investigation 107, 663-4.

Bostom, A. G., Silbershatz, H., Rosenberg, I. H., Selhub, J., D'Agostino, R. B., Wolf, P. A., Jacques, P. F. & Wilson, P W. (1999); Nonfasting plasma total homocysteine levels and all-cause and cardiovascular disease mortality in elderly Framingham men and women. Archives of Internal Medicine 159, 1077-80.

Walsh, B. W., Paul, S., Wild, R. A., Dean, R. A., Tracy, R. P., Cox, D. A. & Anderson, P. W. (2000); The effects of hormone replacement therapy and raloxifene on C-reactive protein and homocysteine in healthy postmenopausal women: a randomized, controlled trial. Journal of Clinical Endocrinology & Metabolism 85, 214-8.

Libert, F., Parmentier, M., Lefort, A., Dumont, J. E. & Vassart, G (1990); Complete nucleotide sequence of a putative G protein coupled receptor: RDC1. Nucleic Acids Research 18, 1917.

Kapas, S. & Clark, A. J. (1995); Identification of an orphan receptor gene as a type 1 calcitonin gene-related peptide receptor. Biochemical & Biophysical Research Communications 217, 832-8.

Gangula, P. R., Zhao, H., Wimalawansa, S. J., Supowit, S. C., DiPette, D. J. & Yallampalli, C. (2001); Pregnancy and steroid hormones enhance the systemic and regional hemodynamic effects of calcitonin gene-related peptide in rats. Biology of Reproduction 64, 1776-83.

Cadnapaphomchai, M. A., Briner, V. A. & Schrier, R. W. (2001) in Diseases of the Kidney and Urinary Tract, ed. Schrier, R. W. (Lippincott Williams & Wilkins, Philadelphia), pp. 1459-1487.

Safe, S. (2001); Transcriptional activation of genes by 17 beta-estradiol through estrogen receptor-Sp1 interactions. Vitamins & Hormones 62, 231-52.

Paech, K., Webb, P., Kuiper, G. G., Nilsson, S., Gustafsson, J., Kushner, P. J. & Scanlan, T. S. (1997); Differential ligand activation of estrogen receptors ERalpha and ERbeta at AP1 sites. Science 277, 1508-10.

Naka, T., Fujimoto, M. & Kishimoto, T. (1999); Negative regulation of cytokine signaling: STAT-induced STAT inhibitor. Trends in Biochemical Sciences 24, 394-8.

Melia, M.J., Bofill, N., Hubank, M., Meseguer A. (1998); Identification of Androgen-Regulated Genes in Mouse Kidney by Representational difference Analysis and Random Arbitrarily Primed Polymerase Chain Reaction. Endocrinology, 139:688-695.

Chern, T.H., Chiang, F-T., Wu, K-D, Hsu, K-L, Lo, H-M, Tseng, C-D., and Tseng, Y-Z. (2000); Expression Pattern in a Modified Equalized Kidney cDNA Library of Hypertensive Rat. Nephron, 85:258-266.

WO/03/087336 Search Report.

\* cited by examiner

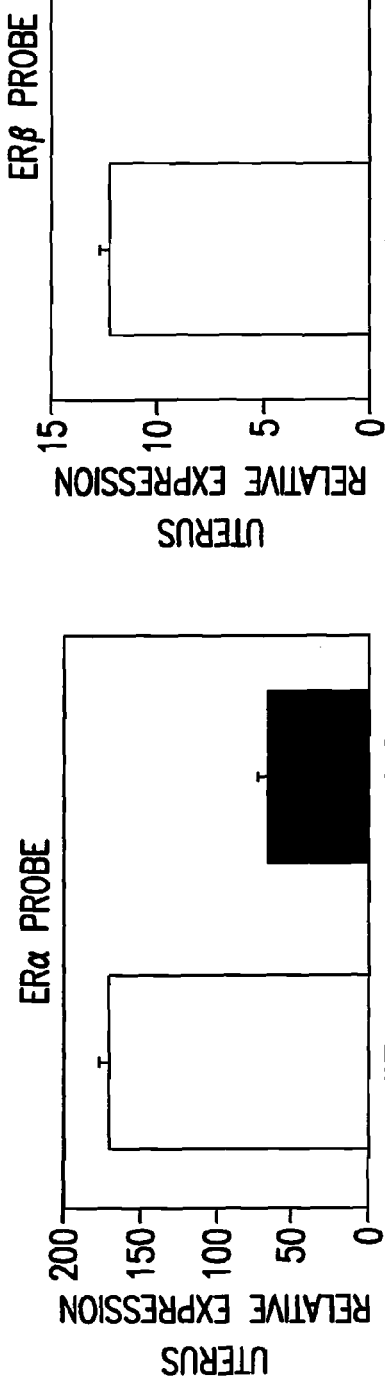
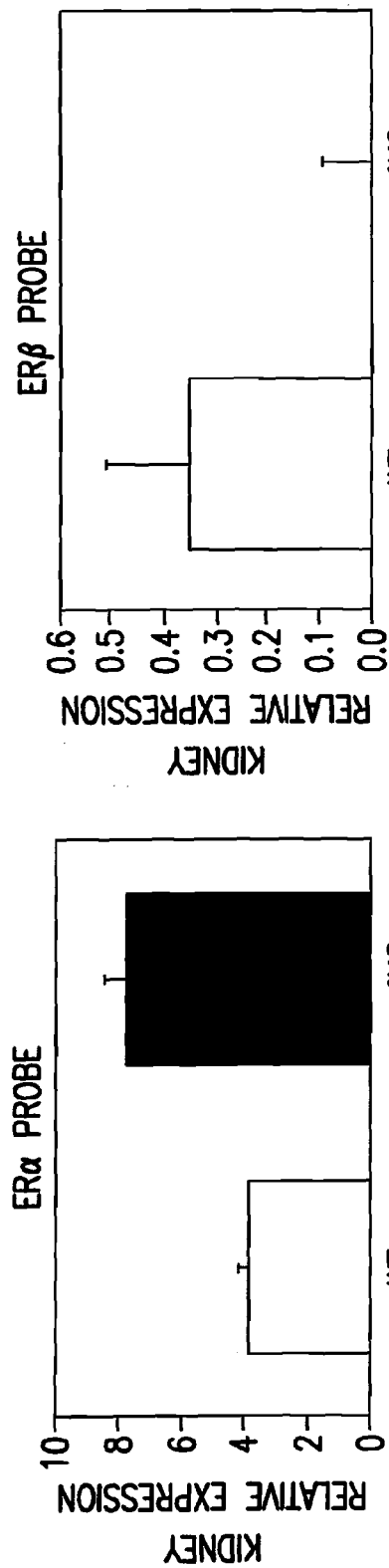
FIG. 7A  FIG. 7B  FIG. 7C  FIG. 7D

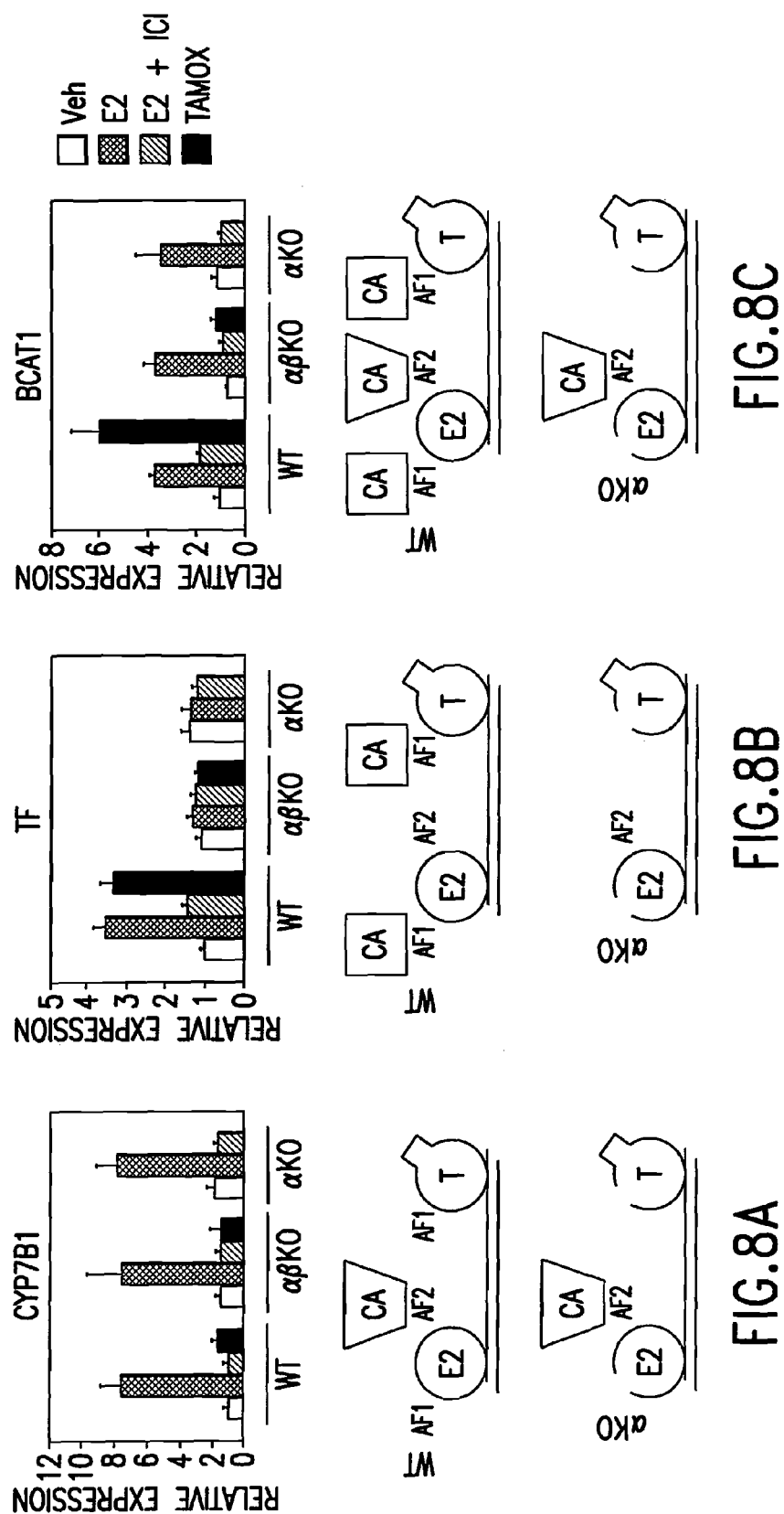

ESTROGEN RECEPTOR α REGULATED GENE EXPRESSION, RELATED ASSAYS AND THERAPEUTICS

CROSS-REFERENCE TO RELATED APPLICATIONS

This application is a U.S. National Stage Application under 35 U.S.C. §371 of International Patent Application No. PCT/US03/11240, filed Apr. 10, 2003, which claims priority to U.S. Patent Application No. 60/371,682, filed Apr. 12, 2002.

FIELD OF THE INVENTION

The present disclosure relates to a plurality of genes modulated by estrogen or other agents, such as hormones or combinations of hormones, in various types of tissue. In particular, one embodiment of the disclosure relates to a plurality of genes which demonstrates certain patterns of expression differing qualitatively or, quantitatively, with and without exposure to estrogen and/or other hormone compositions. The disclosure further relates to the methods of using these genes in identifying agents that exert at least some of the biological effects of estrogen and/or other agents, and to pharmaceuticals and related therapies. The disclosure further relates to the use of the plurality of genes in methods of monitoring, in gene chips and in kits.

BACKGROUND OF THE INVENTION

Estrogens exert biological effects in numerous organs throughout the body. The role of estrogens in reproductive biology, the prevention of postmenopausal hot flashes, and the prevention of postmenopausal osteoporosis are well established. Many observational studies have suggested estrogens also reduce the risk of development of cardiovascular disease(1), at least in part by estrogens reducing LDL cholesterol levels and elevating HDL cholesterol levels(2,3). More recently, estrogens have been suggested to inhibit the development of colon cancer(4), inhibit the development of Alzheimer's disease(5), and inhibit development of cataracts (6). The multitude of estrogen responses matches the widespread distribution of estrogen receptors (ER) throughout numerous organs, with ERα expression highest in uterus, pituitary, kidney and adrenal gland and ERβ expression highest in ovary, uterus, bladder and lung(7). While various estrogens have been profiled for biological activity, little is known regarding the patterns of gene expression which are responsible for these diverse activities.

Thus, a need exists for the systemic analysis of the regulation by estrogen and/or other hormonal compositions of gene expression in various tissues and the identification of the plurality of differentially expressed genes. The identification of candidate agents that at least partially exert the same differential expression and development of pharmaceuticals and new treatment methods based on such agents is highly desirable. There also exists a need for methods of monitoring conditions and for diagnostic products, including gene chips and kits, which may be used in the above-described analyses.

The embodiments provided herein relate generally to a plurality of genes, particularly a plurality of genes that are modulated by estrogen and/or other hormonal compositions in various organs, such as the uterus, kidney and pituitary gland. Such differentially expressed genes are useful in screening assays to examine the effects of a candidate agent on the expression of genes that are responsive to estrogen. A candidate agent that induces, in a given tissue, a gene expression profile that exhibits one or more similarities to the gene expression profile of estrogen and/or other hormonal compositions, can be identified for possible use in pharmaceuticals. The invention also relates to the identification of estrogen responsive genes that are known to be associated with the inhibition of certain conditions, such as shock, post-menopausal calcium deficiencies, cardiovascular diseases, and conditions where there is decreased renal blood flow, such as those caused by diuretics or congestive heart failure.

BRIEF DESCRIPTION OF THE DRAWINGS

FIGS. 7A-7D show bar graphs depicting expression levels of intact and ΔAF1-ERα mRNA determined in uterus and kidney by using a real-time PCR assay specific for exon 3 of the mouse ERα or ERβ genes. Each graph utilizes a different scale. Expression levels were normalized for total RNA level to avoid GAPDH expression differences between kidney and uterus.

FIGS. 8A-8C show a series of relative expression levels for various genes in different types of mice. This figure also presents a model for AF1 or AF2 activation for each gene. Ovariectomized WT mice, ERαERβKO mice (expressing only ΔAF1-ERα) or ERαKO mice (expressing ΔAF1-ERα along with ERβ) were treated for 6 weeks with vehicle, 10 µg/kg/day E2, 10 µg/kg/day E2+5 mg/kg/day ICI182780, or 5 mg/kg/day tamoxifen. Kidney gene expression values were determined by real-time PCR for each individual animal and normalized for GAPDH expression. The mean expression level in vehicle-treated WT mice was defined as 1 for each gene. *p<0.01 for comparison to vehicle treated animals. A model for the requirement of AF1 or AF2 for activation of each gene is shown below each graph. The change in ER shape with tamoxifen (T) bound denotes the alternate helix 12 conformation induced by tamoxifen compared to E2. CA denotes coactivators.

SUMMARY OF EMBODIMENTS

Figure 1:
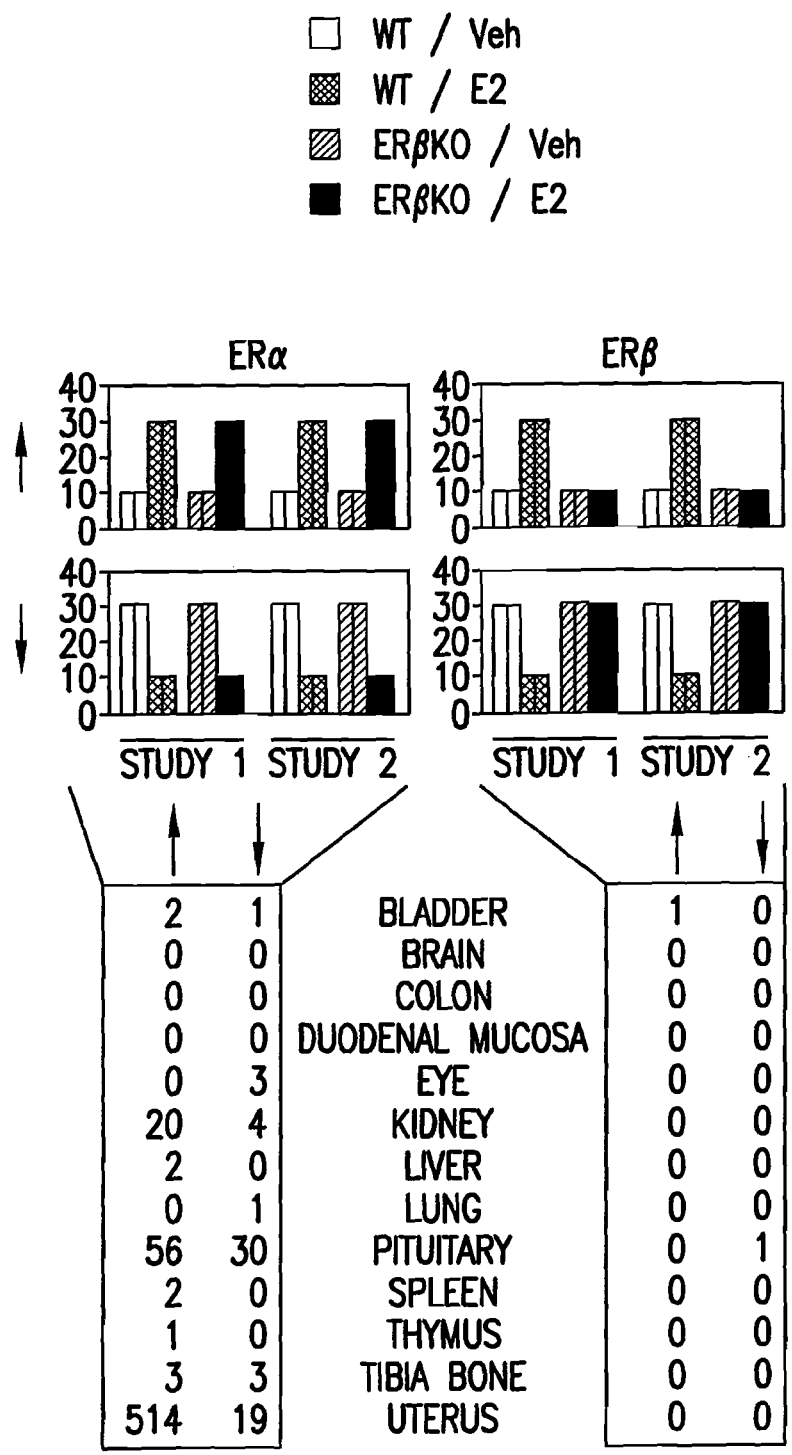
FIG. 1 depicts a pattern analysis generated by a GeneChip microarray analysis. Specifically, WT or ERβKO ovariectomized mice were treated daily with vehicle or 20 µg/kg/day E2 for six weeks. Two hours following the final dose, the mice were euthanized and 13 tissues removed for RNA preparation. Two independent studies were performed, with total RNA pooled from two groups of three animals for each condition. Gene expression was quantified by GeneChip microarrays using murine U74 sub A arrays. Data were analyzed for patterns indicating either ERα or ERβ dependent regulation as shown. For ERα regulation, the defined search patterns (induction or repression) were for regulation by E2 in both wild type and ERβKO mice, in both sets of mice in both studies. For ERβ regulation, the defined search patterns were for regulation by E2 only in the wild type mice, with no change in basal expression in the ERβKO mice compared to the wild type mice. The number of genes in each tissue that matched the theoretical induction (↑) or repression (↓) patterns for ERα or ERβ are indicated.

One embodiment of the disclosure relates to a plurality of genes, each of whom is differentially expressed in tissue cells exposed to estrogen and/or other hormones or combination of hormones and tissue cells without said exposure, which plurality comprises a first group and a second group, wherein each gene in said first group is differentially expressed at a higher level in said tissue cells exposed to estrogen and/or a hormone or combinations of hormones than in said tissue cells without said exposure, wherein each gene in said second group is differentially expressed at a lower level in said tissue cells exposed to estrogen and/or a hormone or combinations of hormones than in said tissue cells without said exposure. Confirmation of such expression is confirmed by real-time PCR. Such cells preferably are from the kidney, pituitary or uterus. Exposure to estrogen and/or the other hormones is in vivo or in vitro. The higher level and lower levels are assessed using a predetermined statistical significance standard based on measurements of expression levels. The measurements can obtained using nucleotide arrays or nucleotide filters.

Another embodiment relates to a method for identifying an agent having the biological effect of estrogen and/or other hormones or combination of hormones, on gene expression in a given tissue, wherein said desired effect represents a first plurality of genes differentially expressed at various levels, which method comprises:
exposing, in vivo or in vitro, tissue cells to said agent;
measuring expression levels of a multiplicity of genes in said tissue cells exposed to said agent and tissue cells without said exposure, said multiplicity being greater than said first plurality;
determining, using a predetermined statistical significance standard, genes which are differentially expressed in said tissue cells exposed to said agent and said tissue cells without said exposure, said genes constitute a second plurality; and
comparing the expression levels of genes in said second plurality with the expression levels of genes in said first plurality, wherein said agent is identified as having said desired effort if said first and second pluralities are the same and said expression levels in said first and second pluralities are substantially the same. The tissue preferably is kidney, uterus or pituitary tissue. Expression levels are confirmed by real-time PCR.

Another embodiment is directed to an agent identified by the above method.

Another embodiment is a pharmaceutical composition comprising this agent and a pharmaceutically acceptable excipient.

Another embodiment relates to a method for identifying an agent capable of maintaining vascular volume in septic shock, which method comprises:
exposing, in vivo or in vitro, kidney cells to the agent;
measuring expression levels of NTT73 and ABCC3 in said kidney cells exposed to the agent and kidney cells without the exposure;
comparing the expression levels of NTT73 and ABCC3 with the expression levels of genes in the plurality if genes described above with regard to the kidney, wherein the induced genes are NTT73 and ABCC3, wherein said agent is identified as capable of maintaining vascular volume in septic shock if said expression levels of NTT73 and ABCC3 are substantially the same as said expression levels of genes in such plurality.

Another embodiment relates to a method of identifying an agent capable of enhancing calcium uptake in post-menopausal women, which method comprises:
exposing, in vivo or in vitro, kidney cells to said agent;
measuring expression levels of CYP7B1 in said kidney cells exposed to said agent and kidney cells without said exposure;
comparing the expression levels of CYP7B1 with the expression levels of genes in the plurality of genes in the kidney is induced CYP7B1, wherein said agent is identified as capable of enhancing calcium uptake in post-menopausal women if said expression levels of CYP7B1 are substantially the same as said expression levels of genes in such plurality.

Another embodiment relates to a method for identifying an agent for treating cardiovascular disorders, which method comprises:
exposing, in vivo or in vitro, kidney cells to said agent;
measuring expression levels of BHMT and SAHH in said kidney cells exposed to said agent and kidney cells without said exposure;
comparing the expression levels of BHMT and SAHH with the expression levels of genes in the plurality of genes, wherein in the kidney BHMT and SAHH are repressed, wherein said agent is identified for treating cardiovascular disorders if said expression levels of BHMT and SAHH are substantially the same as said expression levels of genes in the such plurality.

Another embodiment relates to agents identified by any of the above methods and pharmaceutical agents comprising such agents and a pharmaceutically acceptable excipient.

Another embodiment relates to a solid substrate comprising any of the above described plurality of genes.

Another embodiment relates to a kit comprising any of the above plurality of genes.

DETAILED DESCRIPTION OF THE PREFERRED EMBODIMENTS

The embodiments herein provide a plurality of genes modulated by estrogen and/or other hormonal compositions of interest in various types of tissue and the use of such a plurality of differentially expressed genes in screening for agents that exert at least some of the biological effects of estrogen and other hormonal compositions of interest. Such identified agents can be used in pharmaceuticals and in related new therapeutic methods. The plurality of genes can be used in methods of monitoring.

Definitions:

In general, "a gene" is a region on the genome that is capable of being transcribed to an RNA that either has a regulatory function, a catalytic function and/or encodes a protein. A gene typically has introns and exons, which may organize to produce different RNA splice variants that encode alternative versions of a mature protein. "Gene" contemplates fragments of genes that may or may not represent a functional domain.

A "plurality of genes" as used herein refers to a group of identified or isolated genes whose levels of expression vary in different tissues, cells or under different conditions or biological states. The different conditions may be caused by exposure to certain agent(s)—whether exogenous or endogenous—which include hormones, receptor ligands, chemical compounds, etc. The expression of a plurality of genes demonstrates certain patterns. That is, each gene in the plurality is expressed differently in different conditions or with or without exposure to a certain endogenous or exogenous agents. The extent or level of differential expression of each gene may vary in the plurality and may be determined qualitatively and/or quantitatively according to this invention. A gene expression profile, as used herein, refers to a plurality of genes that are differentially expressed at different levels, which constitutes a "pattern" or a "profile." As used herein, the term "expression profile," "profile," "expression pattern," "pattern," "gene expression profile," and "gene expression pattern" are used interchangeably.

An "agent that exerts at least some of the biological effects of estrogen," as used herein refers to any factor, agent, compound whether endogenous or exogenous in origin, which is capable of binding and interacting with estrogen receptors and thereby eliciting certain biological effects of extrogen. The skilled artisan would know that, for instance, one of the biological effects of estrogen is to promote the development of the female reproductive system. Other biological effects of estrogen are well documented and discussed, infra.

Gene expression profiles may be measured, according to this invention, by using nucleotide or microarrays. These arrays allow tens of thousands of genes to be surveyed at the same time.

"Hormones or combinations of hormones" include for instance, combinations of estrogens or other hormones that are known to exert biological effects of estrogen.

As used herein, the term "microarray" refers to nucleotide arrays that can be used to detect biomolecules, for instance to measure gene expression. "Array," "slide," and "chip" are used interchangeably in this disclosure. Various kinds of arrays are made in research and manufacturing facilities worldwide, some of which are available commercially. There are, for example, two main kinds of nucleotide arrays that differ in the manner in which the nucleic acid materials are placed onto the array substrate: spotted arrays and in situ synthesized arrays. One of the most widely used oligonucleotide arrays is GeneChip™ made by Affymetrix, Inc. The oligonucleotide probes that are 20- or 25-base long are synthesized in silico on the array substrate. These arrays tend to achieve high densities (e.g., more than 40,000 genes per $cm^2$). The spotted arrays, on the other hand, tend to have lower densities, but the probes, typically partial cDNA molecules, usually are much longer than 20- or 25-mers. A representative type of spotted cDNA array is LifeArray made by Incyte Genomics. Pre-synthesized and amplified cDNA sequences are attached to the substrate of these kinds of arrays.

In one embodiment, the nucleotide is an array (i.e., a matrix) in which each position represents a discrete binding site for a product encoded by a gene (e.g., a protein or RNA), and in which binding sites are present for products of most or almost all of the genes in the organism's genome. In one embodiment, the "binding site" (hereinafter, "site") is a nucleic acid or nucleic acid analogue to which a particular cognate cDNA can specifically hybridize. The nucleic acid or analogue of the binding site can be, e.g., a synthetic oligomer, a full-length cDNA, a less-than full length cDNA, or a gene fragment.

Although the microarray may contain binding sites for products of all or almost all genes in the target organism's genome, such comprehensiveness is not necessarily required. Usually the microarray will have binding sites corresponding to at least about 50% of the genes in the genome, often at least about 75%, more often at least about 85%, even more often more than about 90%, and most often at least about 99%. Preferably, the microarray has binding sites for genes relevant to the action of the gene expression modulating agent of interest or in a biological pathway of interest.

The nucleic acid or analogue are attached to a "solid support," which may be made from glass, plastic (e.g., polypropylene, nylon), polyacrylamide, nitrocellulose, or other materials. A preferred method for attaching the nucleic acids to a surface is by printing on glass plates, as is described generally by Schena et al., 1995, Quantitative monitoring of gene expression patterns with a complementary DNA microarray, Science 270:467-470. This method is especially useful for preparing microarrays of cDNA. See also DeRisi et al., 1996, Use of a cDNA microarray to analyze gene expression patterns in human cancer, Nature Genetics 14:457-460; Shalon et al., 1996, A DNA microarray system for analyzing complex DNA samples using two-color fluorescent probe hybridization, Genome Res. 6:639-645; and Schena et al., 1995, Parallel human genome analysis; microarray-based expression of 1000 genes, Proc. Natl. Acad. Sci. USA 93:10539-11286.

In a preferred embodiment, the microarray is a high-density oligonucleotide array, as described above. In a particularly preferred embodiment, the nucleotide arrays are the MG_U74 and MG_U74v2 arrays from Affymetrix.

"Polymerase Chain Reaction" or "PCR" is an amplification-based assay used to measure the copy number of the gene. In such assays, the corresponding nucleic acid sequences act as a template in an amplification reaction. In a quantitative amplification, the amount of amplification product will be proportional to the amount of template in the original sample. Comparison to appropriate controls provides a measure of the copy number of the gene, corresponding to the specific probe used, according to the principle discussed above. Methods of "real-time quantitative PCR" using Taqman probes are well known in the art. Detailed protocols for real-time quantitative PCR are provided, for example, for RNA in: Gibson et al., 1996, A novel method for real time quantitative RT-PCR. *Genome Res.* 10:995-1001; and for DNA in: Heid et al., 1996, Real time quantitative PCR. *Genome Res.* 10:986-994.

A TaqMan-based assay can also be used to quantify polynucleotides. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, for example, AmpliTaq, results in the cleavage of the TaqMan probe. This cleavage separates the 5' fluorescent dye and the 3' quenching agent, thereby resulting in an increase in fluorescence as a function of amplification (see, for example, http://www2.perkin-elmer.com).

Other suitable amplification methods include, but are not limited to, ligase chain reaction (LCR) (see, Wu and Wallace, 1989, *Genomics* 4: 560; Landegren et al., 1988 *Science* 241: 1077; and Barringer et al., 1990, *Gene* 89: 117), transcription amplification (Kwoh et al., 1989, *Proc. Natl. Acad. Sci. USA* 86: 1173), self-sustained sequence replication (Guatelli et al., 1990, *Proc. Nat. Acad. Sci. USA* 87: 1874), dot PCR, and linker adapter PCR, etc.

The "level of mRNA" in a biological sample refers to the amount of mRNA transcribed from a given gene that is present in a cell or a biological sample. One aspect of the biological state of a biological sample (e.g. a cell or cell culture) usefully measured in the present invention is its transcriptional state. The transcriptional state of a biological sample includes the identities and abundances of the constituent RNA species, especially mRNAs, in the cell under a given set of conditions. Preferably, a substantial fraction of all constituent RNA species in the biological sample are measured, but at least a sufficient fraction is measured to characterize the action of an agent or gene modulator of interest. The level of mRNA may be quantified by methods described herein or may be simply detected, by visual detection by a human, with or without comparison to a level from a control sample or a level expected of a control sample.

A "biological sample," as used herein refers to any sample taken from a biological subject, in vivo or in situ. A biological sample may be a sample of biological tissue, or cells or a biological fluid. Biological samples may be taken, according to this invention, from any kind of biological species, any types of tissues, and any types of cells, among other things. Cell samples may be isolated cells, primary cell cultures, or cultured cell lines according to this invention. Biological samples may be combined or pooled as needed in various embodimets. Preferred tissues are from the uterus, kidney, pituitary glands, breast, brain and adipose tissue.

"Modulation of gene expression," as this term is used herein, refers to the induction or inhibition of expression of a gene. Such modulation may be assessed or measured by assays. Typically, modulation of gene expression may be caused by endogenous or exogenous factors or agents. The effect of a given compound can be measured by any means known to those skilled in the art. For example, expression levels may be measured by PCR, Northern blotting, Primer Extension, Differential Display techniques, etc.

"Induction of expression" as used herein refers to any observable or measurable increase in the levels of expression of a particular gene, either qualitatively or quantitatively. The measurement of levels of expression may be carried out according to this invention using any techniques that are capable of measuring RNA transcripts in a biological sample. Examples of these techniques include, as discussed above, PCR, TaqMan, Primer Extension, Differential display and nucleotide arrays, among other things.

"Repression of expression." "Repression" or "inhibition" of expression, are used interchangeably according to this disclosure. It refers to any observable or measurable decrease in the levels of expression of a particular gene, either qualitatively or quantitatively. The measurement of levels of expression may be carried out using any techniques that are capable of measuring RNA transcripts in a biological sample. The examples of these techniques include, as discussed above, PCR, TaqMan, Primer Extension, Differential Display, and nucleotide arrays, among other things."

A "gene chip" or "DNA chip" is described, for instance, in U.S. Pat. Nos. 5,412,087, 5,445,934 and 5,744,305 and is useful for screening gene expression at the mRNA level. Gene chips are commercially available.

A "kit" is one or more of containers or packages, containing at least one "plurality of genes," as described above, on a solid support. Such kit also may contain various reagents or solutions, as well as instructions for use and labels.

A "detectable label" or a "detectable moiety" is a composition that when linked with a nucleic acid or a protein molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes, biotin, digoxigenenin or haptens. A "labeled nucleic acid or oligonucleotide probe" is one that is bound, either covalently, through a linker or a chemical bond, or noncovalently through ionic, vander Waals, electrostatic, hydrophobic interactions, or hydrogen bonds, to a label such that the presence of the nucleic acid or probe may be detected by detecting the presence of the label bound to the nucleic acid or probe.

A "nucleic acid probe" is a nucleic acid capable of binding to a target nucleic acid or complementary sequence through one or more types of chemical bond, usually through complementary base pairing usually through hydrogen bond formation. As used herein, a probe may include natural (i.e., A, G, C, or T or modified bases (7-deazaguanosine, inosine, etc.). In addition, the bases in a probe may be joined by a linkage other than a phosphodiester bond, so long as it does not interfere with hybridization. It will be understood by one of skill in the art that probes may bind target sequences that lack complete complementarity with the probe sequence depending upon the stringency of the hybridization conditions. The probes are preferably directly labeled with isotopes, for example, chromophores, luminphores, chromogens, or indirectly labeled with biotin to which a strepavidin complex may later bind. By assaying the presence or absence of the probe, one can detect the presence or absence of a target gene of interest.

"In situ hybridization" is a methodology for determining the presence of or the copy number of a gene in a sample, for example, fluorescence in situ hybridization (FISH) (see Angerer, 1987 *Meth. Enzymol* 152: 649). Generally, in situ hybridization comprises the following major steps: (1) fixation of tissue or biological structure to be analyzed; (2)

prehybridization treatment of the biological structure to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions.

Hybridization protocols suitable for use with the methods of the invention are described, for example, in Albertson (1984) *EMBO J.* 3:1227-1234; Pinkel (1988) *Proc. Natl. Acad. Sci. USA* 85:9138-9142; EPO Pub. No. 430:402; *Methods in Molecular Biology*, Vol. 33: In Situ Hybridization Protocols, Choo, ed., Humana Press, Totowa, N.J. (1994); etc.

"A predetermined statistical significance standard based on measurements of expression levels" is a confidence score based upon the assessment of four factors. Specifically, a score is assigned to each gene that reflects the confidence of the change. The score is based on four criteria: Fold Change, p-value (T-test), Present Calls, Frequency Value. For example, see the Table below:

TABLE I

Confidence criteria

| | Score |
|---|---|
| Fold Change | |
| >2.0 | 5 |
| >1.5 | 0 |
| <1.5 | −3 |
| pValue | |
| <0.05 | 3 |
| 0.05 to 0.1 | 2 |
| 0.1 to 0.2 | 0 |
| 0.2 to 0.3 | −1 |
| 0.3 to 0.5 | −3 |
| Present Calls | |
| 2-4 | 3 |
| 1 | 1 |
| 0 | 0 |
| Second Largest Frequency | |
| >20 | 3 |
| 15 to 191 | |
| 10-14 | −1 |
| <10 | −3 |
| Outliers (Max Freq/$2^{nd}$ largest) | |
| >2.5 | −3 |

"Data" refers to information obtained that relates to the expression of genes in response to exposure to estrogen or an agent of unknown biological effect. The plurality of genes identified by the disclosed methods are examples of such information. The information is stored in electronic or paper formats. Electronic format can be selected from the group consisting of electronic mail, disk, compact disk (CD) digital versatile disk (DVD), memory card, memory chip, ROM or RAM, magnetic optical disk, tape, video, video clip, microfilm, internet, shared network, shared server and the like; wherein data is displayed, transmitted or analyzed via electronic transmission, video display, telecommunication, or by using any of the above stored formats; wherein data is compared and compiled at the site of sampling specimens or at a location where the data is transported following a process as described above.

"Genes modulated by estrogen." Genes regulated by estrogen and/or hormonal compositions and identified according to the disclosed methods, are listed in Tables II, III and IV. Relevant Unigene codes or Genbank accession numbers are provided.

Identification of Genes Modulated by Estrogen

A. Biological Sample and Assay

One embodiment disclosed herein relates to a plurality of genes, each of which is differentially expressed in kidney cells exposed to estrogen or a candidate agent and kidney cells without exposure to estrogen or a candidate agent, which plurality comprises a first group and a second group, wherein each gene in said first group is differentially expressed at a higher level in said kidney cells exposed to estrogen or a candidate agent than in said kidney cells without said exposure, wherein each gene in the second group is differentially expressed at a lower level in said kidney cells exposed to estrogen or candidate agent than in said kidney cells without said exposure.

A biological sample of kidney cells are obtained according to methods well known to the skilled artisan. One group of kidney cells are exposed to estrogen. Such estrogen may be 17β estradiol. The kidney cells may be from one or more animals of the same species or from a culture of kidney cells or kidney tissue. Preferably, such cells are from a mammal, most preferably a mouse, rat or human. Such animal must produce little or no estrogen. For instance, an aromatase knockout animal cannot produce estrogen. Because the major source of circulating estrogen is the ovary, ovariectomy dramatically decreases circulating estrogen levels. Thus, in one embodiment, ovariectomized animals are used. By "exposure" is meant a type and quantity of either in vivo or in vitro administration that is applicable to the source of the kidney cells and known and acceptable to those of skill of the art. The total RNA from such cells is prepared by methods known to the skilled artisan, e.g., by Trizol (Invitrogen) followed by subsequent repurification, e.g. via Rneasy columns (Qiagen). The total RNA is used to generate a labeled target according to methods and using detectable labels well know in the art, as described above in detail. For instance, the RNA may be labeled with biotin to form a cRNA target for use in an assay. See a complete description of preferred methods in the Affymetrix GeneChip® technical manual (Pages 700217 through 700223), which is herein incorporated by reference.

The assay, according to the invention, may be any assay suitable to detect gene expression. For instance, mRNA, cDNA or protein expression may be detected. Many different types of assays are known, examples of which are set forth above, including analyses by nucleotide arrays and nucleotide filters. The hybridization conditions (temperature, time, and concentrations) are adjusted according to procedures also well known in the art, as described above. In a preferred embodiment, the assay of the invention involves the use of a high density oligonucleotide array. For instance, in a preferred embodiment, cRNA labeled with biotin is hybridized to a murine MG_U74Av2 probe array (Affymetrix, Santa Clara, Calif.) for 16 hours at 45 degrees. Eleven biotin-labeled cRNAs at defined concentration are spiked into each hybridization and used to convert average difference values to frequencies expressed as parts per million.

Other solid supports and microarrays are known and commercially available to the skilled artisan, as described above.

B. Measurements and Statistical Analysis

The assay of the invention is used to identify genes modulated by estrogen. Such modulation may be induction of expression (a plurality of genes belonging to a "first group") or repression of such expression (a plurality of genes belonging to a "second group"). Gene expression induction is indicated by a higher level of expression, whereas repression is indicated by a lower level of expression, as assessed using a predetermined statistical significance standard based on measurements of expression levels.

Thus, the genes expressed or repressed in kidney cells with estrogen exposure are compared to the genes expressed or repressed in kidney cells that were not exposed to estrogen. Pairwise comparisons are made between each of the treatments. A pairwise comparison is the expression data for a given gene under a given treatment condition compared to the expression data for this gene under a second treatment condition. The fold change ratio is then calculated, the p-value based on Student's t-test, the number of present calls, and the expression level for each comparison. A confidence score "CS" is defined as $CS(x)=FC(x)+PV(x)+PC(x)+EL(x)$ where FC, PV, PC and EL are scores assigned to the fold change, p-value, number of present calls, and the expression level, respectively. $FC(x)$ is assigned 5 if the fold change ratio was greater then 1.95 and is assigned 0 if the ratio is between 1.95 and 1.5. $PV(x)$ is assigned 3 if the p-value is less then 0.05 and is assigned 2 if the p-value was between 0.05 and 0.1. $PC(x)$ is assigned 3 if at least 50% of the samples are called P by the Affymetrix algorithm and assigned 1 if only 25% of the samples are called P. $EL(x)$ is assigned 3 if at least two samples have frequency value of 20 or greater and assigned 1 if two samples only have a frequency greater then 15. Penalty points are assigned if the fold change is less then 1.5, the p-value is greater then 0.2 or the frequency values were below 15 ppm. $CS(x)$ ranged for −14 to 14 with qualifiers having a score of 14 considered the most significant changes. Genes with 11 or more points in any one pairwise comparison is considered to be significant. Real-time PCR and histology analyses are then performed to confirm the identity of the genes, essentially as described previously (9,10), which are herein incorporated by reference. The above described analysis can be used to identify candidate agents that are "estrogen-like" in that they have a differential expression profile which is in the most preferred embodiment substantially the same as estrogen's. For instance, in one embodiment, the expression levels for the genes upon exposure to the respective compounds is at least within 50% of each other.

C. Biological Samples from Other Organs

The above described methods, assay and analysis can be applied to biological samples from any tissue, including the uterus, pituitary gland, liver, brain, colon, breast, adipose tissue, etc. In preferred embodiments, the biological samples are from the kidney, pituitary gland and the uterus.

D. The Plurality of Genes

Pursuant to the above described methods, the genes listed in Table II were identified as being differentially expressed upon exposure to estrogen. Genes in which expression is induced by estrogen are considered to be genes of the "first group," whereas genes that are repressed by estrogen are considered to be in the "second group".

Specifically, the estrogen modulated genes in the kidney are Tissue Factor, CYP7B1, BCAT1, STAT5A, GADD45G, BHMT, SAHH, NTT73, ABCC3. Of these genes, estrogen induced expression in all but BHMT and SAHH, where it repressed expression.

Thus, one disclosed embodiment is a plurality of genes, wherein in the first group, where gene expression in kidney cells is induced by estrogen exposure, the plurality of genes comprise NTT73 and ABCC3. Another disclosed embodiment is a plurality of genes wherein the "first group" comprises CYP7B1 in kidney cells. In another embodiment, the plurality of genes of the "second group," where gene expression in kidney cells is repressed by estrogen exposure, comprises at least BHMT and SAHH.

Another disclosed embodiment is directed to a plurality of genes in kidney cells, wherein the first group comprises Tissue Factor, CYP7B1, BCAT1, STAT5A, and GADD45G, and wherein said second group comprises BHMT.

Another disclosed embodiment is directed to a plurality of the genes wherein the first group comprises CYP7B1, TF, SCYA28, Iga, Vk28, PHD 2, ELF 3, TIM1, STAT5A, COR1, BCAT1, ABCC3, TIM2, NAT6, RGS3, GNBP3, BCL7A, 17βDHH, FYVE ZFP, NTT73, AGPS, TRIM2, HBACH, CIS2, CYP27B1, and STAT5B, wherein said second group comprises SAHH, ADH1A7, RARRES2, and BHMT. Another disclosed embodiment relates to a plurality of genes, wherein the first group comprises COR1 and GNBP3.

The estrogen modulated genes in the pituitary gland are STAT5B, GADD45G, Kallikrein-9, and FSHb, the expression of which is induced by estrogen for all but FSHb, which is repressed.

Thus one embodiment relates to a plurality of genes in the pituitary gland, wherein the first group comprises STAT5B and GADD45G.

Another embodiment relates to a plurality of genes, wherein the first group comprises STAT5B, GADD45G1 and Kallikreins genes in the pituitary.

Yet another embodiment relates to a plurality of genes, wherein the second group of genes in the pituitary gland comprise FSHb.

Pursuant to the above methods, the inventors discovered that the estrogen modulated genes in the uterus comprise SFRP4, Deiodinase (type II), Procollagen (type I, Alpha I), vimentin and IGFBP4, Scavenger receptor, AI121305, ALOX15, BCAT1, SiAMOX, C3, FOS, MAP2k1, CEBPb, EGR1 and CYP1A1. All of these genes are induced by estrogen in the uterus except for Scavenger receptor and CYP1A1, which are repressed.

Thus, one embodiment is directed to a plurality of genes in the uterus, wherein the first group comprises SFRP4, Deiodinase (type II), Procollagen (type I, Alpha I), vimentin and IGFBP4.

Another embodiment of the invention is directed to the plurality of genes, wherein the first group in the uterus comprises AI121305, ALOX15, BCAT1, SiAMOX, C3, FOX, MAP2k1, CEBPb and EGR1.

Another embodiment is directed to a plurality of genes wherein the first group in the uterus comprises SFRP4, Deiodinase (type II), Procollagen (type I, Alpha I), vimentin and IGFBP4, Scavenger receptor, AI121305, ALOX15, BCAT1, SiAMOX, C3, FOS, MAP2k1, CEBPb and EGR1.

In another embodiment, the plurality of genes in the second group in the uterus comprises CYP1A1.

In yet another embodiment, the plurality of genes in the second group in the uterus comprises Scavenger receptor.

Methods of Identifying Agents

Based upon the above described methods for determining differential expression of genes in various organs, another aspect of the invention relates to the identification of candidate agents that have the same or substantially the same biological effect of a known agent, such as estrogen or another hormonal combination of known biological effect. An "agent" could be any compound of unknown biological effect on genes in a given body site. Specifically, the invention relates to a method for identifying an agent having a desired effect on gene expression in an organ, wherein said desired effect represents a first plurality of genes differentially expressed at various levels, which method comprises:

exposing, in vivo or in vitro, organ cells to the agent;

measuring expression levels of a multiplicity of genes in the organ cells exposed to the agent and organ cells without the exposure, the multiplicity being greater than said first plurality;

determining, using a predetermined statistical significance standard, genes which are differentially expressed in the organ cells exposed to the agent and the organ cells without the exposure, the genes constitute a second plurality; and comparing the expression levels of genes in the second plurality with the expression levels of genes in said first plurality, wherein the agent is identified as having said desired effort if said first and second pluralities are the same and said expression levels in said first and second pluralities are substantially the same. The "organ cells" may be from any type of biological sample, as described above. In a preferred embodiment, such cells are from the kidney, pituitary gland or uterus. The "first plurality of genes" and "second plurality" of genes can be identified through a nucleotide array or filter, as described above. The comparing is performed using a suitable statistical technique with the assistance of known and commercially available programs, also as described above.

Another embodiment relates to an agent identified by the above method.

Yet another embodiment relates to a gene chip comprising any one or more of the above plurality of genes.

Pharmaceuticals and Methods of Treating

The identification of agents that induce or repress the expression of a gene associated with a given disorder or condition can lead to the development of pharmaceuticals that can be administered to a patient at therapeutically effective doses to prevent, treat, or control such disorder or condition.

Some conditions associated with estrogen regulation of gene expression in the kidney are known. For instance, in women, high estrogen levels preceding ovulation, during pregnancy, and resulting from estrogen administration commonly results in body water retention (23,24). Increased renal sodium reabsorption is a major mechanistic component for the elevated fluid retention (25). In rats, estrogen has been shown to increase thiazide-sensitive NaCl cotransporter expression levels(26), providing one possible molecular basis for estrogen effects on sodium retention.

Pursuant to the methods of the invention as disclosed above and as exemplified in greater detail in the Examples below, two additional estrogen regulated genes that influence sodium retention were identified. First, estrogen (E2) treatment increased mRNA levels for NTT73 (27), which is a sodium and chloride dependent transporter, known to regulate sodium retention. Second, E2 treatment also induced mRNA levels for ABCC3, a member of a family of genes which are known to modulate epithelial sodium channel activity (28). The physiological role of E2 regulation of these genes may lie in the large volume expansion required during pregnancy. The ED50 value for E2 activation of gene expression in the kidney was about 10-fold higher than that required for uterine weight increases (FIG. 5), perhaps a mechanism to ensure that normally estrogen actions only occur in the kidney when very high levels of estrogen are present, as during pregnancy.

Premenopausal women survive septic shock better than comparably aged males while postmenopausal women have a diminished survival advantage. Since volume loss is a major cause of morbidity in shock, it is expected that enhanced sodium and water retention due to elevated expression of NTT73(27) by E2 plays a role in this protective process. Thus, one disclosed embodiment relates to a method for identifying an agent capable of maintaining vascular volume in septic shock comprising exposing, in vivo or in vitro, kidney cells to an agent, measuring expression levels of NTT73 and ABCC3 in kidney cells exposed the agent and in kidney cells not exposed to the agent; comparing the expression levels of the NTT73 and ABCC3 with the expression levels of the genes kidney cells exposed to estrogen. The candidate agent identified by this process can be used in pharmaceuticals for purposes of maintaining vascular volume in the treatment of septic shock.

Another estrogen modulated gene in the kidney with biological significance is CYP27B1, the enzyme responsible for the rate limiting conversion of inactive 25-hydroxy vitamin D3 into active 1,25-dihidroxy vitamin D (29). This process is known to occur in the proximal tubules of the kidney and has been shown to be stimulated by estrogen treatment of birds(30). Urinary calcium excretion is increased in postmenopausal women, while estrogen treatment reduces urine calcium levels (31, 32). The presence of vitamin D receptors within the proximal convoluted tubule and collecting duct tubules of the kidney suggests that E2 induction of CYP27B1 is the basis of this beneficial effect.

Thus, the invention relates to a method of identifying agents that are capable of enhancing calcium uptake in postmenopausal women comprising exposing, in vivo or in vitro, kidney cells to an agent, measuring expression levels of CYP7B1 in kidney cells exposed the agent and in kidney cells not exposed to the agent; comparing the expression levels of the CYP7B1 with the expression levels of the genes in kidney cells exposed to estrogen. The agent identified by this process can be used in pharmaceuticals for purposes of enhancing calcium uptake in postmenopausal women.

It is known that estrogen treatment reduces expression of betaine:homocysteine methyltransferase (BHMT) and S-adenosylhomocysteine hydrolase (SAHH), two enzymes involved in the methionine/homocysteine cycle (34). Elevated plasma homocysteine levels are now recognized as an important risk factor for the development of cardiovascular disease (35), and estrogen treatments reduced plasma homocysteine levels in postmenopausal women. Thus, the regulation of BHMT and SAHH provides a mechanistic link for this effect.

Thus, one embodiment disclosed herein relates to a method of identifying candidate agents for treating cardiovascular disorders comprising measuring expression of BHMT and SAHH in kidney cells exposed to an agent and in kidney cells with such exposure, comparing the expression levels of BHMT and SAHH with the expression levels of the genes in kidney cells exposed to estrogen. The agent identified by this process can be used in pharmaceuticals for purposes of treating cardiovascular disorders.

Finally, E2 treatment induced expression of COR1 (chemokine orphan receptor 1, RDC1) an orphan G-protein coupled receptor (37), along with the guanylate nucleotide binding protein 3 (GNBP3) and the regulator of G-protein signaling 3 (RGS3), suggesting these proteins may form a functional unit. RDC1 is a receptor for the potent vasodilatory peptide adrenomedullin and calcitonin gene-related peptide, CGRP (38). Administration of CGRP to ovariectomized rats does not produce a decrease in kidney vascular resistance; however, in ovariectomized rats treated with E2 or in pregnant rats, injection of CGRP significantly decreases kidney vascular resistance (39). The observed increased expression of RDC1 in kidney provides a mechanism for the E2 induction of sensitivity to CGRP in the kidney, resulting in the large increase in renal flow seen during pregnancy (40).

Thus, one embodiment disclosed herein relates to a method of identifying candidate agents for treating conditions associated with reduced renal flow, such as caused by diuretics or congestive heart failure. Toxicity and therapeutic efficacy of such agents identified by the above methods can be determined by standard pharmaceutical procedures in cell cultures or experimental animals, for example, for determining the LD50 (the dose lethal to 50% of the population) and the ED50 (the dose therapeutically effective in 50% of the population). The dose ratio between toxic and therapeutic effects is the therapeutic index and can be expressed by the ratio, LD50/ED50. compounds that exhibit large therapeutic indices are preferred. While compounds that exhibit toxic side effects can be used, care should be taken to design a delivery system that targets such compounds to the site of affected tissue to minimize potential damage to normal cells and thereby reduce side effects.

The data obtained from the cell culture assays and animal studies can be used to formulate a dosage range for use in humans. The dosage of such compounds likes preferably within a range of circulating concentrations that include ED50 with little or no toxicity. The dosage can vary within this range depending upon the dosage form employed and the route of administration.

The pharmaceuticals of the present invention can be formulated by standard techniques using one or more physiologically acceptable carriers or excipients and the biologically active agent. The agents and its physiologically acceptable salts and solvates can be formulated and administered orally, introraly, rectally, parenteraly, epicutaneously, topically, transdermally, subcutaneously, intramuscularly, intranasally, sublingually, intradurally, introcularly, intravenously, intraperioneally, or by inhalation.

With regard to oral administration, the pharmaceutical compositions can take the form of tablets or capsules prepared by conventional means with pharmaceutically acceptable excipient, such as binding agents etc. Tablets may be coated according to methods well known in the art. Liquid preparations can be in the form of solutions, suspensions and syrups or can be initially in dry form for constitution with water or other suitable vehicle. Other additives may include suspending agents, such as sorbitol syrup, cellulose derivatives or hydrogenated edible fats, emulsifying agents or non-aqueous solutions. Preparations for oral administration may also be formulated for a time or controlled release of the active ingredient using techniques well know in the art of the invention.

Other formulations of the pharmaceuticals of the invention may be depot preparations for administration via implantation.

The pharmaceutical compositions of the present invention may be presented in a pack or dispenser device that contains one or more unit dosage forms containing the active ingredient. The pack can for example comprise metal or plastic foil, for example a blister pack. The pack or dispenser would contain instructions for administration.

Methods of Monitoring

The identification of the plurality of genes described above provides a powerful tool for assessing the progression of a state, condition or treatment. Specifically, a plurality of genes can be identified in a patient prior to an event, such as menopause, surgery, the onset of a therapeutic regime, or the completion of a therapeutic regime, to provide a base line result. This base-line can then be compared with the result obtained using identical methods either during or after such event. This information can be used for both diagnostic and prognostic purposes.

Kits

Another embodiment is directed to a kit containing a plurality of genes, preferably on a substrate. The kit also may comprise one or more containers or packages, along with reagents, solutions and possibly instructions for use.

All of the cited references are herein incorporated by reference. The invention is further described by the following Examples, which do not limit the invention in any manner.

EXAMPLES

Example 1

Introduction to Study and Animal-Related Procedures

Introduction

Estrogen receptors are expressed in numerous organs, although only a few organs are considered classical targets for estrogens. A systematic survey of estrogen regulation of approximately 10,000 genes in 13 tissues from wild type and ERβKO mice treated subcutaneously with vehicle or 17β-estradiol (E2) for six weeks was conducted. As expected, the uterus and pituitary had the greatest number of genes regulated by E2, while, surprisingly, the kidney had the third largest number of regulated genes. Some of these kidney regulations may provide mechanisms for known physiological effects of estrogens. For example, E2 induction of CYP27B1, the rate limiting enzyme in the synthesis of 1,25-dihydroxy vitamin D, may explain the ability of estrogens to decrease urinary calcium excretion in women. In situ hybridizations localized E2 regulation in the kidney to the juxtamedullary proximal and distal collecting tubule epithelial cells in both the mouse and rat. E2 regulations in the kidney were intact in the ERβKO mice, and the ERα selective agonist propyl pyrazole triol acted similarly as E2, together suggesting an ERα mediated mechanism. Finally, the combination of the AF1-selective agonist tamoxifen plus mice expressing an AF1-deleted version of ERα (previously designated as ERα knockouts) allowed clear identification of genes dependent upon ERα AF1 activity and genes dependent upon ERα AF2 activity. Both AF1 and AF2 dependent genes were stimulated by E2 with the same $ED_{50}$, indicating that sensitivity of gene regulation in the kidney depends upon ER ligand binding and not on the subsequent ER activation mechanisms.

Animal-Related Procedure

Animals—Wldtype 129 strain female mice or Sprague-Dawley rats (bred at Wyeth or obtained from Taconic Farms) were placed on a casein-based diet at approximately 6 weeks of age. One week later, the animals were ovariectomized. Commencing the day after ovariectomy, each animal received a daily subcutaneous treatment with vehicle (50% DMSO, 50% phosphate buffered saline) or vehicle containing treatments for six weeks. Each group consisted of six or seven animals. Approximately 2 hours following the final treatment, the animals were euthanized with selected tissues frozen in liquid nitrogen for RNA analysis or on dry ice for histology.

Example 2

Preparation of Microarray

GeneChip—Total RNA was prepared separately from each individual organ by using Trizol (Invitrogen) followed by subsequent repurification on Rneasy columns (Qiagen). In general, two pools of RNA were created using equal amounts of RNA from three mice. For small organs such as pituitary, an equal amount of RNA from six animals was combined.

Target Preparation and Array Hybridization—Total RNA was used to generate biotin labeled cRNA target as described (8) which was hybridized to the murine MG_U74Av2 probe arrays (Affymetrix, Santa Clara, Calif.) for 16 h at 45° C. Eleven biotin-labeled cRNAs at defined concentration were spiked into each hybridization and used to convert average difference values to frequencies expressed as parts per million.

Example 3

Data Selection and Analysis

Pairwise comparisons were made between each of the treatments. We calculated the fold change ratio, the p-value based on Student's t-test, the number of present calls, and the expression level for each comparison. A confidence score (CS) was defined as $CS(x)=FC(x)+PV(x)+PC(x)+EL(x)$ where FC, PV, PC and EL are scores assigned to the fold change, p-value, number of present calls, and the expression level, respectively. $FC(x)$ was assigned 5 if the fold change ratio was greater then 1.95 and was assigned 0 if the ratio was between 1.95 and 1.5. $PV(x)$ was assigned 3 if the p-value was less then 0.05 and was assigned 2 if the p-value was between 0.05 and 0.1. $PC(x)$ was assigned 3 if at least 50% of the samples are called P by the Affymetrix algorithm and assigned 1 if only 25% of the samples are called P. $EL(x)$ was assigned 3 if at least two samples had a frequency value of 20 or greater and assigned 1 if two samples only had a frequency greater then 15. Penalty points were assigned if the fold change was less then 1.5, the p-value was greater then 0.2 or the frequency values were below 15 ppm. $CS(x)$ ranged for −14 to 14 with qualifiers having a score of 14 considered the most significant changes. Genes with 11 or more points in any one pairwise comparison were considered to be significant and were included for further analysis. Real-time PCR on individual RNA samples and histology analyses were performed essentially as described previously (9, 10).

Example 4

Discussion of Results

To begin a systematic survey of estrogen receptor regulation of gene expression in the mouse, ovariectomized wild-type (WT) and ERβKO mice were treated by daily subcutaneous administration of either vehicle or 20 μg/kg/day 17β-estradiol (E2) for six weeks. RNA prepared from 13 organs was analyzed by microarray for estrogen regulation of gene expression. The resulting data set was queried for genes whose regulation was dependent on ERα or ERβ. For ERα regulation, the basal expression level was predicted to be the same in WT and ERβKO mice, with E2 induction or suppression occurring in both WT and ERβKO mice. (FIG. 1). For ERβ regulation, basal expression was predicted to remain constant, with E2 induction or suppression occurring in WT mice but not in ERβKO mice. ERα pattern regulations were found in well known estrogen target tissues such as the uterus (514 inductions, 19 repressions), pituitary (56 inductions, 30 repressions) and bone marrow (3 inductions, 3 repressions). In contrast, essentially no genes could be discerned that fit the predicted ERβ regulation pattern in any tissue.

Figure 2A:
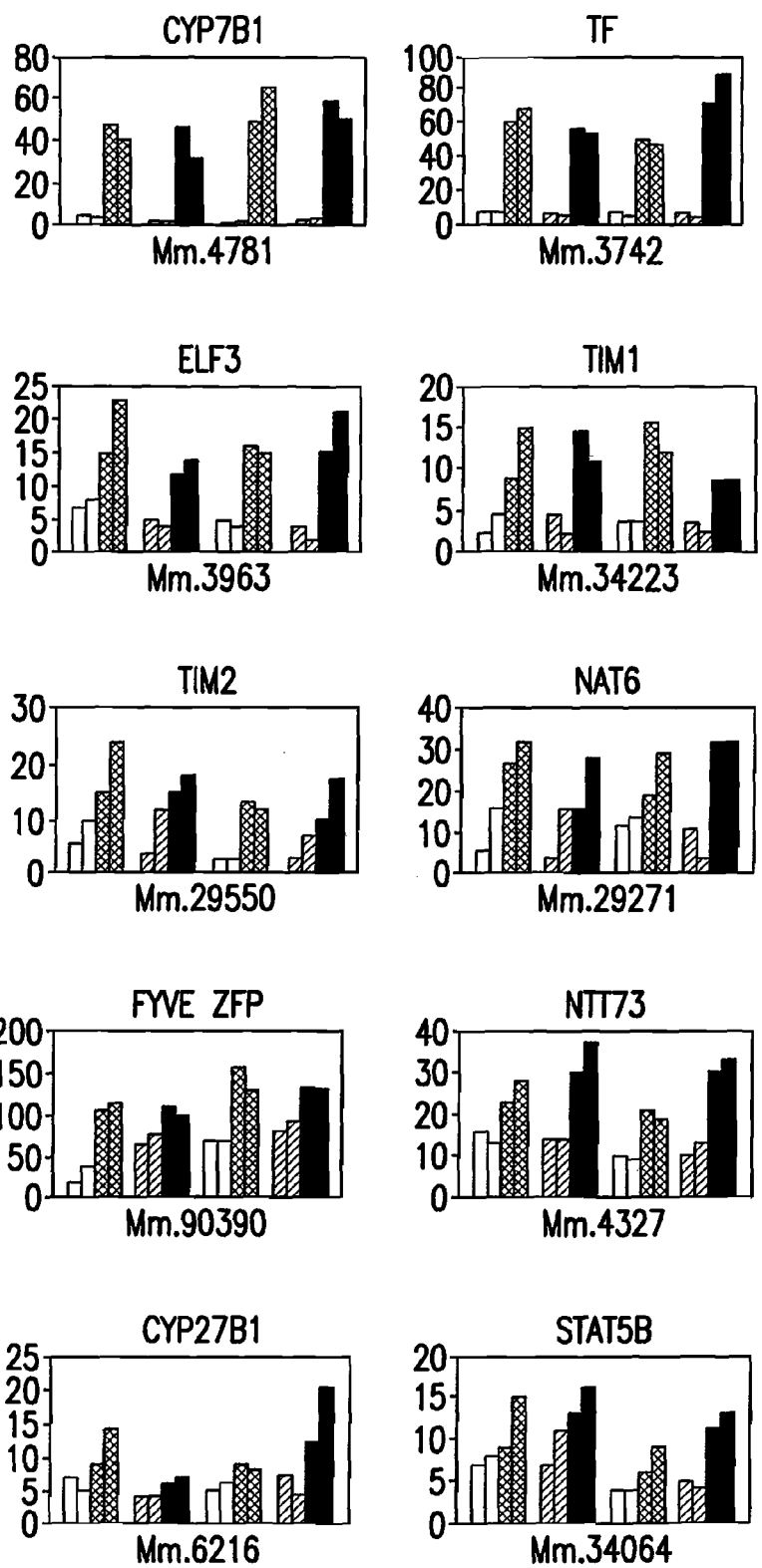
FIGS. 2A-2C show a series of bar graphs showing gene expression levels of known genes regulated in the kidney in an ERα pattern. The expression levels (parts-per-million) are shown for the indicated genes in WT mice treated with vehicle (light blue bars), WT mice treated with E2 (dark blue bars), ERβKO mice treated with vehicle (light green bars), and ERβKO mice treated with E2 (dark green bars) using U74v2 subA, BS and C microarrays. Expression was measured in two independent sets of animals, with two groups of animals for each treatment in each study. A gene name abbreviation is shown above each graph, with the corresponding Unigene designation shown below. The genes are graphed in approximate order of regulation from largest induction (CYP7B1) to largest repression (BHMT).
Figure 2B:
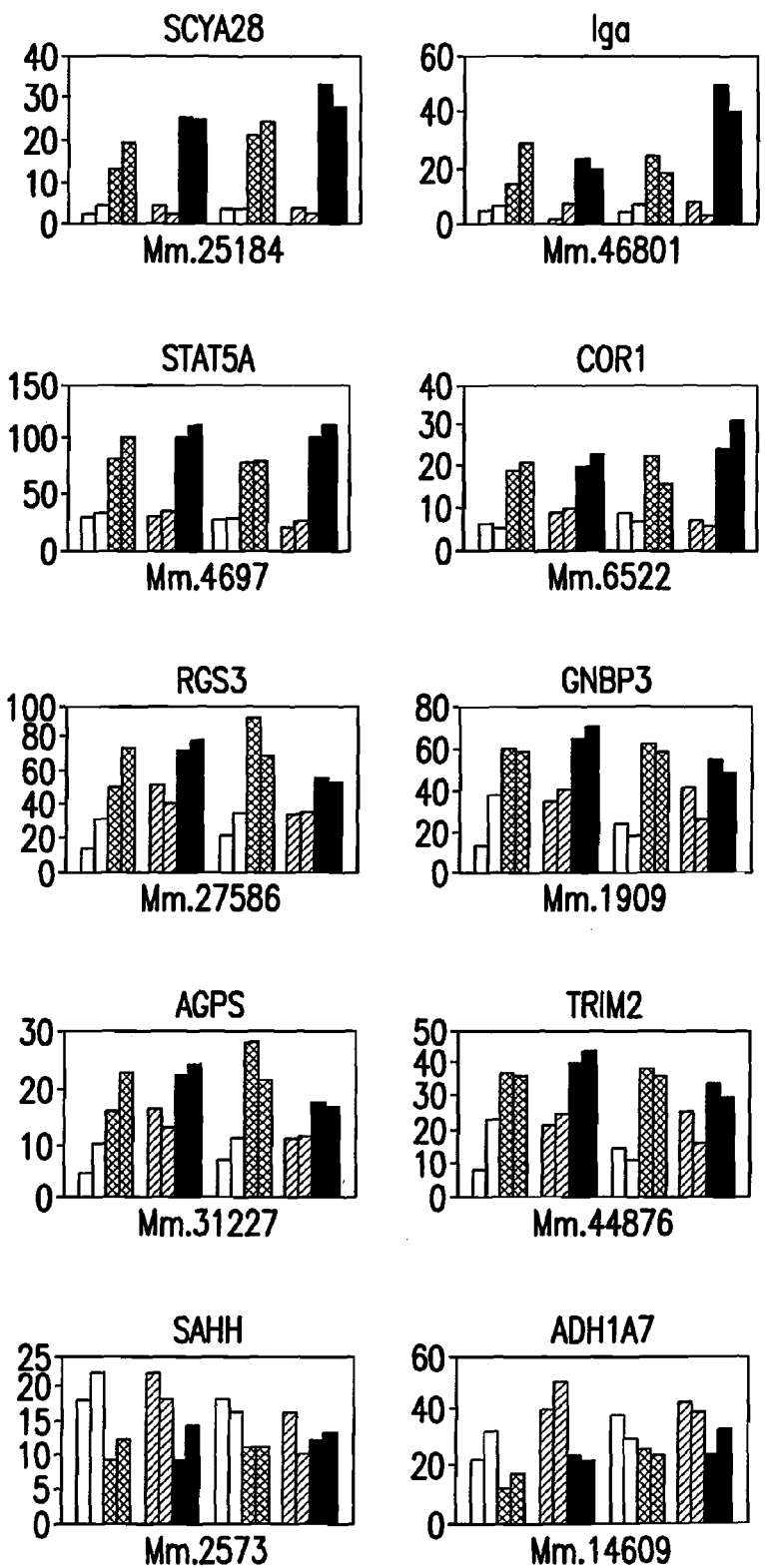
Figure 2C:
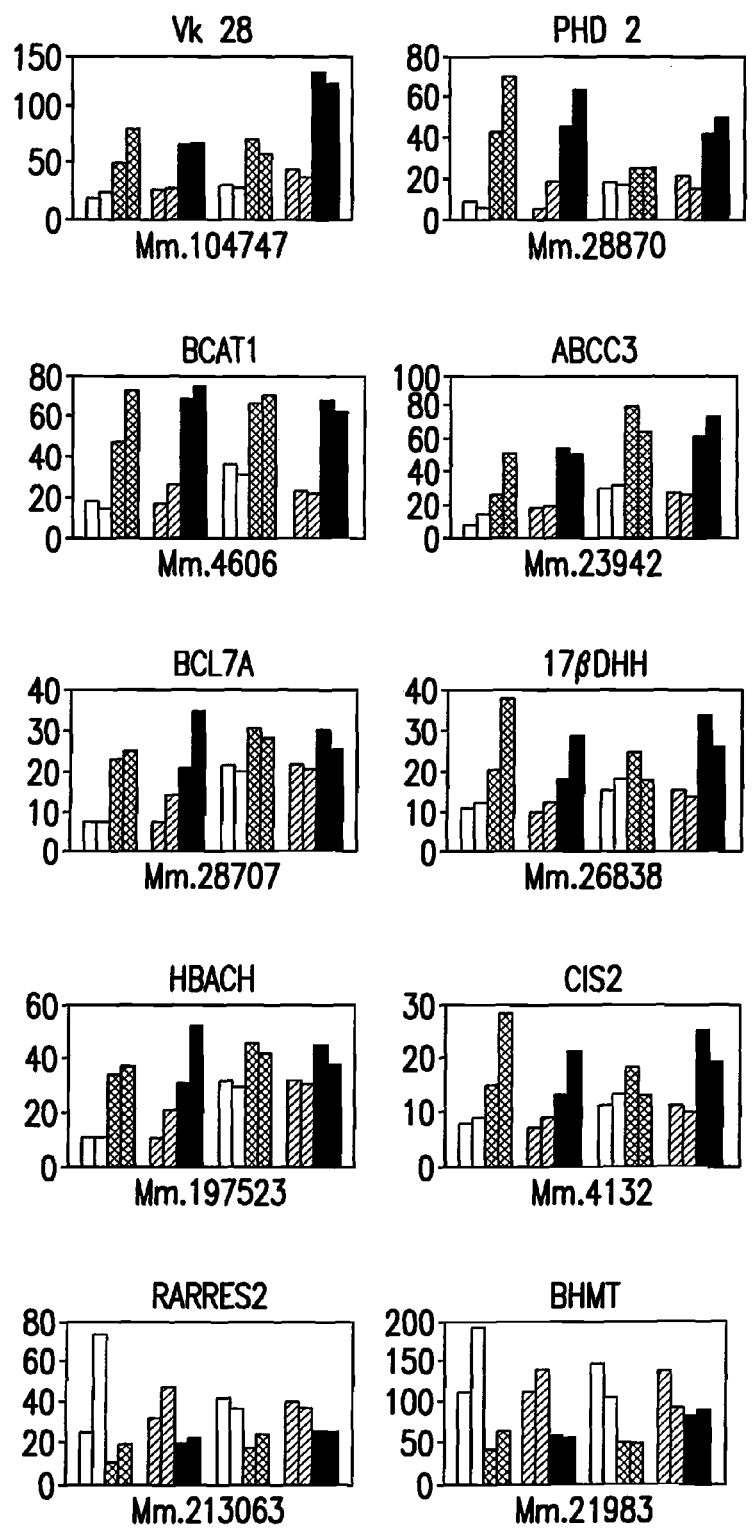

Surprisingly, the kidney had a very large number of genes regulated at least 2-fold by E2 (26 inductions, 4 repressions; FIG. 2). To further characterize E2 regulation of gene expression in the kidney, in situ hybridization was used to localize E2 induction of CYP7B1, TF, STAT5A and GADD45G In each case, induction of gene expression occurred in the juxtamedullary region of the kidney (FIG. 3) primarily in the proximal and distal tubule epithelium (not shown). Estrogen regulation of STAT5A and GADD45G also occurred in rat kidney juxtamedullary region (FIG. 4), demonstrating that the estrogen responsiveness of kidney is not limited to the mouse.

Figure 5A:
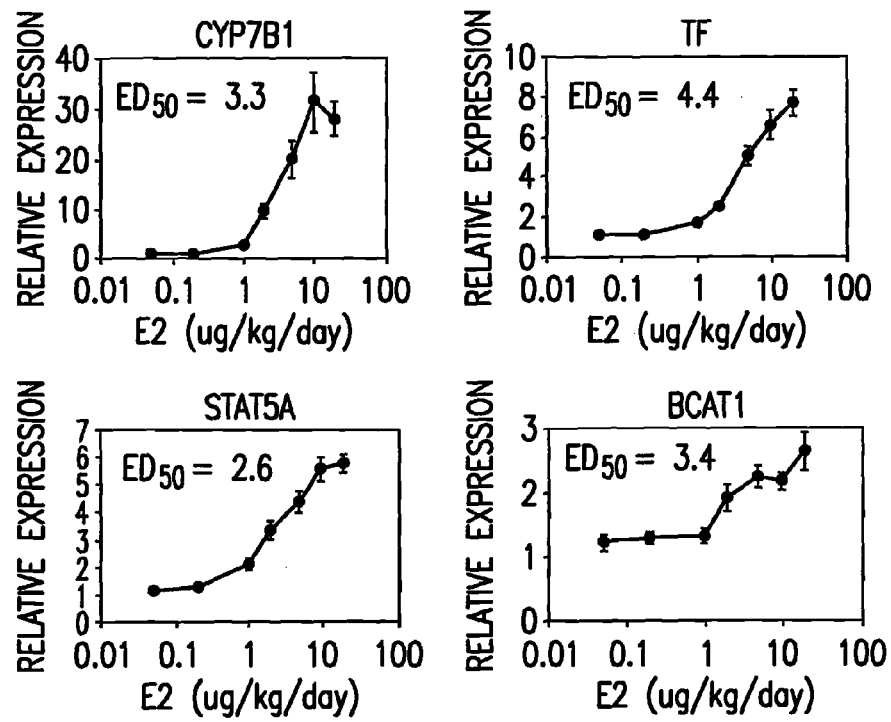
FIGS. 5A-5B show a series of graphs showing expression levels for various genes. Ovariectomized WT mice were treated with vehicle or various doses of E2 for six weeks. (A) Kidney gene expression values (mean±SEM) were determined by real-time PCR for each individual animal and normalized for GAPDH expression. The mean expression level in vehicle-treated mice was defined as 1 for each gene. (B) Uterine wet weights (mg) and gene expression values (mean±SEM).
Figure 5B:
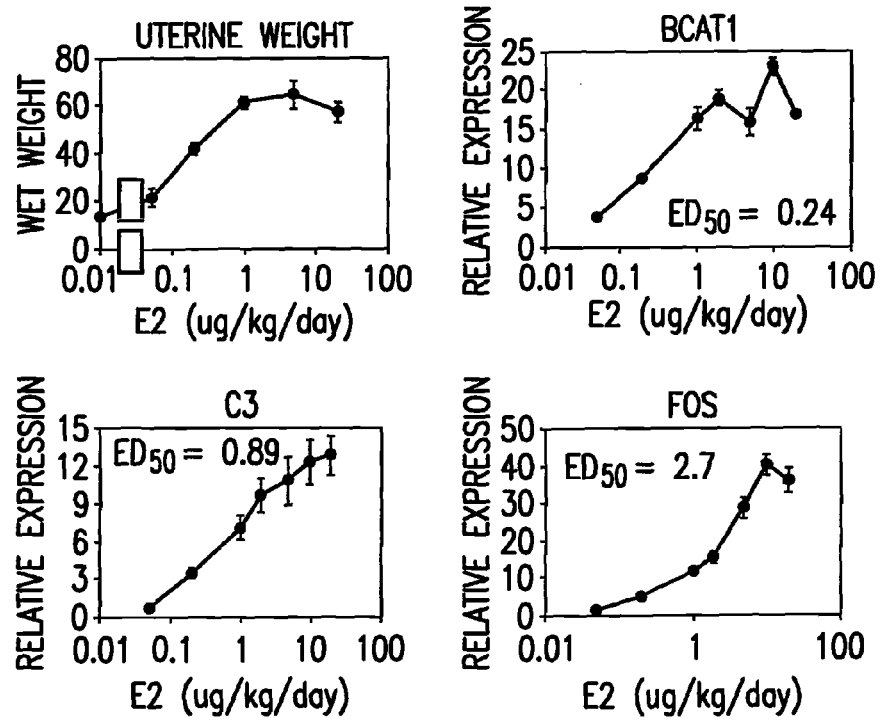
Figure 6A:
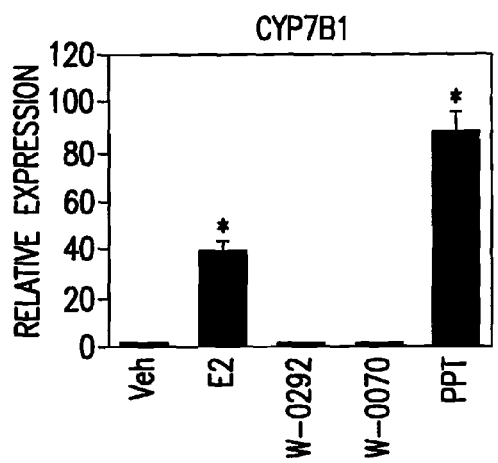
FIGS. 6A-6D show a series of bar graphs depicting relative expression levels for various genes. Ovariectomized WT mice were treated with vehicle, 20 µg/kg/day E2, 5 mg/kg/day W-0292, W-0070 or propylpyrazole triol (PPT) for six weeks. Kidney gene expression values were determined by real-time PCR for each individual animal and normalized for GAPDH expression. The mean expression level in vehicle-treated mice was defined as 1 for each gene. *p<0.01 for comparison to vehicle treated animals.
Figure 6B:
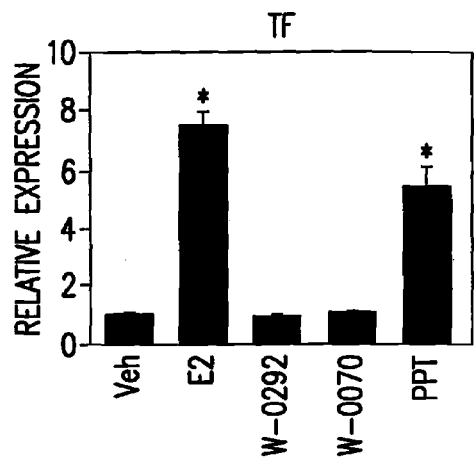
Figure 6C:
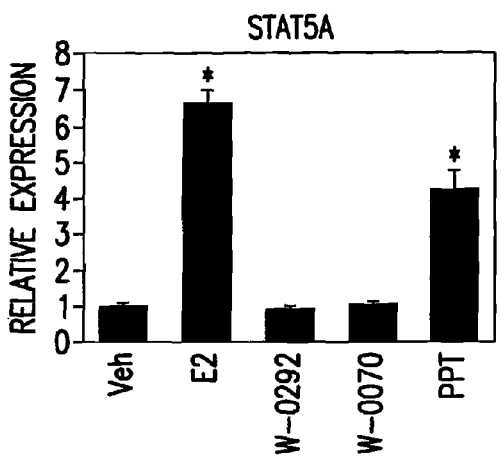
Figure 6D:
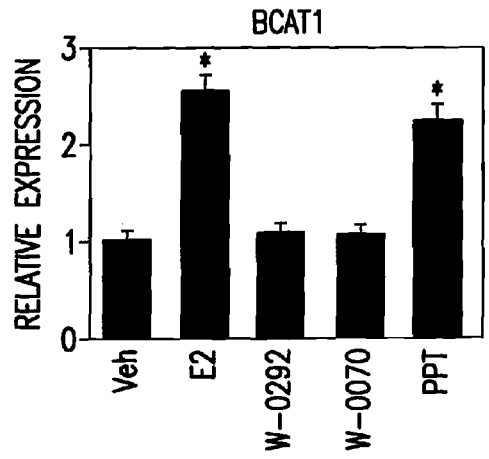

The $ED_{50}$s for E2 stimulation of CYP7B1, TF, STAT5A, and BCAT1 in the kidney were all very similar at about 3 μg/kg/day (FIG. 5). Although this is approximately 10-fold greater than the $ED_{50}$ dose of E2 required for uterine weight increases, the $ED_{50}$ for gene induction in the uterus can vary by 20-fold, from 0.2 ug/kg/day E2 for BCAT1 induction to 2.7 ug/kg/day for c-fos (FIG. 5). The E2 induction of gene expression in the kidney at the same dose as induction of well characterized genes such as c-fos in the uterus suggests that regulation of kidney gene expression occurs at physiological levels of E2.

Confirmation of the role of ERα in the induction of kidney gene expression was obtained with 4-propyl-1,3,5-Tris(4-hydroxy-phenyl)pyrazole (PPT) a compound which exclusively activates ERα but not ERβ (11). Treatment with PPT induced expression of CYP7B1, TF, STAT5A and BCAT1 to a similar extent as did treatment with E2 (FIG. 6). Further, two ERβ selective agonists (W-0292 and W-0070, both approximately 75-fold selective for ERβ compared to ERα by in vitro binding assays; data not shown) failed to stimulate expression of any of these four genes (FIG. 6). Finally, in agreement with previous results, ERα mRNA was detectable within the mouse kidney (FIG. 7). The regulation of these genes in WT and ERβKO mice, the similar E2 $ED_{50}$ for each gene, the activity of a selective ERα agonist, the inactivity of selective ERβ agonists, and the expression of ERα within the kidney together suggest a single, ERα mediated pathway for regulation of these genes.

It has been recognized that a commonly utilized strain of ERαKO mice (12) in fact expresses an ERα protein lacking only AF1, due to alternative splicings of the exon containing the targeted knockout mutation(13, 14). The resulting truncated ERα proteins, referred to here as ΔAF1-ERα, have the ability to stimulate expression of a synthetic estrogen response element driven promoter (14). As found previously for ERαKO mice, the level of this misspliced transcript in the uterus of ERαERβKO mice was lower than the level of full length message in WT mice (FIG. 7). Again as expected, the amount of intact ERα mRNA was much lower in the whole kidney than in uterus from WT mice. However, the level of ΔAF1-ERα mRNA was actually greater in the ERαERβKO kidney than was intact ERα mRNA in WT kidney. No ERβ mRNA could be detected in either uterus or kidney from the ERαERβKO mice.

The presence of ΔAF1-ERα at significant levels in the kidney allows determination of the relative contribution of AF1 and AF2 to E2 regulation of individual genes. To determine whether AF1 or AF2 regions of ERα were required for induction of CYP7B1, TF or BCAT1 in the kidney, WT, ERαERβKO or ERαKO mice were treated with E2 or the AF1 selective agonist tamoxifen (15). Expression of CYP7B1 was induced by E2 but not by tamoxifen in WT mice (FIG. 8), suggesting that induction of CYP7B1 occurred through AF2. Consistent with this hypothesis, E2 also increased CYP7B1 expression in mice expressing ΔAF1-ERα (either ERαERβKO or ERαKO mice). This E2 induction was blocked by an excess of ICI-182780, confirming the regulation occurred through ER. Together, these two lines of evidence suggest that induction of CYP7B1 is an AF2 dependent process. In contrast, TF expression was induced by both E2 and tamoxifen in WT mice. Neither compound could induce TF expression in ERαERβKO mice (which express only ΔAF1-ERα). This suggests that induction of TF occurs through an AF1 mediated pathway. Finally, BCAT1 was also induced by both E2 and tamoxifen in WT mice. However, in ERαERβKO mice, E2 stimulated BCAT1 expression but tamoxifen did not. These results suggest that BCAT1 expression can be stimulated through either AF1 or AF2 mechanisms. In WT mice, tamoxifen stimulates expression through AF1 only. Since ΔAF1-ERα lacks the AF1 region necessary for tamoxifen activity, tamoxifen cannot stimulate BCAT1 expression in ERαERβKO mice. In contrast, E2, which can stimulate BCAT1 expression through either AF1 or AF2, can still stimulate expression in the ΔAF1-ERα expressing mice.

Estrogen receptors α or β are found in almost all organs of the body, yet relatively few tissues are considered targets for estrogen action. To begin to develop a more complete understanding of estrogen biology, estrogen responsive genes in 13 tissues from WT and ERβKO mice were characterized. In general, many tissues showed patterns of E2 regulation consistent with an ERα mechanism, including such known target organs as uterus, pituitary, and bone. Surprisingly, no E2 regulations were found that fit the expected pattern for ERβ regulations. This was true even in organs expressing moderately high levels of ERβ such as the bladder and lung (7). At least three mechanisms could explain the lack of detection of expected ERβ responses. First, it has been proposed that a major function of ERβ is to modulate the activity of ERα(16). For example, expression of the Ki-67 protein was constitutively elevated in uterus of ERβKO mice, i.e. in the ERβKO mice its expression was always equivalent to the E2 stimulated levels in WT animals (17). The survey criteria used here would not detect this pattern. Further analysis of these data has revealed many genes in multiple tissues which also have this "nonclassical" pattern of regulation whereby expression is constitutively elevated in both vehicle and E2 treated ERβKO mice (data not shown). Second, analysis of whole organs may easily miss regulations occurring in only selected cell subtypes within an organ. For example, initial analysis of kidney did not identify GADD45G as being regulated by E2, because GADD45G expression is regulated only in tubule epithelial cells. The unregulated expression of GADD45G throughout most of the kidney sufficiently diminished the fold induction so as to be less than 2-fold in whole organ samples. The combination of laser capture microdissection with microarray technology (18) should allow detection of ERβ regulated genes with a classical pattern of regulation.

Figure 3:
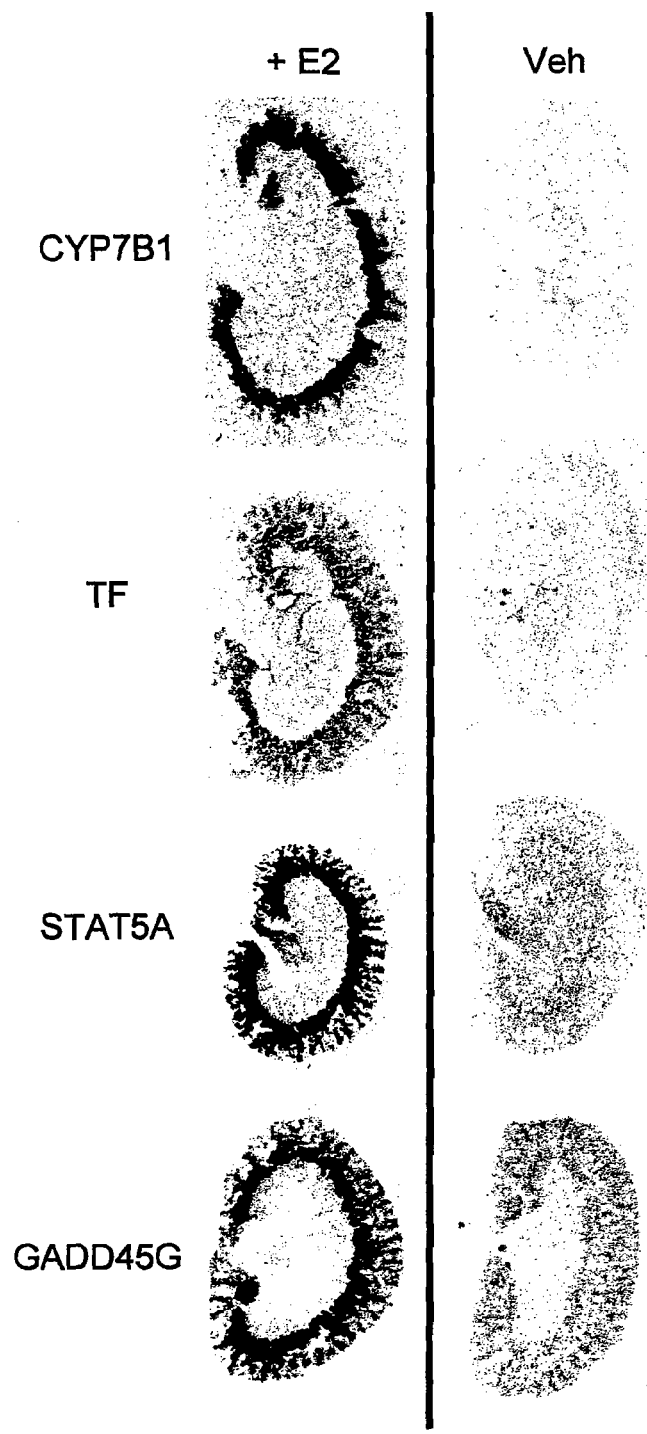
FIG. 3 shows histological sections of the kidney in in situ hybridization studies using antisense probes for CYP7B1, TF, STAT5A or GADD45G in ovariectomized mice treated with vehicle or 20 µg/kg/day E2 for six weeks. No signal was detected with the corresponding sense probes.
Figure 4:
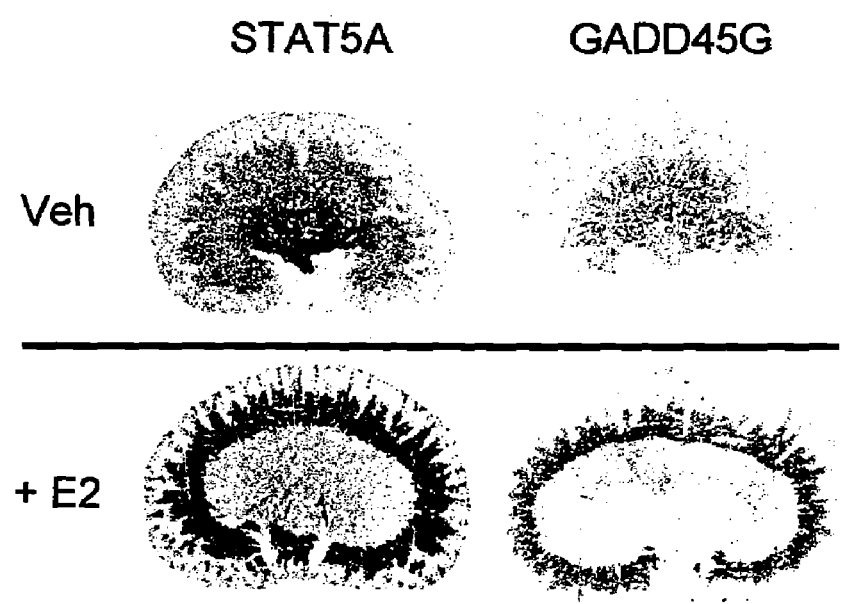
FIG. 4 shows histological sections of the kidney in in situ hybridization using antisense probes for STAT5A or GAD45G in ovariectomized rats treated with vehicle or 20 µg/kg/day E2 for six weeks. No signal was detected with the corresponding sense probes.

This global survey demonstrates that, unexpectedly, the kidney had a very large number of regulated genes. Both genetic approaches (FIG. 2) and pharmacological approaches (FIG. 6) demonstrated that E2 regulation in the kidney was mediated through ERα. Expression of CYP7B1, TF, STAT5A, and even genes such as GADD45G which are expressed throughout the kidney showed regulation only in tubule epithelium (FIG. 3). Additionally, KIM-1, the rat counterpart of mouse TIM1 and TIM2 (20) is also expressed in proximal tubule epithelial cells (21). Finally, $^3$H-E2 binding localizes to proximal tubule cells following administration to rats(22). Together, these results suggest that ERα directly regulates gene expression in tubule epithelial cells.

Although the observed regulations in the kidney were mediated by ERα, the mechanism of activation of gene expression by ERα was gene specific. Thus studies using tamoxifen, which activates ERα through AF1, along with studies using ΔAF1-ERαKO mice (previously designated as ERKO mice) together indicate that E2 induction of CYP7B1 expression occurred predominantly through an AF1-dependent mechanism, E2 induction of TF expression occurred predominantly through an AF2-dependent mechanism, and E2 induction of BCAT1 expression occurred through both AF1 and AF2 mechanisms (FIG. 8). The $ED_{50}$ values for E2 stimulation of these three genes were all very similar (FIG. 5). Thus, whether a gene is induced through either AF1 or AF2 mechanism does not influence the sensitivity of the gene in the kidney to plasma estrogen levels. Rather, the data indicate that the binding of E2 to ERα would be the rate limiting step in induction of gene expression in the kidney. The maximal fold regulation varied between genes and may depend upon whether and AF1 or AF2 dependent pathway is utilized.

Analysis of 10 kb of upstream putative promoter sequences of E2 induced genes identified good matches to the consensus estrogen response element (ERE) in only a few genes, although ERE half-sites could be identified in most promoters. Many of these genes may be activated through nonclassical ERα mechanisms such as the combination of an ERE half-site with Sp1 binding sites (41). It is unlikely that a nonclassical ERα/AP1 stimulatory mechanism is responsible for these regulations, since ICI182780 functions as a partial agonist in this mechanism (42) while ICI182780 was a complete antagonist for E2 regulation of gene expression in the kidney (FIG. 8). Additionally, E2 induced expression of the transcription factors PHD2, ELF3, STAT5A and STAT5B. It is possible that E2 induction of these transcription factors resulted in the subsequent increase in expression of the remaining genes. For example, CIS2 is a known target for induction by STAT transcription factors (43), suggesting that the E2 induction of CIS2 is mediated indirectly through the E2 induction of STAT5A and STAT5B.

TABLE II

Genes Regulated By Estrogen in Kidney, Uterus and Pituitary Gland

| | Unigene Code | Full name | Why |
|---|---|---|---|
| Kidney | | | |
| Tissue Factor | Mm.3742 | Coagulation factor III | Mechanism is ERα AF1 dependent |
| CYP7B1 | Mm.6216 | Cytochrome P450, 40 (25-hydroxyvitamin D3 1 alpha-hydroxylase) | Mechanism is ERα AF2 dependent |
| BCAT1 | Mm.4606 | Branched chain aminotransferase 1, cytosolic | Mechanism is ERα AF1 + AF2 dependent |
| STAT5A | Mm.4697 | Signal transducer and activator of transcription 5A | Regulated in multiple species (mouse and rat) |
| GADD45G | Mm.9653 | Growth arrest and DNA-damage-inducible 45 gamma | Regulated in multiple species (mouse and rat) |
| BHMT | Mm.21983 | Betaine-homocysteine methyltransferase | A repression by estrogens |
| SAHH | Mm.2573 | S-adenosylhomocysteine hydrolase | |
| NTT73 | Mm.4327 | SODIUM- AND CHLORIDE-DEPENDENT TRANSPORTER NTT73 | |
| ABCC3 | Mm.23942 | ATP-binding cassette, sub-family C (CFTR/MRP), member 3 | |
| Uterus | | | |
| SFRP4 | Mm.42095 | Secreted frizzled-related sequence protein 4 | Induced by estrogens in mouse uterus and human endometrium |
| Deiodinase, type II | Mm.21389 | Deiodinase, iodothyronine, type II | Induced by estrogens in mouse uterus and human endometrium |
| Procollagen, type I, alpha 1 | Mm.22621 | Procollagen, type I, alpha 1 | Induced by estrogens in mouse uterus and human endometrium |
| vimentin | Mm.7 | Vimentin | Induced by estrogens in mouse uterus and human endometrium |
| IGFBP4 | Mm.22248 | Insulin-like growth factor binding protein 4 | Induced by estrogens in mouse uterus and human endometrium |
| Scavenger receptor | Mm.1227 | Macrophage scavenger receptor 1 | Repressed by estrogens in mouse uterus and human endometrium |
| AI121305 | Mm.29959 | RIKEN cDNA 1600029D21 | a set of genes induced by estrogens with a range of ED50 values |
| ALOX15 | Mm.4584 | Arachidonate 15-lipoxygenase | a set of genes induced by estrogens with a range of ED50 values |
| BCAT1 | Mm.4606 | Branched chain aminotransferase 1, cytosolic | a set of genes induced by estrogens with a range of ED50 values |
| SiAMOX | Mm.7190 | Amiloride binding protein 1 (amine oxidase, copper-containing) | a set of genes induced by estrogens with a range of ED50 values |
| C3 | Mm.19131 | Complement component 3 | a set of genes induced by estrogens with a range of ED50 values |
| FOS | Mm.5043 | FBJ osteosarcoma oncogene | a set of genes induced by estrogens with a range of ED50 values |
| MAP2k1 | Mm.1059 | Mitogen activated protein kinase kinase 1 | a set of genes induced by estrogens with a range of ED50 values |
| CEBPb | Mm.4863 | CCAAT/enhancer binding protein (C/EBP), beta | a set of genes induced by estrogens with a range of ED50 values |
| EGR1 | Mm.181959 | Early growth response 1 | a set of genes induced by estrogens with a range of ED50 values |
| CYP1A1 | Mm.14089 | Cytochrome P450, 1a1, aromatic compound inducible | Repressed by estrogens |
| Pituitary | | | |
| STAT5B | Mm.34064 | Signal transducer and activator of transcription 5B | Induced by estrogens |
| GADD45G | Mm.9653 | Growth arrest and DNA-damage-inducible 45 gamma | Induced by estrogens |
| Kallikrein-9 | Mm.200410 | Kallikrein 9 | Induced by 17b-estradiol, not by Premarin |
| FSHb | Mm.46711 | Follicle stimulating hormone beta | Repressed by estrogens |

TABLE III

Genes Regulated By Estrogen in the Uterus

| Mousedata. Qualifier | Pub_Name | Gene Name | Tissue | Mean WT E2 Fold Change |
|---|---|---|---|---|
| 94120_s_at | SPRR2F | small proline-rich protein 2F | Uterus | 38.71 |
| 97413_at | UNK_AI121305 | ESTs, Weakly similar to AF189262_1 GABA-A receptor epsilon like subunit [*R. norvegicus*] | Uterus | 31.68 |
| 101130_at | COLA2 | procollagen, type I, alpha 2 | Uterus | 29.57 |
| 103526_at | PDI2 | peptidyl arginine deiminase, type II | Uterus | 23.01 |
| 99059_at | ELF3 | E74-like factor 3 | Uterus | 22.03 |
| 95343_at | PDI1 | peptidyl arginine deiminase, type I | Uterus | 21.72 |
| 101115_at | LTF | lactotransferrin | Uterus | 19.01 |
| 93481_at | UNK_AI846720 | Cluster Incl AI846720: UI-M-AN1-afi-h-09-0-UI.s1 *Mus musculus* cDNA, 3' end/clone = UI-M-AN1-afi-h-09-0-UI/clone_end = 3'/gb = AI846720/gi = 5490626/ug = Mm.7124/len = 161/STRA = for | Uterus | 17.96 |

TABLE III-continued

Genes Regulated By Estrogen in the Uterus

| Mousedata.Qualifier | Pub_Name | Gene Name | Tissue | Mean WT E2 Fold Change |
|---|---|---|---|---|
| 93097_at | ARG1 | arginase 1, liver | Uterus | 17.45 |
| 104249_g_at | UNK_AW227650 | ESTs, Highly similar to TRANSLOCON-ASSOCIATED PROTEIN, GAMMA SUBUNIT [*Rattus norvegicus*] | Uterus | 16.87 |
| 93797_g_at | LDH1 | lactate dehydrogenase 1, A chain | Uterus | 16.5 |
| 101761_f_at | SPRR2C | small proline-rich protein 2C | Uterus | 16.48 |
| 102805_at | CEACAM1 | CEA-related cell adhesion molecule 1 | Uterus | 16 |
| 98064_at | GLYCAM1 | glycosylation dependent cell adhesion molecule 1 | Uterus | 15.46 |
| AFFX-GapdhMur/M32599_5_at | GAPDH5_Mm_AFFX | Glyceraldehyde-3-phospate dehydrogenase 5' control sequence (*M. musculus*) [AFFX] | Uterus | 15.2 |
| AFFX-GapdhMur/M32599_5_at | GAPDH5_Mm_AFFX | Glyceraldehyde-3-phospate dehydrogenase 5' control sequence (*M. musculus*) [AFFX] | Uterus | 15.2 |
| AFFX-GapdhMur/M32599_5_at | GAPDH5_Mm_AFFX | Glyceraldehyde-3-phospate dehydrogenase 5' control sequence (*M. musculus*) [AFFX] | Uterus | 15.2 |
| 96605_at | UNK_AI787183 | ESTs, Weakly similar to AF1154269_1 LR8 [*M. musculus*] | Uterus | 14.98 |
| 102806_g_at | CEACAM1 | CEA-related cell adhesion molecule 1 | Uterus | 14.48 |
| 93860_i_at | UNK_M17327 | Mouse endogenous murine leukemia virus modified polytropic provirus DNA, complete cds | Uterus | 13.83 |
| 101707_at | ALDH1A7 | alcohol dehydrogenase family 1, subfamily A7 | Uterus | 13.63 |
| 104486_at | UNK_AI850558 | ESTs, Highly similar to ALPHA-2-MACROGLOBULIN PRECURSOR [*Homo sapiens*] | Uterus | 13.29 |
| 98423_at | GJB2 | gap junction membrane channel protein beta 2 | Uterus | 12.6 |
| 104182_at | HGFAC | hepatocyte growth factor activator | Uterus | 12 |
| 94789_r_at | TUBB5 | tubulin, beta 5 | Uterus | 11.55 |
| 98822_at | ISG15 | interferon-stimulated protein (15 kDa) | Uterus | 11.5 |
| 97826_at | UNK_AI465965 | ESTs, Weakly similar to IgG Fc binding protein [*M. musculus*] | Uterus | 10.95 |
| 100026_at | BCAT1 | branched chain aminotransferase 1, cytosolic | Uterus | 10.35 |
| 102316_at | CAPN5 | calpain 5 | Uterus | 10.01 |
| 98092_at | D5WSU111E | DNA segment, Chr 5, Wayne State University 111, expressed | Uterus | 9.77 |
| 102918_at | MUC1 | mucin 1, transmembrane | Uterus | 9.74 |
| 97173_f_at | H2-K2 | histocompatibility 2, K region locus 2 | Uterus | 9.71 |
| 93497_at | C3 | complement component 3 | Uterus | 9.63 |
| 93517_at | COL6A2 | procollagen, type VI, alpha 2 | Uterus | 9.57 |
| 92796_at | AKP2 | alkaline phosphatase 2, liver | Uterus | 9.36 |
| 103824_at | WFS1 | Wolfram syndrome 1 homolog (human) | Uterus | 9.15 |
| 99378_f_at | UNK_M18837 | Mouse MHC class I Q4 beta-2-microglobulin (Qb-1) gene, complete cds | Uterus | 8.9 |
| 99561_f_at | CLDN7 | claudin 7 | Uterus | 8.84 |
| 94305_at | COLA1 | procollagen, type I, alpha 1 | Uterus | 8.78 |
| 92223_at | C1QC | complement component 1, q subcomponent, c polypeptide | Uterus | 8.63 |
| 100134_at | ENG | endoglin | Uterus | 8.53 |
| 92550_at | KRT1-19 | keratin complex 1, acidic, gene 19 | Uterus | 8.53 |
| 103905_at | UNK_AI314958 | ESTs, Highly similar to CARBONIC ANHYDRASE VI [*Ovisaries*] | Uterus | 8.44 |
| 93285_at | UNK_AI845584 | ESTs, Highly similar to DUS6_RAT DUAL SPECIFICITY PROTEIN PHOSPHATASE 6 [*R. norvegicus*] | Uterus | 8.39 |
| 92777_at | CYR61 | cysteine rich protein 61 | Uterus | 8.3 |
| 97819_at | GSTTL-PENDING | glutathione S-transferase like | Uterus | 8.12 |
| 93479_at | UNK_AW122413 | Cluster Incl AW122413: UI-M-BH2.2-aow-f-03-0-UI.s1 *Mus musculus* cDNA, 3' end/clone = UI-M-BH2.2-aow-f-03-0-UI/clone_end = 3'/gb = AW122413/gi = 6097916/ug = Mm.7113/len = 470/STRA = rev | Uterus | 7.99 |
| 104099_at | PGLYRP | peptidoglycan recognition protein | Uterus | 7.98 |
| 97507_at | PPICAP | peptidylprolyl isomerase C-associated protein | Uterus | 7.86 |
| 94876_f_at | UNK_AI849207 | ESTs, Weakly similar to AF218940_1 formin-2 [*M. musculus*] | Uterus | 7.77 |
| 96911_at | GNB2 | guanine nucleotide binding protein, beta 2 | Uterus | 7.56 |
| 92608_at | CSRP | cysteine rich protein | Uterus | 7.56 |
| 94269_at | RABAC1 | Rab acceptor 1 (prenylated) | Uterus | 7.46 |
| 93861_f_at | UNK_M17327 | Mouse endogenous murine leukemia virus modified polytropic provirus DNA, complete cds | Uterus | 7.39 |
| 101110_at | COL6A3 | procollagen, type VI, alpha 3 | Uterus | 7.37 |
| 93974_at | 33 POLYPEPTIDE☐ [*R. NORVEGICUS*] | ESTs, Highly similar to G33_RAT GENE 33 POLYPEPTIDE☐ [*R. norvegicus*] | Uterus | 7.34 |
| 98758_at | ALOX15 | arachidonate 15-lipoxygenase | Uterus | 7.33 |
| 99379_f_at | UNK_M27034 | Mouse MHC class I D-region cell surface antigen (D2d) gene, complete cds | Uterus | 7.23 |
| 93078_at | LY6 | lymphocyte antigen 6 complex | Uterus | 7.17 |
| 93290_at | PNP | purine-nucleoside phosphorylase | Uterus | 7.12 |
| 101979_at | GADD45G | growth arrest and DNA-damage-inducible 45 gamma | Uterus | 7.06 |
| 99452_at | LISCH7-PENDING | liver-specific bHLH-Zip transcription factor | Uterus | 7 |

TABLE III-continued

Genes Regulated By Estrogen in the Uterus

| Mousedata.Qualifier | Pub_Name | Gene Name | Tissue | Mean WT E2 Fold Change |
|---|---|---|---|---|
| 94274_at | PFDN5 | prefoldin 5 | Uterus | 6.97 |
| 92880_at | MFGE8 | milk fat globule-EGF factor 8 protein | Uterus | 6.95 |
| 101294_g_at | G6PD2 | glucose-6-phosphate dehydrogenase 2 | Uterus | 6.95 |
| 92759_at | LAMB3 | laminin, beta 3 | Uterus | 6.88 |
| 92585_at | MAP2K1 | mitogen activated protein kinase kinase 1 | Uterus | 6.86 |
| 95232_at | HNRPL | heterogeneous nuclear ribonucleoprotein L | Uterus | 6.79 |
| 104410_at | MIDN-PENDING | midnolin | Uterus | 6.75 |
| 96075_at | WDR1 | WD repeat domain 1 | Uterus | 6.71 |
| 95631_at | PPP4C | protein phosphatase 4, catalytic subunit | Uterus | 6.68 |
| 100412_g_at | AEBP1 | AE-binding protein 1 | Uterus | 6.67 |
| 96634_at | UNK_AI850090 | ESTs, Weakly similar to cDNA EST EMBL: C07816 comes from this gene [*C. elegans*] | Uterus | 6.65 |
| 97282_at | MELA | melanoma antigen, 80 kDa | Uterus | 6.6 |
| 98511_at | RALY | hnRNP-associated with lethal yellow | Uterus | 6.55 |
| 94199_at | KAP | kidney androgen regulated protein | Uterus | 6.45 |
| 93818_g_at | RNP24-PENDING | coated vesicle membrane protein | Uterus | 6.32 |
| 98331_at | COL3A1 | procollagen, type III, alpha 1 | Uterus | 6.29 |
| 92642_at | CAR2 | carbonic anhydrase 2 | Uterus | 6.28 |
| 103278_at | PDI4 | peptidyl arginine deiminase, type IV | Uterus | 6.23 |
| 101542_f_at | DDX3 | DEAD (aspartate-glutamate-alanine-aspartate) box polypeptide 3 | Uterus | 6.23 |
| 93793_at | LASP1 | LIM and SH3 protein 1 | Uterus | 6.17 |
| 94817_at | SERPINH1 | serine (or cysteine) proteinase inhibitor, clade H (heat shock protein 47), member 1 | Uterus | 6.06 |
| 99569_at | KRT2-18 | keratin complex 2, basic, gene 18 | Uterus | 6.04 |
| 95705_s_at | ACTX | melanoma X-actin | Uterus | 5.94 |
| 92368_at | RAMP3 | receptor (calcitonin) activity modifying protein 3 | Uterus | 5.93 |
| 102292_at | GADD45A | growth arrest and DNA-damage-inducible 45 alpha | Uterus | 5.93 |
| 94384_at | IER3 | immediate early response 3 | Uterus | 5.84 |
| 103438_at | DIO2 | deiodinase, iodothyronine, type II | Uterus | 5.83 |
| 97882_at | SEC61A | SEC61, alpha subunit (*S. cerevisiae*) | Uterus | 5.81 |
| 93574_at | PEDF | pigment epithelium-derived factor | Uterus | 5.81 |
| 99622_at | KLF4 | Kruppel-like factor 4 (gut) | Uterus | 5.74 |
| 100981_at | IFIT1 | interferon-induced protein with tetratricopeptide repeats 1 | Uterus | 5.74 |
| 99645_at | UNK_AW048484 | Cluster Incl AW048484: UI-M-BH1-alj-d-10-0-UI.s1 *Mus musculus* cDNA, 3' end/clone = UI-M-BH1-alj-d-10-0-UI/clone_end = 3'/gb = AW048484/gi = 5909018/ug = Mm.43640/len = 458/STRA = for | Uterus | 5.67 |
| 95444_at | UNK_AW122274 | ESTs, Weakly similar to CG1534 gene product [*D. melanogaster*] | Uterus | 5.67 |
| 99931_at | LAMA5 | laminin, alpha 5 | Uterus | 5.66 |
| 100130_at | JUN | Jun oncogene | Uterus | 5.64 |
| 100618_f_at | SLC25A5 | solute carrier family 25 (mitochondrial carrier; adenine nucleotide translocator), member 5 | Uterus | 5.64 |
| 101929_at | UNK_AI836322 | Cluster Incl AI836322: UI-M-AQ0-aag-a-02-0-UI.s2 *Mus musculus* cDNA, 3' end/clone = UI-M-AQ0-aag-a-02-0-UI/clone_end = 3'/gb = AI836322/gi = 5470530/ug = Mm.939/len = 211/STRA = for | Uterus | 5.63 |
| 100609_at | UNK_AF049850 | Cluster Incl AF049850: *Mus musculus* major histocompatibility locus class III region-complement C4 (C4) and cytochrome P450 hydroxylase A (CYP21OH-A) genes, complete cds; slp pseudogene, complete sequence; NG6, SKI, and complement factor B (Bf) genes, comp | Uterus | 5.58 |
| 95637_at | UNK_AI838592 | ESTs, Moderately similar to ENDOTHELIAL ACTIN-BINDING PROTEIN [*Homo sapiens*] | Uterus | 5.46 |
| 101367_at | DCTN1 | dynactin 1 | Uterus | 5.42 |
| 101681_f_at | H2-BL | histocompatibility 2, blastocyst | Uterus | 5.24 |
| 100557_g_at | UNK_AW121930 | ESTs, Highly similar to EUKARYOTIC INITIATION FACTOR 4B [*Homo sapiens*] | Uterus | 5.21 |
| 93985_at | UNK_AW120868 | ESTs, Highly similar to hypothetical protein [*H. sapiens*] | Uterus | 5.18 |
| 92851_at | CP | ceruloplasmin | Uterus | 5.14 |
| 99109_at | IER2 | immediate early response 2 | Uterus | 5.13 |
| 99632_at | MAD2L1 | MAD2 (mitotic arrest deficient, homolog)-like 1 (yeast) | Uterus | 5.13 |
| 94307_at | FBLN1 | fibulin 1 | Uterus | 5.1 |
| 92232_at | CISH3 | cytokine inducible SH2-containing protein 3 | Uterus | 5.09 |
| 92611_at | GPIAP-PENDING | GPI-anchored membrane protein 1 | Uterus | 5.07 |
| 104333_at | D17H6S56E-5 | DNA segment, Chr 17, human D6S56E 5 | Uterus | 5.07 |
| 101016_at | ARF1 | ADP-ribosylation factor 1 | Uterus | 5.06 |
| 103460_at | UNK_AI849939 | ESTs, Moderately similar to unnamed protein product [*H. sapiens*] | Uterus | 5.05 |
| 94309_g_at | FBLN1 | fibulin 1 | Uterus | 4.95 |
| 99927_at | CFI | complement component factor I | Uterus | 4.94 |
| 96278_at | UNK_AI846553 | ESTs, Weakly similar to DIA1_MOUSE DIAPHANOUS PROTEIN HOMOLOG 1 [*M. musculus*] | Uterus | 4.84 |

TABLE III-continued

Genes Regulated By Estrogen in the Uterus

| Mousedata.Qualifier | Pub_Name | Gene Name | Tissue | Mean WT E2 Fold Change |
|---|---|---|---|---|
| 103345_at | UNK_AW046708 | ESTs, Highly similar to SPECTRIN ALPHA CHAIN, NON-ERYTHROID [Rattus norvegicus] | Uterus | 4.83 |
| 95794_f_at | SPRR2I | small proline-rich protein 2I | Uterus | 4.83 |
| 101908_s_at | CEACAM2 | CEA-related cell adhesion molecule 2 | Uterus | 4.8 |
| 104144_at | GTPBP2 | GTP binding protein 2 | Uterus | 4.8 |
| 102362_i_at | JUNB | Jun-B oncogene | Uterus | 4.79 |
| AFFX-GapdhMur/M32599_M_at | GAPDHM_Mm_AFFX | Glyceraldehyde-3-phospate dehydrogenase middle control sequence (M. musculus) [AFFX] | Uterus | 4.79 |
| AFFX-GapdhMur/M32599_M_at | GAPDHM_Mm_AFFX | Glyceraldehyde-3-phospate dehydrogenase middle control sequence (M. musculus) [AFFX] | Uterus | 4.79 |
| AFFX-GapdhMur/M32599_M_at | GAPDHM_Mm_AFFX | Glyceraldehyde-3-phospate dehydrogenase middle control sequence (M. musculus) [AFFX] | Uterus | 4.79 |
| 94246_at | ETS2 | E26 avian leukemia oncogene 2, 3' domain | Uterus | 4.78 |
| 98930_at | COPE | coatomer protein complex, subunit epsilon | Uterus | 4.76 |
| 98928_at | CORO1B | coronin, actin binding protein 1B | Uterus | 4.76 |
| 94821_at | XBP1 | X-box binding protein 1 | Uterus | 4.69 |
| 95708_at | D3UCLA1 | DNA segment, Chr 3, University of California at Los Angeles 1 | Uterus | 4.66 |
| 96284_at | UNK_AW121446 | ESTs, Moderately similar to CASEIN KINASE I, GAMMA ISOFORM [Bos taurus] | Uterus | 4.64 |
| 104279_at | UNK_AW125116 | ESTs, Highly similar to DNA-DIRECTED RNA POLYMERASE II 14.4 KD POLYPEPTIDE [Homo sapiens; Cricetulus griseus] | Uterus | 4.62 |
| 93541_at | TAGLN | transgelin | Uterus | 4.62 |
| 93798_at | LDH1 | lactate dehydrogenase 1, A chain | Uterus | 4.61 |
| 99926_at | PIGR | polymeric immunoglobulin receptor | Uterus | 4.61 |
| 99338_at | UNK_AA674798 | ESTs, Highly similar to TIP120 [R. norvegicus] | Uterus | 4.6 |
| 93066_at | GRN | granulin | Uterus | 4.6 |
| 99366_at | UNK_AI553536 | Cluster Incl AI553536: vw39e06.x1 Mus musculus cDNA, 3' end/clone = IMAGE-1246210/clone_end = 3'/gb = AI553536/gi = 4485899/ug = Mm.5675/len = 408/STRA = rev | Uterus | 4.58 |
| 103556_at | UNK_AI840158 | Cluster Incl AI840158: UI-M-AO0-acc-d-08-0-UI.s1 Mus musculus cDNA, 3' end/clone = UI-M-AO0-acc-d-08-0-UI/clone_end = 3'/gb = AI840158/gi = 5474371/ug = Mm.19081/len = 406/STRA = for | Uterus | 4.55 |
| 101095_at | MFAP2 | microfibrillar-associated protein 2 | Uterus | 4.53 |
| 100323_at | AMD2 | S-adenosylmethionine decarboxylase 2 | Uterus | 4.5 |
| 102161_f_at | H2-Q2 | histocompatibility 2, Q region locus 2 | Uterus | 4.5 |
| 101955_at | HSPA5 | heat shock 70 kD protein 5 (glucose-regulated protein, 78 kD) | Uterus | 4.49 |
| 95654_at | UNK_AF109905 | Cluster Incl AF109905: Mus musculus major histocompatibility locus class III regions Hsc70t gene, partial cds; smRNP, G7A, NG23, MutS homolog, CLCP, NG24, NG25, and NG26 genes, complete cds; and unknown genes/cds = (0,725)/gb = AF109905/gi = 3986751/ug = Mm.29 | Uterus | 4.49 |
| 98107_at | UNK_AW123801 | Cluster Incl AW123801: UI-M-BH2.1-apm-e-08-0-UI.s1 Mus musculus cDNA, 3' end/clone = UI-M-BH2.1-apm-e-08-0-UI/clone_end = 3'/gb = AW123801/gi = 6099331/ug = Mm.34796/len = 367/STRA = for | Uterus | 4.48 |
| 92925_at | CEBPB | CCAAT/enhancer binding protein (C/EBP), beta | Uterus | 4.47 |
| 92625_at | NME2 | expressed in non-metastatic cells 2, protein (NM23B) (nucleoside diphosphate kinase) | Uterus | 4.46 |
| 96283_at | ITM3-PENDING | integral membrane protein 3 | Uterus | 4.43 |
| 97809_at | UNK_AF109906 | Cluster Incl AF109906: Mus musculus MHC class III region RD gene, partial cds; Bf, C2, G9A, NG22, G9, HSP70, HSP70, HSC70t, and smRNP genes, complete cds; G7A gene, partial cds; and unknown genes/cds = (0,3002)/gb = AF109906/gi = 3986763/ug = Mm.28155/len = 300 | Uterus | 4.4 |
| 103709_at | UNK_AA763466 | Cluster Incl AA763466: vw54f05.r1 Mus musculus cDNA, 5' end/clone = IMAGE-1247649/clone_end = 5'/gb = AA763466/gi = 2813213/ug = Mm.24093/len = 379/STRA = for | Uterus | 4.37 |
| 98562_at | C1QA | complement component 1, q subcomponent, alpha polypeptide | Uterus | 4.37 |
| 92644_s_at | MYB | myeloblastosis oncogene | Uterus | 4.37 |
| 99624_at | RPL5 | ribosomal protein L5 | Uterus | 4.33 |
| 104093_at | LSP1 | lymphocyte specific 1 | Uterus | 4.31 |
| 99942_s_at | CNN1 | calponin 1 | Uterus | 4.31 |
| 101055_at | PPGB | protective protein for beta-galactosidase | Uterus | 4.3 |
| 100059_at | CYBA | cytochrome b-245, alpha polypeptide | Uterus | 4.29 |
| 94868_at | UNK_AW049812 | ESTs, Highly similar to GLUTAMINYL-TRNA SYNTHETASE [Homo sapiens] | Uterus | 4.28 |
| 93751_at | UNK_AW048157 | ESTs, Highly similar to PROBABLE UBIQUITIN CARBOXYL-TERMINAL HYDROLASE [Mus musculus] | Uterus | 4.27 |
| 101061_at | UNK_AI845293 | ESTs, Highly similar to TRANSLOCON-ASSOCIATED PROTEIN, BETA SUBUNIT PRECURSOR [Homo sapiens] | Uterus | 4.26 |

TABLE III-continued

Genes Regulated By Estrogen in the Uterus

| Mousedata. Qualifier | Pub_Name | Gene Name | Tissue | Mean WT E2 Fold Change |
|---|---|---|---|---|
| 101916_at | DHCR7 | 7-dehydrocholesterol reductase | Uterus | 4.25 |
| 93327_at | UNK_AI842665 | ESTs, Highly similar to HYPOTHETICAL 13.5 KD PROTEIN C45G9.7 IN CHROMOSOME III [*Caenorhabditis elegans*] | Uterus | 4.25 |
| 102968_at | GGTLA1 | gamma-glutamyltransferase-like activity 1 | Uterus | 4.24 |
| 99106_at | COPS6 | COP9 (constitutive photomorphogenic), subunit 6 (*Arabidopsis*) | Uterus | 4.22 |
| 97160_at | SPARC | secreted acidic cysteine rich glycoprotein | Uterus | 4.22 |
| 96943_at | UNK_AW125234 | ESTs, Highly similar to FUSCA PROTEIN FUS6 [*Arabidopsis thaliana*] | Uterus | 4.2 |
| 97320_at | UNK_AI842734 | ESTs, Weakly similar to KE4_MOUSE HISTIDINE-RICH PROTEIN KE4□ [*M. musculus*] | Uterus | 4.18 |
| 96353_at | UNK_AW125346 | ESTs, Moderately similar to AF151028_1 HSPC194 [*H. sapiens*] | Uterus | 4.17 |
| 94854_g_at | GNB1 | guanine nucleotide binding protein, beta 1 | Uterus | 4.15 |
| 97894_at | UNK_AF109905 | Cluster Incl AF109905: *Mus musculus* major histocompatibility locus class III regions Hsc70t gene, partial cds; smRNP, G7A, NG23, MutS homolog, CLCP, NG24, NG25, and NG26 genes, complete cds; and unknown genes/cds = (0,3791)/ gb = AF109905/gi = 3986751/ug = Mm.2 | Uterus | 4.14 |
| 93390_g_at | PROM | prominin | Uterus | 4.13 |
| 103429_i_at | UNK_AW125330 | ESTs, Moderately similar to unnamed protein product [*H. sapiens*] | Uterus | 4.1 |
| 96186_at | UNK_AI839286 | ESTs, Moderately similar to Unknown [*H. sapiens*] | Uterus | 4.09 |
| 103335_at | LGALS9 | lectin, galactose binding, soluble 9 | Uterus | 4.07 |
| 101393_at | ANXA3 | annexin A3 | Uterus | 4.07 |
| 93389_at | PROM | prominin | Uterus | 4.06 |
| 103888_at | RBPMS | RNA-blnding protein gene with multiple splicing | Uterus | 4.06 |
| 96258_at | D13ERTD372E | DNA segment, Chr 13, ERATO Doi 372, expressed | Uterus | 4.03 |
| 95161_at | D10ERTD73E | DNA segment, Chr 10, ERATO Doi 73, expressed | Uterus | 4.03 |
| 96869_at | GABARAP | gamma-aminobutyric acid receptor associated protein | Uterus | 4.02 |
| 101558_s_at | PSMB5 | proteasome (prosome, macropain) subunit, beta type 5 | Uterus | 4 |
| 96883_at | EIF3S4 | eukaryotic translation initiation factor 3, subunit 4 (delta, 44 kDa) | Uterus | 3.98 |
| 99549_at | OGN | osteoglycin | Uterus | 3.95 |
| 101781_f_at | UNK_V00754 | HISTONE H3.4 | Uterus | 3.95 |
| 93975_at | 33 POLYPEPTIDE□ [*R. NORVEGICUS*] | ESTs, Highly similar to G33_RAT GENE 33 POLYPEPTIDE□ [*R. norvegicus*] | Uterus | 3.91 |
| 92930_at | DLX5 | distal-less homeobox 5 | Uterus | 3.91 |
| 95462_at | UNK_AW060951 | ESTs, Highly similar to unknown [*R. norvegicus*] | Uterus | 3.9 |
| 102791_at | PSMB8 | proteosome (prosome, macropain) subunit, beta type 8 (large multifunctional protease 7) | Uterus | 3.89 |
| 95215_f_at | UBC | ubiquitin C | Uterus | 3.89 |
| 92850_at | UNK_AI836446 | ESTs, Moderately similar to KIAA1398 protein [*H. sapiens*] | Uterus | 3.88 |
| 100332_s_at | PRDX5-RS3 | peroxiredoxin 5, related sequence 3 | Uterus | 3.87 |
| 100561_at | IQGAP1 | IQ motif containing GTPase activating protein 1 | Uterus | 3.84 |
| 98446_s_at | EPHB4 | Eph receptor B4 | Uterus | 3.82 |
| 100771_at | LY57 | lymphocyte antigen 57 | Uterus | 3.81 |
| 103547_at | UNK_AI837116 | Cluster Incl AI837116: UI-M-AK0-adc-e-09-0-UI.s1 *Mus musculus* cDNA, 3' end/clone = UI-M-AK0-adc-e-09-0-UI/ clone_end = 3'/gb = AI837116/gi = 5471329/ug = Mm.23723/ len = 323/STRA = rev | Uterus | 3.81 |
| 104365_at | SCAMP2 | secretory carrier membrane protein 2 | Uterus | 3.8 |
| 93496_at | UNK_AI852098 | ESTs, Weakly similar to AF104033_1 MUEL protein [*M. musculus*] | Uterus | 3.79 |
| 100970_at | AKT | thymoma viral proto-oncogene | Uterus | 3.79 |
| 96318_at | D17WSU104E | DNA segment, Chr 17, Wayne State University 104, expressed | Uterus | 3.78 |
| 93430_at | CMKOR1 | chemokine orphan receptor 1 | Uterus | 3.75 |
| 92882_at | RAB1 | RAB1, member RAS oncogene family | Uterus | 3.74 |
| 97824_at | D11ERTD175E | DNA segment, Chr 11, ERATO Doi 175, expressed | Uterus | 3.72 |
| 99991_at | IL17R | interleukin 17 receptor | Uterus | 3.72 |
| 100684_at | PRKCSH | protein kinase C substrate 80K-H | Uterus | 3.72 |
| 96935_at | UNK_AW011791 | ESTs, Moderately similar to epithelial protein up-regulated in carcinoma [*H. sapiens*] | Uterus | 3.71 |
| 93500_at | ALAS1 | aminolevulinic acid synthase 1 | Uterus | 3.69 |
| 100554_at | PDLIM1 | PDZ and LIM domain 1 (elfin) | Uterus | 3.67 |
| 94105_at | CDC42 | cell division cycle 42 homolog (*S. cerevisiae*) | Uterus | 3.66 |
| 101486_at | PSMB10 | proteasome (prosome, macropain) subunit, beta type 10 | Uterus | 3.66 |
| 96155_at | UNK_AW049359 | ESTs, Highly similar to AF177476_1 CDK5 activator-binding protein [*R. norvegicus*] | Uterus | 3.65 |
| 99475_at | CISH2 | cytokine inducible SH2-containing protein 2 | Uterus | 3.64 |
| 102767_at | AA536815 | EST AA536815 | Uterus | 3.64 |
| 104315_at | UNK_AI846773 | Cluster Incl AI846773: UI-M-AO1-ael-f-02-0-UI.s1 *Mus musculus* cDNA, 3' end/clone = UI-M-AO1-ael-f-02-0-UI/ clone_end = 3'/gb = AI846773/gi = 5490679/ug = Mm.22413/ len = 322/STRA = for | Uterus | 3.64 |

TABLE III-continued

Genes Regulated By Estrogen in the Uterus

| Mousedata.Qualifier | Pub_Name | Gene Name | Tissue | Mean WT E2 Fold Change |
|---|---|---|---|---|
| 104389_at | UNK_AW049360 | ESTs, Weakly similar to T17295 hypothetical protein DKFZp434H132.1 - human [*H. sapiens*] | Uterus | 3.63 |
| 93833_s_at | UNK_X05862 | Cluster Incl X05862: Mouse H2B and H2A histone genes (291A)/cds = (0,380)/gb = X05862/gi = 51302/ug = Mm.21579/ len = 381/STRA = for | Uterus | 3.61 |
| 101881_g_at | COL18A1 | procollagen, type XVIII, alpha 1 | Uterus | 3.61 |
| 100569_at | ANXA2 | annexin A2 | Uterus | 3.6 |
| 94561_at | UNK_AI836140 | *Mus musculus* epithelial protein lost in neoplasm-a (Eplin) mRNA, complete cds | Uterus | 3.59 |
| 95608_at | CTSB | cathepsin B | Uterus | 3.57 |
| 96709_at | UNK_AI839839 | ESTs, Highly similar to EST00098 protein [*H. sapiens*] | Uterus | 3.57 |
| 93102_f_at | ACTG2 | actin, gamma 2, smooth muscle, enteric | Uterus | 3.55 |
| 99477_at | GNG12 | guanine nucleotide binding protein (G protein), gamma 12 | Uterus | 3.55 |
| 94237_at | D6WSU137E | DNA segment, Chr 6, Wayne State University 137, expressed | Uterus | 3.55 |
| 98937_at | TBRG1 | transforming growth factor beta regulated gene 1 | Uterus | 3.53 |
| 94503_at | UNK_AI842492 | ESTs, Highly similar to RAS-RELATED PROTEIN RAB-8 [*Homo sapiens*; *Canis familiaris*] | Uterus | 3.5 |
| 99019_at | POR | P450 (cytochrome) oxidoreductase | Uterus | 3.49 |
| 104623_at | TLE3 | transducin-like enhancer of split 3, homolog of *Drosophila* E(spl) | Uterus | 3.47 |
| 92866_at | H2-AA | histocompatibility 2, class II antigen A, alpha | Uterus | 3.46 |
| 103200_at | UNK_AA711773 | Cluster Incl AA711773: vu58g05.r1 *Mus musculus* cDNA, 5' end/ clone = IMAGE-1195640/clone_end = 5'/gb = AA711773/ gi = 2721691/ug = Mm.1902/len = 473/STRA = for | Uterus | 3.44 |
| 104100_at | UNK_AI845915 | Cluster Incl AI845915: UI-M-AK1-aex-d-02-0-UI.s1 *Mus musculus* cDNA, 3' end/clone = UI-M-AK1-aex-d-02-0-UI/ clone_end = 3'/gb = AI845915/gi = 5489821/ug = Mm.21864/ len = 208/STRA = for | Uterus | 3.42 |
| 94063_at | SEMA4A | sema domain, immunoglobulin domain (Ig), transmembrane domain (TM) and short cytoplasmic domain, (semaphorin) 4A | Uterus | 3.42 |
| 95752_at | UNK_AI837369 | ESTs, Highly similar to unnamed protein product [*H. sapiens*] | Uterus | 3.42 |
| 97409_at | IFI1 | interferon inducible protein 1 | Uterus | 3.41 |
| 95749_at | UNK_AW122364 | ESTs, Highly similar to ARGR_HUMAN ARGININE-RICH PROTEIN☐ [*H. sapiens*] | Uterus | 3.41 |
| 104110_at | UNK_AW060515 | Cluster Incl AW060515: UI-M-BH1-ann-d-07-0-UI.s1 *Mus musculus* cDNA, 3' end/clone = UI-M-BH1-ann-d-07-0-UI/ clone_end = 3'/gb = AW060515/gi = 6008266/ug = Mm.21919/ len = 330/STRA = for | Uterus | 3.39 |
| 99101_at | EIF3S7 | eIF3 p66 | Uterus | 3.39 |
| 94966_at | G6PDX | glucose-6-phosphate dehydrogenase X-linked | Uterus | 3.38 |
| 92567_at | COL5A2 | procollagen, type V, alpha 2 | Uterus | 3.37 |
| 103016_s_at | CD68 | CD68 antigen | Uterus | 3.36 |
| AFFX-b-ActinMur/M 12481_3_at | BACTIN3_Mm_AFFX | Beta-actin 3' control sequence (*M. musculus*) [AFFX] | Uterus | 3.35 |
| AFFX-b-ActinMur/M 12481_3_at | BACTIN3_Mm_AFFX | Beta-actin 3' control sequence (*M. musculus*) [AFFX] | Uterus | 3.35 |
| AFFX-b-ActinMur/M 12481_3_at | BACTIN3_Mm_AFFX | Beta-actin 3' control sequence (*M. musculus*) [AFFX] | Uterus | 3.35 |
| 96653_at | APP | amyloid beta (A4) precursor protein | Uterus | 3.35 |
| 99872_s_at | FTL1 | ferritin light chain 1 | Uterus | 3.34 |
| 97125_f_at | LOC56628 | MHC (A.CA/J(H-2K-f) class I antigen | Uterus | 3.33 |
| 94288_at | HIS1A | histone H1 | Uterus | 3.32 |
| 93276_at | HN1 | hematological and neurological expressed sequence 1 | Uterus | 3.29 |
| 93071_at | TIF1B | transcriptional intermediary factor 1, beta | Uterus | 3.28 |
| 99032_at | RASD1 | RAS, dexamethasone-induced 1 | Uterus | 3.27 |
| 100428_at | LAMC2 | laminin, gamma 2 | Uterus | 3.25 |
| 103708_at | UNK_AI132207 | Cluster Incl AI132207: ue28g02.x1 *Mus musculus* cDNA, 3' end/ clone = IMAGE-1481714/clone_end = 3'/gb = AI132207/ gi = 3602223/ug = Mm.24090/len = 450/STRA = for | Uterus | 3.23 |
| 96693_at | UNK_AI849453 | ESTs, Highly similar to ARGINYL-TRNA SYNTHETASE [*Cricetulus longicaudatus*] | Uterus | 3.23 |
| 94831_at | CTSB | cathepsin B | Uterus | 3.2 |
| 95493_at | COL6A1 | procollagen, type VI, alpha 1 | Uterus | 3.2 |
| 99562_at | MAN2B1 | mannosidase 2, alpha B1 | Uterus | 3.2 |
| 101487_f_at | LY6E | lymphocyte antigen 6 complex, locus E | Uterus | 3.18 |
| 100081_at | STIP1 | stress-induced phosphoprotein 1 | Uterus | 3.18 |
| 94061_at | CRIP | cysteine rich intestinal protein | Uterus | 3.18 |
| 101060_at | GRP58 | glucose regulated protein, 58 kDa | Uterus | 3.16 |
| 98522_at | PSMD8 | proteasome (prosome, macropain) 26S subunit, non-ATPase, 8 | Uterus | 3.16 |
| 101834_at | MAPK3 | mitogen activated protein kinase 3 | Uterus | 3.14 |
| 96657_at | SAT | spermidine/spermine N1-acetyl transferase | Uterus | 3.14 |

TABLE III-continued

Genes Regulated By Estrogen in the Uterus

| Mousedata. Qualifier | Pub_Name | Gene Name | Tissue | Mean WT E2 Fold Change |
|---|---|---|---|---|
| 92632_at | UNK_AI842328 | *Mus musculus* calmodulin III (Calm3) mRNA, 3' untranslated region | Uterus | 3.12 |
| 99992_at | UNK_AI286698 | ESTs, Highly similar to interleukin 17 receptor□ [*M. musculus*] | Uterus | 3.12 |
| 94282_at | ASAH1 | N-acylsphingosine amidohydrolase 1 | Uterus | 3.11 |
| 94788_f_at | TUBB5 | tubulin, beta 5 | Uterus | 3.11 |
| 103398_at | UNK_AW123232 | Cluster Incl AW123232: UI-M-BH2.1-apd-g-08-0-UI.s1 *Mus musculus* cDNA, 3' end/clone = UI-M-BH2.1-apd-g-08-0-UI/ clone_end = 3'/gb = AW123232/gi = 6098727/ug = Mm.18714/ len = 469/STRA = rev | Uterus | 3.1 |
| 95149_at | COPZ1 | coatomer protein complex, subunit zeta 1 | Uterus | 3.1 |
| 103891_i_at | UNK_AI197161 | ESTs, Moderately similar to ELL2_HUMAN RNA POLYMERASE II ELONGATION FACTOR ELL2□ [*H. sapiens*] | Uterus | 3.09 |
| 98104_at | UNK_AI842889 | ESTs, Highly similar to PROTEOLIPID PROTEIN PPA1 [*Saccharomyces cerevisiae*] | Uterus | 3.08 |
| 102916_s_at | CREBL1 | cAMP responsive element binding protein-like 1 | Uterus | 3.08 |
| 101591_at | UNK_AI852589 | ESTs, Highly similar to HYPOTHETICAL PROTEIN C22G7.01C IN CHROMOSOME I [*Schizosaccharomyces pombe*] | Uterus | 3.07 |
| 100949_at | UNK_AI461767 | ESTs, Weakly similar to hypothetical protein [*H. sapiens*] | Uterus | 3.05 |
| 96573_at | ACTG | actin, gamma, cytoplasmic | Uterus | 3.04 |
| 100948_at | D15ERTD221E | DNA segment, Chr 15, ERATO Doi 221, expressed | Uterus | 3.03 |
| 101754_f_at | SPRR2G | small proline-rich protein 2G | Uterus | 3.02 |
| 97829_at | UNK_AI838053 | ESTs, Highly similar to phosphatidylinositol synthase [*R. norvegicus*] | Uterus | 3.02 |
| 101886_f_at | H2-L | histocompatibility 2, L region | Uterus | 3.01 |
| 99067_at | GAS6 | growth arrest specific 6 | Uterus | 3 |
| 101571_g_at | IGFBP4 | insulin-like growth factor binding protein 4 | Uterus | 3 |
| 100998_at | H2-AB1 | histocompatibility 2, class II antigen A, beta 1 | Uterus | 3 |
| 96135_at | UNK_AA833425 | ESTs, Highly similar to AF161398_1 HSPC280 [*H. sapiens*] | Uterus | 2.99 |
| 101105_at | BCRP1-PENDING | breakpoint cluster region protein 1 | Uterus | 2.97 |
| 96024_at | AHCY | S-adenosylhomocysteine hydrolase | Uterus | 2.96 |
| 100496_at | PAM | peptidylglycine alpha-amidating monooxygenase | Uterus | 2.95 |
| 103755_at | SH3D19 | SH3 domain protein D19 | Uterus | 2.95 |
| 97817_at | SPEC1-PENDING | small protein effector 1 of Cdc42 | Uterus | 2.95 |
| 98543_at | CTSS | cathepsin S | Uterus | 2.95 |
| 93548_at | UNK_AW122942 | ESTs, Highly similar to PROTEIN TRANSPORT PROTEIN SEC61 BETA SUBUNIT [*Homo sapiens*; *Canis familiaris*] | Uterus | 2.94 |
| 97197_r_at | UNK_C78850 | Mouse (AKR/J) endogenous retrovirus, clone A-12, pol-env region | Uterus | 2.93 |
| 102370_at | UNK_AA822174 | Cluster Incl AA822174: vp36a09.r1 *Mus musculus* cDNA, 5' end/ clone = IMAGE-1078744/clone_end = 5'/gb = AA822174/ gi = 2892042/ug = Mm.1187/len = 329/STRA = for | Uterus | 2.91 |
| 97559_at | EEF2 | eukaryotic translation elongation factor 2 | Uterus | 2.9 |
| 96732_at | UNK_AI851081 | ESTs, Highly similar to T17338 hypothetical protein DKFZp434O125.1 - human [*H. sapiens*] | Uterus | 2.89 |
| 92450_at | SLC12A4 | solute carrier family 12, member 4 | Uterus | 2.88 |
| 93126_at | CKB | creatine kinase, brain | Uterus | 2.87 |
| 98417_at | MX1 | myxovirus (influenza virus) resistance 1 | Uterus | 2.87 |
| 96360_at | UNK_AW125498 | ESTs, Weakly similar to GDIS_MOUSE RHO GDP-DISSOCIATION INHIBITOR 2 [*M. musculus*] | Uterus | 2.86 |
| 96356_at | AF007010 | EST AF007010 | Uterus | 2.84 |
| 95593_at | UNK_AW125446 | Cluster Incl AW125446: UI-M-BH2.3-aqh-h-05-0-UI.s1 *Mus musculus* cDNA, 3' end/clone = UI-M-BH2.3-aqh-h-05-0-UI/ clone_end = 3'/gb = AW125446/gi = 6100976/ug = Mm.27902/ len = 540/STRA = for | Uterus | 2.84 |
| 98405_at | SPI6 | serine protease inhibitor 6 | Uterus | 2.84 |
| 102804_at | CEACAM1 | CEA-related cell adhesion molecule 1 | Uterus | 2.83 |
| 92836_at | UNK_AA919594 | Cluster Incl AA919594: vz22b07.r1 *Mus musculus* cDNA, 5' end/ clone = IMAGE-1316437/clone_end = 5'/gb = AA919594/ gi = 3066373/ug = Mm.13097/len = 222/STRA = for | Uterus | 2.83 |
| 100460_at | TSBP | TPR-containing, SH2-binding phosphoprotein | Uterus | 2.83 |
| 100094_at | SUPT5H | suppressor of Ty 5 homolog (*S. cerevisiae*) | Uterus | 2.82 |
| 100064_f_at | GJA1 | gap junction membrane channel protein alpha 1 | Uterus | 2.81 |
| 96632_at | MRGX-PENDING | MORF-related gene X | Uterus | 2.81 |
| 95721_at | MAPKAPK2 | MAP kinase-activated protein kinase 2 | Uterus | 2.8 |
| 101948_at | LAMB1-1 | laminin B1 subunit 1 | Uterus | 2.8 |
| 101959_r_at | TFDP1 | transcription factor Dp 1 | Uterus | 2.79 |
| 97203_at | MLP | MARCKS-like protein | Uterus | 2.77 |
| 97496_f_at | UNK_AW048944 | ESTs, Weakly similar to polymerase I-transcript release factor [*M. musculus*] | Uterus | 2.76 |
| 101877_at | SLC31A1 | solute carrier family 31, member 1 | Uterus | 2.76 |
| 104221_at | SLC7A5 | solute carrier family 7 (cationic amino acid transporter, y+ system), member 5 | Uterus | 2.75 |
| 98019_at | TGFB1I1 | transforming growth factor beta 1 induced transcript 1 | Uterus | 2.75 |

TABLE III-continued

Genes Regulated By Estrogen in the Uterus

| Mousedata.Qualifier | Pub_Name | Gene Name | Tissue | Mean WT E2 Fold Change |
|---|---|---|---|---|
| 101510_at | PSME1 | protease (prosome, macropain) 28 subunit, alpha | Uterus | 2.74 |
| 96340_at | UNK_AW124185 | ESTs, Highly similar to C214_HUMAN 17.9 KDA MEMBRANE PROTEIN C21ORF4□ [*H. sapiens*] | Uterus | 2.74 |
| 96761_at | UNK_AF109906 | Cluster Incl AF109906: *Mus musculus* MHC class III region RD gene, partial cds; Bf, C2, G9A, NG22, G9, HSP70, HSP70, HSC70t, and smRNP genes, complete cds; G7A gene, partial cds; and unknown genes/cds = (0,2123)/gb = AF109906/gi = 3986763/ug = Mm.29004/len = 212 | Uterus | 2.72 |
| 102990_at | COL3A1 | procollagen, type III, alpha 1 | Uterus | 2.72 |
| 94224_s_at | UNK_M74123 | *Mus musculus* (strain C57BI/6) mRNA sequence | Uterus | 2.71 |
| 100621_at | UNK_AI848825 | ESTs, Highly similar to RIBONUCLEASE INHIBITOR [*Rattus norvegicus*] | Uterus | 2.7 |
| 102752_at | SHYC | selective hybridizing clone | Uterus | 2.7 |
| 97013_f_at | CYBA | cytochrome b-245, alpha polypeptide | Uterus | 2.68 |
| 104248_at | UNK_AW227650 | ESTs, Highly similar to TRANSLOCON-ASSOCIATED PROTEIN, GAMMA SUBUNIT [*Rattus norvegicus*] | Uterus | 2.68 |
| 104701_at | STRA14 | stimulated by retinoic acid 14 | Uterus | 2.68 |
| 103648_at | TACSTD2 | tumor-associated calcium signal transducer 2 | Uterus | 2.67 |
| 99514_at | UNK_AI835443 | ESTs, Highly similar to B-MYC TRANSFORMING PROTEIN [*Rattus norvegicus*] | Uterus | 2.67 |
| 97262_at | UNK_AW050305 | ESTs, Highly similar to CASEIN KINASE I, DELTA ISOFORM [*Homo sapiens*] | Uterus | 2.66 |
| 95694_at | UNK_X70956 | *M. musculus* TOP gene for topoisomerase I, exons 19-21 | Uterus | 2.66 |
| 101078_at | BSG | basigin | Uterus | 2.64 |
| 95660_at | UNK_AI851815 | *Mus musculus* HSCO mRNA, complete cds | Uterus | 2.63 |
| 99993_at | ANPEP | alanyl (membrane) aminopeptidase (aminopeptidase N, aminopeptidase M, microsomal aminopeptidase, CD13, p150) | Uterus | 2.63 |
| 103494_at | UNK_AI047972 | ESTs, Weakly similar to CD63_MOUSE CD63 ANTIGEN□ [*M. musculus*] | Uterus | 2.63 |
| 94929_at | PTPN1 | protein tyrosine phosphatase, non-receptor type 1 | Uterus | 2.6 |
| 100610_at | CAPN4 | calpain 4 | Uterus | 2.6 |
| 97890_at | SGK | serum/glucocorticoid regulated kinase | Uterus | 2.6 |
| 100889_at | UNK_AI838576 | Cluster Incl AI838576: UI-M-AO0-abz-c-02-0-UI.s1 *Mus musculus* cDNA, 3' end/clone = UI-M-AO0-abz-c-02-0-UI/clone_end = 3'/gb = AI838576/gi = 5472789/ug = Mm.54120/len = 181/STRA = rev | | |
| 100475_at | ZFP147 | zinc finger protein 147 | Uterus | 2.59 |
| 98946_at | WSB1 | WSB-1 | Uterus | 2.59 |
| 96912_s_at | CTLA2A | cytotoxic T lymphocyte-associated protein 2 alpha | Uterus | 2.58 |
| 96069_at | UNK_AI840094 | ESTs, Highly similar to AFLATOXIN B1 ALDEHYDE REDUCTASE [*Rattus norvegicus*] | Uterus | 2.57 |
| 100723_f_at | SPRR2E | small proline-rich protein 2E | Uterus | 2.57 |
| 93058_at | EIF1A | eukaryotic translation initiation factor 1A | Uterus | 2.56 |
| 94301_at | ATP6K | ATPase, H+ transporting lysosomal (vacuolar proton pump), 9.2 kDa | Uterus | 2.55 |
| 93680_at | STK10 | serine/threonine kinase 10 | Uterus | 2.55 |
| 93499_at | CAPPA1 | capping protein alpha 1 | Uterus | 2.55 |
| 100422_i_at | UNK_AJ237939 | Cluster Incl AJ237939: *Mus musculus* partial STAT5B gene, exons 6-9/cds = (0,618)/gb = AJ237939/gi = 5689871/ug = Mm.4697/len = 619/STRA = for | Uterus | 2.53 |
| 96333_g_at | UNK_AW259199 | ESTs, Weakly similar to AF154120_1 sorting nexin 1 [*M. musculus*] | Uterus | 2.53 |
| 103918_at | SLC15A2 | solute carrier family 15 (H+/peptide transporter), member 2 | Uterus | 2.53 |
| 101982_at | VASP | vasodilator-stimulated phosphoprotein | Uterus | 2.53 |
| 104155_f_at | ATF3 | activating transcription factor 3 | Uterus | 2.53 |
| 96633_s_at | MRGX-PENDING | MORF-related gene X | Uterus | 2.52 |
| 95397_at | UNK_AI852661 | Cluster Incl AI852661: UI-M-BH0-aji-a-10-0-UI.s1 *Mus musculus* cDNA, 3' end/clone = UI-M-BH0-aji-a-10-0-UI/clone_end = 3'/gb = AI852661/gi = 5496567/ug = Mm.2388/len = 297/STRA = for | Uterus | 2.5 |
| 92809_r_at | FKBP4 | FK506 binding protein 4 (59 kDa) | Uterus | 2.5 |
| 100136_at | LAMP2 | lysosomal membrane glycoprotein 2 | Uterus | 2.5 |
| 93250_r_at | HMGB2 | high mobility group box 2 | Uterus | 2.48 |
| 103551_at | AI428202 | EST AI4282022 | Uterus | 2.48 |
| 100686_at | LLREP3 | repeat family 3 gene | Uterus | 2.46 |
| 92256_at | CTSB | cathepsin B | Uterus | 2.46 |
| 92226_at | UNK_AA866971 | ESTs, Moderately similar to hypothetical protein [*H. sapiens*] | Uterus | 2.45 |
| 96056_at | ARHC | aplysia ras-related homolog 9 (RhoC) | Uterus | 2.45 |
| 96920_at | PRSS11 | insulin-like growth factor binding protein 5 protease | Uterus | 2.44 |
| 101019_at | CTSC | cathepsin C | Uterus | 2.44 |
| 100600_at | CD24A | CD24a antigen | Uterus | 2.44 |
| 94915_at | PPIB | peptidylprolyl isomerase B | Uterus | 2.44 |
| 93323_at | PLP2 | proteolipid protein 2 | Uterus | 2.43 |
| 97386_at | UNK_AI853294 | Cluster Incl AI853294: UI-M-BH0-aji-f-03-0-UI.s1 *Mus musculus* | Uterus | 2.43 |

TABLE III-continued

Genes Regulated By Estrogen in the Uterus

| Mousedata. Qualifier | Pub_Name | Gene Name | Tissue | Mean WT E2 Fold Change |
|---|---|---|---|---|
| 96939_at | TRRP2 | cDNA, 3' end/clone = UI-M-BH0-aji-f-03-0-UI/clone_end = 3'/ gb = AI853294/gi = 5497200/ug = Mm.29789/len = 413/STRA = for transient receptor protein 2 | Uterus | 2.43 |
| 95683_g_at | DDB1 | damage specific DNA binding protein 1 (127 kDa) | Uterus | 2.42 |
| 104292_at | EYA2 | eyes absent 2 homolog (*Drosphila*) | Uterus | 2.42 |
| 104300_at | IQGAP1 | IQ motif containing GTPase activating protein 1 | Uterus | 2.42 |
| 95120_at | UNK_AI837621 | ESTs, Highly similar to tetraspan NET-6 [*H. sapiens*] | Uterus | 2.41 |
| 98059_s_at | LMNA | lamin A | Uterus | 2.4 |
| 93320_at | CPT1A | carnitine palmitoyltransferase 1, liver | Uterus | 2.39 |
| 94260_at | UNK_AI850352 | ESTs, Moderately similar to KIAA0731 protein [*H. sapiens*] | Uterus | 2.39 |
| 94238_at | UNK_AW228316 | ESTs, Highly similar to serine protease [*H. sapiens*] | Uterus | 2.39 |
| 94206_at | UNK_AC002397 | Cluster Incl AC002397: Mouse chromosome 6 BAC-284H12 (Research Genetics mouse BAC library) complete sequence/ cds = (108,488)/gb = AC002397/gi = 3287367/ug = Mm.22195/ len = 568/STRA = for | | |
| 93336_at | UNK_AW121539 | ESTs, Weakly similar to ENDOSOMAL P24B PROTEIN PRECURSOR [*Saccharomyces cerevisiae*] | Uterus | 2.38 |
| 94060_at | UNK_AI852623 | ESTs, Weakly similar to Edp1 protein [*M. musculus*] | Uterus | 2.38 |
| 94834_at | CTSH | cathepsin H | Uterus | 2.37 |
| 101029_f_at | ACTC1 | actin, alpha, cardiac | Uterus | 2.37 |
| 100928_at | FBLN2 | fibulin 2 | Uterus | 2.37 |
| 92769_at | TSTAP91A | tissue specific transplantation antigen P91A | Uterus | 2.36 |
| 96829_at | D19WSU162E | DNA segment, Chr 19, Wayne State University 162, expressed | Uterus | 2.36 |
| 93309_at | FIN14 | fibroblast growth factor inducible 14 | Uterus | 2.36 |
| 101054_at | II | Ia-associated invariant chain | Uterus | 2.35 |
| 94839_at | NUCB | nucleobindin | Uterus | 2.35 |
| 98437_at | CASP3 | caspase 3, apoptosis related cysteine protease | Uterus | 2.34 |
| 98465_f_at | IFI204 | interferon activated gene 204 | Uterus | 2.33 |
| 98463_at | REGULATOR [*DROSOPHILA MELANOGASTER*] | ESTs, Highly similar to HOMEOTIC GENE REGULATOR [*Drosophila melanogaster*] | Uterus | 2.33 |
| 103399_at | SCML1 | sex comb on midleg-like 1 (*Drosophila*) | Uterus | 2.32 |
| 94327_at | UNK_AW230209 | ESTs, Moderately similar to unnamed protein product [*H. sapiens*] | Uterus | 2.31 |
| 96345_at | D2UCLA1 | DNA segment, Chr 2, University of California at Los Angeles 1 | Uterus | 2.31 |
| 97751_f_at | UNK_AI835771 | ESTs, Moderately similar to G3P_MOUSE GLYCERALDEHYDE 3-PHOSPHATE DEHYDROGENASE [*M. musculus*] | Uterus | 2.3 |
| 101047_at | VIM | vimentin | Uterus | 2.3 |
| 100772_g_at | LY57 | lymphocyte antigen 57 | Uterus | 2.3 |
| 95128_at | NCOR2 | nuclear receptor co-repressor 2 | Uterus | 2.29 |
| 93101_s_at | NEDD4 | neural precursor cell expressed, developmentally down-regulated gene 4 | Uterus | 2.29 |
| 99119_at | CFL1 | cofilin 1, non-muscle | Uterus | 2.29 |
| 103341_at | CTPS | cytidine 5'-triphosphate synthase | Uterus | 2.28 |
| 92603_at | ATP6D | ATPase, H+ transporting, lysosomal (vacuolar proton pump), 42 kDa | Uterus | 2.28 |
| 96708_at | UNK_AW120643 | ESTs, Highly similar to COP-COATED VESICLE MEMBRANE PROTEIN P24 PRECURSOR [*Cricetulus griseus*] | Uterus | 2.28 |
| 99100_at | STAT3 | signal transducer and activator of transcription 3 | Uterus | 2.28 |
| 95105_at | UNK_AI847697 | ESTs, Weakly similar to AF077034_1 HSPC010 [*H. sapiens*] | Uterus | 2.27 |
| 95142_s_at | CAPPB1 | capping protein beta 1 | Uterus | 2.27 |
| 94522_at | DCTN3 | dynactin 3 | Uterus | 2.26 |
| 98472_at | H2-T23 | histocompatibility 2, T region locus 23 | Uterus | 2.24 |
| 96025_g_at | AHCY | S-adenosylhomocysteine hydrolase | Uterus | 2.24 |
| 97689_at | F3 | coagulation factor III | Uterus | 2.23 |
| 104533_at | UNK_AA764261 | ESTs, Weakly similar to myelin transcription factor 1-like [*M. musculus*] | Uterus | 2.23 |
| 104669_at | IRF7 | interferon regulatory factor 7 | Uterus | 2.21 |
| 97885_at | 1810009M01RIK | RIKEN cDNA 1810009M01 gene | Uterus | 2.21 |
| 92616_at | UBE1X | ubiquitin-activating enzyme E1, Chr X | Uterus | 2.21 |
| 93046_at | NUP50 | nucleoprotein 50 | Uterus | 2.2 |
| 98608_at | D6ERTD109E | DNA segment, Chr 6, ERATO Doi 109, expressed | Uterus | 2.19 |
| 92909_at | PGF | placental growth factor | Uterus | 2.19 |
| 101009_at | KRT2-8 | keratin complex 2, basic, gene 8 | Uterus | 2.19 |
| 100154_at | D17WSU91E | DNA segment, Chr 17, Wayne State University 91, expressed | Uterus | 2.19 |
| 96658_at | UNK_AI841906 | Cluster Incl AI841906: UI-M-AO0-acd-e-10-0-UI.s1 *Mus musculus* cDNA, 3' end/clone = UI-M-AO0-acd-e-10-0-UI/ clone_end3'/gb = AI841906/gi = 5476119/ug = Mm.27344/ len = 417/STRA = for | Uterus | 2.18 |
| 94018_at | UBL3 | ubiquitin-like 3 | Uterus | 2.18 |
| 98129_at | ESET | ERG-associated protein | Uterus | 2.17 |
| 98498_at | CASP7 | caspase 7 | Uterus | 2.17 |
| 94247_at | ETS2 | E26 avian leukemia oncogene 2, 3' domain | Uterus | 2.16 |

TABLE III-continued

Genes Regulated By Estrogen in the Uterus

| Mousedata.Qualifier | Pub_Name | Gene Name | Tissue | Mean WT E2 Fold Change |
|---|---|---|---|---|
| 100084_at | VIL2 | villin 2 | Uterus | 2.15 |
| 93093_at | MCL1 | myeloid cell leukemia sequence 1 | Uterus | 2.15 |
| 95109_at | UNK_AW121447 | ESTs, Weakly similar to SIK similar protein [*M. musculus*] | Uterus | 2.15 |
| 101963_at | CTSL | cathepsin L | Uterus | 2.14 |
| 102821_s_at | RASL2-9 | RAS-like, family 2, locus 9 | Uterus | 2.13 |
| 97240_g_at | D19ERTD721E | DNA segment, Chr 19, ERATO Doi 721, expressed | Uterus | 2.13 |
| 94257_at | ARHGDIB | rho, GDP dissociation inhibitor (GDI) beta | Uterus | 2.12 |
| 101543_f_at | TUBA6 | tubulin alpha 6 | Uterus | 2.11 |
| 100720_at | PABPC1 | poly A binding protein, cytoplasmic 1 | Uterus | 2.11 |
| 100566_at | IGFBP5 | insulin-like growth factor binding protein 5 | Uterus | 2.1 |
| 95647_f_at | UNK_AI465845 | ESTs, Moderately similar to unnamed protein product [*H. sapiens*] | Uterus | 2.1 |
| 94899_at | RHOIP3-PENDING | Rho interacting protein 3 | Uterus | 2.09 |
| 104716_at | RBP1 | retinal binding protein 1, cellular | Uterus | 2.08 |
| 96338_at | UNK_AW125059 | ESTs, Weakly similar to A53770 growth factor-responsive protein, vascular smooth muscle - rat□ [*R. norvegicus*] | Uterus | 2.08 |
| 103350_at | PSMD7 | proteasome (prosome, macropain) 26S subunit, non-ATPase, 7 | Uterus | 2.08 |
| 94040_at | ERH | enhancer of rudimentary homolog (*Drosophila*) | Uterus | 2.08 |
| 104041_at | UNK_AW122255 | ESTs, Moderately similar to T00076 hypothetical protein KIAA0462 - human [*H. sapiens*] | Uterus | 2.07 |
| 96834_at | UNK_AI843586 | ESTs, Highly similar to PRE-MRNA SPLICING FACTOR SF2, P33 SUBUNIT [*Homo sapiens*] | Uterus | 2.07 |
| 103955_at | UNK_AW050325 | ESTs, Highly similar to LAMBDA-CRYSTALLIN [*Oryctolagus cuniculus*] | Uterus | 2.07 |
| 93997_at | IFRG15 | interferon alpha responsive protein (15 kDa) | Uterus | 2.06 |
| 99985_at | TXNRD1 | thioredoxin reductase 1 | Uterus | 2.06 |
| 104125_at | HA1R-PENDING | Hoxa1 regulated gene | Uterus | 2.05 |
| 92816_r_at | EIF4A1 | eukaryotic translation initiation factor 4A1 | Uterus | 2.05 |
| 98993_at | PPP2R5C | protein phosphatase 2, regulatory subunit B (B56), gamma isoform | Uterus | 2.04 |
| 98113_at | PSMB1 | proteasome (prosome, macropain) subunit, beta type 1 | Uterus | 2.04 |
| 99566_at | TPI | triosephosphate isomerase | Uterus | 2.04 |
| 101107_at | CALU | calumenin | Uterus | 2.04 |
| 99599_s_at | UNK_AW210320 | ESTs, Weakly similar to AF121217_1 pro-alpha-2(I) collagen [*R. norvegicus*] | Uterus | 2.03 |
| 96724_r_at | D17H6S56E-5 | DNA segment, Chr 17, human D6S56E 5 | Uterus | 2.03 |
| 97994_at | TCF7 | transcription factor 7, T-cell specific | Uterus | 2.03 |
| 95102_at | UNK_AW123754 | ESTs, Moderately similar to APB3_RAT AMYLOID BETA A4 PRECURSOR PROTEIN-BINDING FAMILY A MEMBER 3 [*R. norvegicus*] | Uterus | 2.02 |
| 94454_at | PRTB | proline rich protein expressed in brain | Uterus | 2.02 |
| 103059_at | FXYD3 | FXYD domain-containing ion transport regulator 3 | Uterus | 2.02 |
| 93037_i_at | ANXA1 | annexin A1 | Uterus | 2.01 |
| 104385_i_at | UNK_AI843901 | Cluster Incl AI843901: UI-M-AK1-aeu-g-04-0-UI.s1 *Mus musculus* cDNA, 3' end/clone = UI-M-AK1-aeu-g-04-0-UI/ clone_end = 3'/gb = AI843901/gi = 5478114/ug = Mm.227/ len = 300/STRA = for | Uterus | 2.01 |
| 93490_at | UNK_AI841771 | ESTs, Weakly similar to contains similarity to *Saccharomyces cerevisiae* MAF1 protein [*C. elegans*] | Uterus | 2 |
| 95406_at | UNK_AW125347 | Cluster Incl AW125347: UI-M-BH2.1-apy-h-03-0-UI.s1 *Mus musculus* cDNA, 3' end/clone = UI-M-BH2.1-apy-h-03-0-UI/ clone_end = 3'/gb = AW125347/gi = 6100877/ug = Mm.24219/ len = 331/STRA = for | Uterus | 1.99 |
| REPRESSIONS | | | | |
| 93594_r_at | EMP3 | epithelial membrane protein 3 | Uterus | 0.55 |
| 104235_at | VAMP2 | vesicle-associated membrane protein 2 | Uterus | 0.54 |
| 97317_at | ENPP2 | ectonucleotide pyrophosphatase/phosphodiesterase 2 | Uterus | 0.52 |
| 94813_at | GAS1 | growth arrest specific 1 | Uterus | 0.51 |
| 95133_at | ASNS | asparagine synthetase | Uterus | 0.48 |
| 103353_f_at | CYP4B1 | cytochrome P450, subfamily IV B, polypeptide 1 | Uterus | 0.46 |
| 99577_at | KITL | kit ligand | Uterus | 0.45 |
| 102395_at | PMP22 | peripheral myelin protein, 22 kDa | Uterus | 0.44 |
| 93013_at | IDB2 | inhibitor of DNA binding 2 | Uterus | 0.44 |
| 101152_at | HTR5A | 5-hydroxytryptamine (serotonin) receptor 5A | Uterus | 0.41 |
| 92589_at | UNK_AI846545 | ESTs, Highly similar to SERB_HUMAN L-3-PHOSPHOSERINE PHOSPHATASE [*H. sapiens*] | Uterus | 0.4 |
| 104217_at | UNK_AW045753 | Cluster Incl AW045753: UI-M-BH1-akt-a-10-0-UI.s1 *Mus musculus* cDNA, 3' end/clone = UI-M-BH1-akt-a-10-0-UI/ clone_end = 3'/gb = AW045753/gi = 5906282/ug = Mm.27893/ len = 407/STRA = rev | Uterus | 0.39 |
| 93503_at | SDF5 | stromal cell derived factor 5 | Uterus | 0.38 |
| 96672_at | UNK_AW123564 | ESTs, Weakly similar to S36166 paired box transcription factor Pax-6 - rat [*R. norvegicus*] | Uterus | 0.38 |

TABLE III-continued

Genes Regulated By Estrogen in the Uterus

| Mousedata.Qualifier | Pub_Name | Gene Name | Tissue | Mean WT E2 Fold Change |
|---|---|---|---|---|
| 93543_f_at | GSTM1 | glutathione S-transferase, mu 1 | Uterus | 0.36 |
| 93836_at | BNIP3 | BCL2/adenovirus E1B 19 kDa-interacting protein 1, NIP3 | Uterus | 0.35 |
| 98575_at | FASN | fatty acid synthase | Uterus | 0.33 |
| 99671_at | ADN | adipsin | Uterus | 0.33 |
| 101990_at | LDH2 | lactate dehydrogenase 2, B chain | Uterus | 0.3 |
| 98588_at | FAH | fumarylacetoacetate hydrolase | Uterus | 0.3 |
| 92592_at | GDC1 | glycerol phosphate dehydrogenase 1, cytoplasmic adult | Uterus | 0.3 |
| 104313_at | UNK_AI842432 | ESTs, Moderately similar to PHOSPHOGLUCOMUTASE [*Rattus norvegicus*] | Uterus | 0.3 |
| 102094_f_at | GSTM1 | glutathione S-transferase, mu 1 | Uterus | 0.3 |
| 92202_g_at | UNK_AI553024 | ESTs, Highly similar to 2118318A promyelocyte leukemia Zn finger protein [*M. musculus*] | Uterus | 0.29 |
| 94056_at | SCD1 | stearoyl-Coenzyme A desaturase 1 | Uterus | 0.27 |
| 95731_at | UNK_AI843106 | ESTs, Highly similar to p53 regulated PA26-T2 nuclear protein [*H. sapiens*] | Uterus | 0.27 |
| 97844_at | RGS2 | regulator of G-protein signaling 2 | Uterus | 0.26 |
| 94516_f_at | PENK2 | preproenkephalin 2 | Uterus | 0.19 |
| 95082_at | IGFBP3 | insulin-like growth factor binding protein 3 | Uterus | 0.19 |
| 94057_g_at | SCD1 | stearoyl-Coenzyme A desaturase 1 | Uterus | 0.19 |
| 101560_at | EMB | embigin | Uterus | 0.18 |
| 93996_at | CYP2E1 | cytochrome P450, 2e1, ethanol inducible | Uterus | 0.18 |
| 101991_at | FMO1 | flavin containing monooxygenase 1 | Uterus | 0.17 |
| 92877_at | TGFBI | transforming growth factor, beta induced, 68 kDa | Uterus | 0.16 |
| 97402_at | TEMT | thioether S-methyltransferase | Uterus | 0.15 |
| 100567_at | FABP4 | fatty acid binding protein 4, adipocyte | Uterus | 0.14 |
| 99104_at | ACRP30 | adipocyte complement related protein of 30 kDa | Uterus | 0.13 |

TABLE IV

Genes Regulated By Estrogen in the Kidney

| Potential ERa regs | Potential ERb regs | Fragment Name | Exemplar Seq: A | Unigene | Known Gene.Name | Approx Ave Fold | Study 1 WT Veh Expr (/evansm/Kidney, mouse/Study 1, U74v2/WT Vehicle kidney (81010)) | Study 1 E2 Expr (/evansm/Kidney, mouse/Study 1, U74v2/WT E2 kidney (81036)) | Study 1 ERbKO Veh Expr (/evansm/Kidney, mouse/Study 1, U74v2/KO Vehicle kidney (81025)) |
|---|---|---|---|---|---|---|---|---|---|
| | | | | | INDUCTIONS | | | | |
| x | | 100060_l_at | M13500 | | kallikrein 8 | 15.78 | 5 | 39 | 2 |
| x | | 100061_f_at | M13500 | | kallikrein 8 | 83.25 | 6 | 341 | 3 |
| x | | 95775_f_at | V00829 | | kallikrein 1 | 61.00 | 7 | 370 | 8 |
| x | | 104495_f_at | Y00500 | Mm.30375 | kallikrein 5 | 52.59 | 5 | 115 | 2 |
| x | | 94716_f_at | M17962 | Mm.200410 | kallikrein 9 | 44.67 | 16 | 380 | 8 |
| x | | 100422_f_at | AJ237939 | Mm.4697 | signal transducer and activator of transcription 5A | 39.21 | 5 | 151 | 2 |
| x | | 100423_f_at | AJ237939 | Mm.4697 | signal transducer and activator of transcription 5A | 3.80 | 41 | 96 | 13 |
| x | | 101289_f_at | M17979 | | | 28.73 | 18 | 305 | 11 |
| x | | 100681_f_at | V00829 | | | 25.24 | 8 | 123 | 6 |
| x | | 94773_at | X01801 | | nerve growth factor, alpha | 17.80 | 5 | 53 | 2 |
| x | | 104497_f_at | X03994 | Mm.5193 | kallikrein 8 | 17.44 | 6 | 53 | 3 |
| x | | 168876_f_at | AV044014 | Mm.143833 | kallikrein 21 | 17.40 | 6 | 75 | 4 |
| x | | 102693_f_at | J00389 | Mm.143842 | kallikrein 13, kallikrein 26 | 17.24 | 5 | 86 | 6 |
| x | | 100719_f_at | J03677 | Mm.19214 | kallikrein 16 | 14.45 | 13 | 119 | 7 |
| x | | 114903_at | AI447633 | Mm.26357 | | 13.56 | 10 | 96 | 7 |
| x | | 139531_at | AW120795 | Mm.45188 | | 12.37 | 2 | 40 | 2 |
| x | | 101870_at | V00793 | | | 7.39 | 5 | 21 | 2 |

TABLE IV-continued

Genes Regulated By Estrogen in the Kidney

| | | | | | | | | |
|---|---|---|---|---|---|---|---|---|
| x | 104221_at | AB017189 | Mm.27943 | solute carrier family 7 (cationic amino acid transporter, y+ system), member 5 | 6.99 | 8 | 61 | 9 |
| x | 95905_at | AI118078 | Mm.24361 | | 6.67 | 15 | 83 | 7 |
| x | 111046_r_at | AI957367 | Mm.26838 | 17b dehydrogenase A homolog | 6.34 | 2 | 17 | 2 |
| x | 133672_at | AI451032 | Mm.32389 | | 5.91 | 2 | 11 | 2 |
| x | 117208_at | AI838208 | Mm.41330 | RIKEN cDNA 1110003O08 gene | 5.86 | 3 | 37 | 3 |
| x | 96591_at | U24703 | Mm.3057 | reelin | 5.28 | 5 | 43 | 3 |
| x | 103048_at | M12731 | Mm.16469 | neuroblastoma myc-related oncogene 1 | 4.76 | 6 | 39 | 2 |
| x | 165248_f_at | AV035328 | Mm.37203 | placental lactogen 2 | 4.50 | 6 | 38 | 6 |
| x | 92232_at | U88328 | Mm.3468 | cytokine inducible SH-2 containing protein 3 | 4.37 | 5 | 45 | 6 |
| x | 164520_f_at | AV302474 | Mm.25743 | Tmprss2 Transmembrane protease, serine 2 | 4.26 | 1 | 6 | 1 |
| x | 99632_at | U83902 | Mm.43444 | MAD2 (mitotic arrest deficient, homolog)-like 1 (yeast) | 3.99 | 9 | 27 | 4 |
| x | 116273_at | AW123862 | Mm.31953 | | 3.91 | 5 | 7 | 5 |
| x | 131226_at | AI842542 | Mm.23157 | | 3.60 | 2 | 8 | 2 |
| x | 104550_at | AW123273 | Mm.23710 | ?CYP2S1 Cytochrome P450 | 3.54 | 7 | 22 | 5 |
| x | 105737_at | AI851277 | Mm.39735 | | 3.38 | 2 | 8 | 1 |
| x | 100407_at | L38580 | Mm.4655 | galanin | 3.38 | 24 | 98 | 13 |
| x | 97353_at | AI837497 | Mm.29629 | AF9Q34 NGAP-like protein | 3.35 | 13 | 29 | 4 |
| x | 163941_at | AI646761 | Mm.202077 | RIKEN cDNA 1110018J23 gene | 3.32 | 31 | 71 | 15 |
| x | 162976_at | AI838662 | Mm.198767 | RIKEN cDNA 2700007F12 gene | 3.30 | 3 | 10 | 2 |
| x | 101979_at | AF055638 | Mm.9653 | growth arrest and DNA-damage-inducible 45 gamma | 3.26 | 8 | 42 | 8 |
| x | 93374_at | AI836349 | Mm.143762 | junctophilin 3 | 3.23 | 25 | 65 | 6 |
| x | 107629_at | AW048768 | Mm.27667 | | 3.17 | 14 | 34 | 13 |
| x | 112320_at | AI852394 | Mm.37753 | | 3.15 | 14 | 30 | 8 |
| x | 133278_at | AI452199 | Mm.31771 | | 3.11 | 3 | 8 | 2 |
| x | 95109_at | AW121447 | Mm.29363 | NOL5A Nucleolar protein 5A | 3.07 | 33 | 91 | 21 |
| x | 133815_at | AU042854 | Mm.26783 | | 3.01 | 3 | 9 | 2 |
| x | 114394_at | AW121080 | Mm.32795 | | 2.96 | 4 | 17 | 7 |
| x | 167969_at | AA982630 | Mm.87051 | Weakly similar to high mobility group 1 protein | 2.92 | 5 | 16 | 2 |
| x | 100938_at | M31658 | Mm.144157 | growth hormone releasing hormone | 2.88 | 9 | 41 | 7 |
| x | 97825_at | AI854029 | Mm.28209 | p53 apoptosis effector related to Pmp22 | 2.85 | 10 | 33 | 3 |
| x | 136270_at | AI854101 | Mm.40241 | Highly similar to CRFB MOUSE CORTICOTROPIN-RELEASING FACTOR BINDING PROTEIN PRECURSOR | 2.84 | 3 | 12 | 2 |
| x | 134303_at | AI553493 | Mm.35319 | | 2.81 | 3 | 11 | 3 |
| x | 107993_at | AI847249 | Mm.27680 | | 2.81 | 2 | 9 | 2 |
| x | 104776_at | AA600617 | Mm.33238 | | 2.70 | 1 | 4 | 1 |
| x | 171390_i_at | AV299689 | Mm.21070 | | 2.66 | 2 | 3 | 2 |
| x | 103556_at | AI840158 | Mm.19081 | angiopoletin-like 2 | 2.60 | 8 | 24 | 7 |
| x | 109176_at | AI846059 | Mm.29219 | RAI17 Retinoic acid Induced 17 | 2.58 | 47 | 79 | 33 |

TABLE IV-continued

Genes Regulated By Estrogen in the Kidney

| | | | | | | | | |
|---|---|---|---|---|---|---|---|---|
| x | 163186_at | AI852882 | Mm.23230 | RIKEN cDNA 2610510B01 gene | 2.57 | 20 | 61 | 25 |
| x | 170686_f_at | AV362687 | Mm.89845 | | 2.52 | 22 | 58 | 27 |
| x | 164051_at | AV359458 | Mm.17850 | | 2.46 | 87 | 195 | 90 |
| x | 108749_at | AA611885 | Mm.23047 | | 2.41 | 16 | 34 | 12 |
| x | 96629_at | X04097 | Mm.27194 | similar to TESTOSTERONE-REGULATED RP2 PROTEIN | 2.32 | 22 | 55 | 11 |
| x | 110767_r_at | AA959550 | Mm.31540 | vascular endothelial growth factor | 2.31 | 13 | 37 | 9 |
| x | 165772_at | AI851899 | Mm.41409 | RIKEN cDNA 0610039J01 gene | 2.24 | 17 | 29 | 13 |
| x | 99552_at | U79550 | Mm.4272 | slug, chicken homolog | 2.23 | 7 | 19 | 6 |
| x | 98437_at | U83720 | Mm.34405 | caspase 3, apoptosis related cysteine protease | 2.22 | 21 | 39 | 11 |
| x | 165710_at | AA815844 | | sodium channel, nonvoltage-gated 1 gamma | 2.22 | 3 | 9 | 2 |
| x | 110591_at | AA270831 | Mm.2454 | SH3 domain protien D19 | 2.21 | 11 | 23 | 10 |
| x | 113125_at | AI851671 | Mm.34064 | signal transducer and activator of transcription 5B | 2.20 | 11 | 31 | 11 |
| x | 110850_at | AA959574 | Mm.74711 | NRIP1 Nuclear receptor interacting protein 1, RIP140 | 2.18 | 28 | 76 | 25 |
| x | 103739_at | AW230977 | Mm.24411 | RIKEN cDNA 1110017N23 gene | 2.16 | 10 | 33 | 10 |
| x | 165032_i_at | AV365688 | Mm.200980 | RIKEN cDNA 4933429H19 gene | 2.15 | 20 | 42 | 12 |
| x | 166843_at | AI851523 | Mm.200318 | | 2.12 | 149 | 174 | 105 |
| x | 166021_at | AI481830 | Mm.49448 | | 2.09 | 7 | 12 | 5 |
| x | 100440_f_at | U76758 | Mm.4789 | ankyrin 1, erythroid | 2.08 | 60 | 119 | 19 |
| x | 163370_at | AI591488 | Mm.31024 | Osbpl3 Oxysterol binding protien-like 3 | 2.08 | 6 | 10 | 7 |
| x | 96215_f_at | AI53421 | Mm.218360 | | 2.08 | 92 | 206 | 32 |
| x | 165866_f_at | AV291803 | Mm.70127 | ribosomal protein L12 | 2.08 | 22 | 40 | 17 |
| x | 98628_f_at | AF003695 | Mm.3879 | hypoxia inducible factor 1, alpha subunit | 1.97 | 129 | 288 | 68 |
| | | | | REPRESSIONS | | | | |
| x | 104880_at | AI843154 | Mm.33730 | | 0.50 | 10 | 2 | 11 |
| x | 129147_r_at | AI931796 | Mm.214530 | similar to TYROSINE-PROTEIN KINASE RECEPTOR TIE-1 PRECURSOR | 0.50 | 20 | 6 | 15 |
| x | 102788_s_at | U70132 | Mm.1385 | paired-like homeodomain transcription factor 2 | 0.49 | 83 | 23 | 35 |
| x | 166849_at | AI853080 | Mm.40718 | | 0.49 | 40 | 16 | 29 |
| x | 165678_i_at | AI482191 | Mm.33178 | | 0.49 | 23 | 11 | 15 |
| x | 106195_at | AI851948 | Mm.22808 | | 0.48 | 17 | 8 | 15 |
| x | 131149_at | AW214502 | Mm.27650 | RIKEN cDNA 5033417D07 gene | 0.48 | 17 | 7 | 16 |
| x | 162645_at | AI851427 | Mm.25594 | protein kinase, cAMP dependent regulatory, type II beta | 0.48 | 20 | 11 | 15 |
| x | 100539_at | AI841279 | Mm.157073 | ?HBACH Cytosolic acyl coenzyme A thioester hydrolase | 0.47 | 38 | 16 | 22 |

TABLE IV-continued

Genes Regulated By Estrogen in the Kidney

| | Probe | Accession | Mm. | Gene | Val | V1 | V2 | V3 |
|---|---|---|---|---|---|---|---|---|
| x | 169068_i_at | AV206066 | Mm.59239 | RIKEN cDNA 4930434J08 gene | 0.46 | 6 | 2 | 8 |
| x | 99127_at | X61506 | Mm.4098 | spinocerebellar ataxia 10 homolog (human) | 0.45 | 136 | 66 | 52 |
| x | 108265_at | AW120464 | Mm.54158 | | 0.45 | 32 | 12 | 16 |
| x | 137525_at | AI098139 | Mm.38027 | | 0.44 | 9 | 4 | 13 |
| x | 167023_f_at | AV016619 | Mm.2608 | biglycan | 0.44 | 15 | 3 | 6 |
| x | 101738_at | U25145 | Mm.57061 | tutetnizing hormone beta | 0.43 | 1120 | 578 | 606 |
| x | 104477_at | AW047643 | Mm.29940 | | 0.43 | 23 | 15 | 18 |
| x | 93104_at | Z16410 | | B-cell translocation gene 1, anti-proliferative | 0.42 | 27 | 14 | 18 |
| x | 162969_at | AW123298 | Mm.41716 | Edil3 EGF-like repeats and discordin I-like domains 3 | 0.41 | 55 | 34 | 41 |
| x | 165569_at | AI847273 | Mm.22305 | | 0.41 | 14 | 5 | 16 |
| x | 170896_at | AV066592 | Mm.34232 | Immune associated nucleotide 4 | 0.40 | 9 | 3 | 14 |
| x | 103729_at | M36775 | Mm.243 | laminin, alpha 1 | 0.40 | 24 | 17 | 26 |
| x | 132403_at | AI788603 | Mm.169241 | similar to TSC1_RAT HAMARTIN (TUBEROUS SCLEROSIS 1 PROTEIN HOMOLOG) | 0.40 | 54 | 19 | 47 |
| x | 97519_at | X13986 | Mm.321 | secreted phosphoprotein 1 | 0.39 | 338 | 178 | 212 |
| x | 98055_at | AW121500 | Mm.34330 | bladder cancer associated protein homolog (human) | 0.39 | 33 | 14 | 19 |
| x | 163224_at | AI843147 | Mm.24577 | IGSF1 Immunoglobulin superfamily, member 1 | 0.38 | 51 | 27 | 33 |
| x | 95559_at | AI838836 | Mm.27768 | RIKEN cDNA 6330403K07 gene | 0.38 | 145 | 74 | 73 |
| x | 99057_at | M12379 | | thymus cell antigen 1, theta | 0.35 | 131 | 57 | 61 |
| x | 133139_at | AW122295 | Mm.41642 | regulator of G-protein signaling 4 | 0.34 | 20 | 4 | 22 |
| x | 162964_at | AI854153 | Mm.41842 | regulator of G-protein signaling 4 | 0.33 | 50 | 11 | 39 |
| x | 97520_s_at | X83569 | Mm.140956 | neuroatin | 0.32 | 523 | 157 | 314 |
| x | 94694_at | M69196 | Mm.1333 | proprotein convertase subtillsin/kexin type 1 | 0.29 | 99 | 27 | 51 |
| x | 108851_at | AW125899 | Mm.66275 | Ras-like protein | 0.27 | 33 | 10 | 33 |
| x | 101737_at | U12932 | Mm.46711 | follicle stimulating hormone beta | 0.16 | 163 | 19 | 87 |

| Potential ERa regs | Study 1 E2 Expr (/evansm/ Kidney, mouse/Study 1, U74v2/KO E2 kidney (81038)) | Study 2 WT Veh Expr (/evansm/Kidney, mouse/Study 2, U74v2/WT kidney vehicle (82406)) | Study 2 Veh Expr (/evansm/ Kidney, mouse/Study 2, U74v2/WT kidney vehicle (82407)) | Study 2 E2 Expr (/evansm/ Kidney, mouse/Study 2, U74v2/WT kidney E2 (82408)) | E2 Expr (/evansm/Kidney, mouse/Study 2, U74v2/WT kidney E2 (82409)) | ERbKO Veh Expr (/evansm/ Kidney, mouse/Study 2, U74v2/ER bKO kidney vehicle (82410)) | Veh Expr (/evansm/ Kidney, mouse/Study 2, U74v2/ER bKO kidney vehicle (82411)) | E2 Expr (/evansm/ Kidney, mouse/Study 2, U74v2/ER bKO kidney E2 (82412)) | E2 |

TABLE IV-continued

Genes Regulated By Estrogen in the Kidney

INDUCTIONS

| | | | | | | | | | |
|---|---|---|---|---|---|---|---|---|---|
| x | 37 | 1 | 2 | 40 | 31 | 2 | 3 | 44 | 37 |
| x | 370 | 5 | 4 | 338 | 201 | 3 | 4 | 359 | 297 |
| x | 333 | 9 | 6 | 345 | 234 | 2 | 4 | 361 | 291 |
| x | 125 | 1 | 2 | 145 | 89 | 2 | 3 | 163 | 130 |
| x | 372 | 10 | 10 | 329 | 230 | 3 | 5 | 369 | 302 |
| x | 70 | 1 | 2 | 104 | 73 | 2 | 3 | 104 | 92 |
| x | 61 | 20 | 14 | 80 | 44 | 15 | 14 | 58 | 72 |
| x | 282 | 15 | 13 | 264 | 178 | 4 | 5 | 295 | 236 |
| x | 122 | 5 | 6 | 142 | 89 | 3 | 3 | 154 | 117 |
| x | 59 | 1 | 2 | 30 | 24 | 2 | 3 | 33 | 42 |
| x | 67 | 2 | 2 | 45 | 26 | 2 | 3 | 56 | 49 |
| x | 96 | 11 | 7 | 76 | 68 | 4 | 2 | 83 | 70 |
| x | 79 | 5 | 4 | 70 | 38 | 2 | 3 | 86 | 66 |
| x | 103 | 6 | 7 | 87 | 50 | 3 | 5 | 95 | 82 |
| x | 94 | 11 | 7 | 92 | 97 | 6 | 4 | 125 | 84 |
| x | 24 | 2 | 2 | 32 | 17 | 4 | 2 | 40 | 22 |
| x | 14 | 1 | 2 | 19 | 13 | 2 | 3 | 24 | 22 |
| x | 47 | 14 | 8 | 64 | 57 | 4 | 9 | 61 | 61 |
| x | 38 | 6 | 4 | 35 | 30 | 4 | 5 | 46 | 33 |
| x | 13 | 3 | 3 | 11 | 9 | 3 | 2 | 12 | 11 |
| x | 16 | 2 | 2 | 15 | 8 | 4 | 2 | 23 | 14 |
| x | 18 | 9 | 4 | 16 | 15 | 9 | 4 | 15 | 26 |
| x | 10 | 3 | 3 | 14 | 7 | 2 | 3 | 14 | 12 |
| x | 9 | 2 | 2 | 9 | 5 | 2 | 3 | 15 | 10 |
| x | 29 | 4 | 7 | 14 | 32 | 8 | 7 | 27 | 17 |
| x | 11 | 6 | 5 | 12 | 13 | 7 | 5 | 21 | 15 |
| x | 8 | 3 | 2 | 7 | 8 | 3 | 3 | 10 | 8 |
| x | 16 | 5 | 5 | 19 | 14 | 3 | 5 | 23 | 19 |
| x | 30 | 5 | 4 | 22 | 18 | 5 | 2 | 16 | 13 |
| x | 11 | 2 | 3 | 11 | 8 | 4 | 2 | 8 | 6 |
| x | 11 | 2 | 3 | 14 | 7 | 3 | 4 | 18 | 10 |
| x | 4 | 2 | 3 | 6 | 3 | 2 | 1 | 8 | 6 |
| x | 42 | 14 | 13 | 41 | 25 | 10 | 11 | 44 | 37 |
| x | 14 | 5 | 6 | 18 | 12 | 4 | 5 | 27 | 16 |
| x | 60 | 18 | 17 | 55 | 41 | 10 | 12 | 65 | 43 |
| x | 8 | 3 | 4 | 9 | 10 | 3 | 2 | 9 | 11 |
| x | 10 | 6 | 4 | 17 | 10 | 4 | 5 | 19 | 18 |
| x | 30 | 7 | 10 | 24 | 19 | 8 | 8 | 26 | 19 |
| x | 38 | 8 | 13 | 31 | 36 | 6 | 9 | 29 | 36 |
| x | 30 | 7 | 7 | 16 | 13 | 4 | 6 | 26 | 22 |
| x | 10 | 3 | 3 | 9 | 11 | 6 | 3 | 4 | 10 |
| x | 69 | 28 | 21 | 74 | 42 | 15 | 20 | 76 | 57 |
| x | 11 | 2 | 2 | 5 | 4 | 5 | 3 | 7 | 8 |
| x | 13 | 5 | 5 | 13 | 9 | 3 | 3 | 11 | 12 |
| x | 7 | 3 | 4 | 8 | 8 | 8 | 4 | 18 | 17 |
| x | 19 | 8 | 8 | 14 | 13 | 4 | 6 | 11 | 15 |
| x | 12 | 6 | 4 | 9 | 4 | 3 | 5 | 11 | 10 |
| x | 7 | 2 | 2 | 7 | 1 | 4 | 2 | 7 | 4 |
| x | 14 | 5 | 6 | 9 | 10 | 5 | 7 | 10 | 9 |
| x | 7 | 3 | 3 | 4 | 4 | 3 | 2 | 5 | 2 |
| x | 4 | 2 | 2 | 6 | 2 | 3 | 1 | 4 | 5 |
| x | 11 | 2 | 2 | 9 | 6 | 4 | 2 | 4 | 3 |
| x | 14 | 3 | 2 | 7 | 5 | 3 | 4 | 10 | 11 |
| x | 104 | 33 | 29 | 75 | 52 | 15 | 22 | 70 | 61 |
| x | 50 | 23 | 19 | 42 | 30 | 13 | 16 | 50 | 53 |
| x | 66 | 11 | 15 | 34 | 23 | 10 | 14 | 38 | 32 |
| x | 201 | 61 | 62 | 132 | 117 | 36 | 52 | 152 | 140 |
| x | 25 | 7 | 8 | 16 | 13 | 5 | 7 | 23 | 21 |
| x | 24 | 20 | 19 | 31 | 23 | 6 | 12 | 33 | 26 |
| x | 17 | 4 | 4 | 11 | 4 | 4 | 4 | 11 | 9 |
| x | 26 | 11 | 11 | 21 | 12 | 6 | 6 | 25 | 18 |
| x | 15 | 8 | 7 | 11 | 6 | 4 | 5 | 13 | 12 |
| x | 22 | 10 | 9 | 22 | 18 | 6 | 11 | 27 | 23 |
| x | 6 | 3 | 3 | 5 | 3 | 4 | 3 | 6 | 5 |
| x | 24 | 8 | 7 | 14 | 11 | 7 | 7 | 22 | 16 |
| x | 13 | 10 | 8 | 11 | 9 | 6 | 3 | 13 | 19 |
| x | 47 | 22 | 19 | 32 | 23 | 13 | 18 | 47 | 43 |
| x | 14 | 7 | 6 | 11 | 6 | 3 | 7 | 16 | 13 |
| x | 30 | 12 | 5 | 17 | 7 | 9 | 6 | 24 | 15 |
| x | 265 | 83 | 80 | 175 | 174 | 85 | 49 | 181 | 174 |
| x | 14 | 7 | 4 | 11 | 7 | 5 | 4 | 11 | 10 |
| x | 53 | 20 | 25 | 41 | 39 | 30 | 23 | 47 | 47 |
| x | 13 | 5 | 4 | 10 | 8 | 4 | 4 | 14 | 9 |
| x | 101 | 89 | 80 | 117 | 87 | 46 | 50 | 101 | 66 |

TABLE IV-continued

Genes Regulated By Estrogen in the Kidney

| | | | | | | | | | |
|---|---|---|---|---|---|---|---|---|---|
| x | 35 | 20 | 17 | 33 | 25 | 7 | 12 | 31 | 24 |
| x | 136 | 88 | 76 | 143 | 100 | 56 | 68 | 153 | 114 |
| | | | | | REPRESSIONS | | | | |
| x | 9 | 26 | 13 | 9 | 6 | 18 | 5 | 9 | 5 |
| x | 7 | 12 | 7 | 5 | 4 | 6 | 6 | 5 | 4 |
| x | 28 | 41 | 28 | 15 | 7 | 18 | 27 | 15 | 10 |
| x | 17 | 22 | 15 | 8 | 4 | 11 | 13 | 9 | 7 |
| x | 8 | 15 | 14 | 6 | 4 | 10 | 12 | 7 | 6 |
| x | 7 | 12 | 9 | 5 | 4 | 7 | 8 | 5 | 4 |
| x | 7 | 14 | 13 | 6 | 6 | 10 | 11 | 6 | 7 |
| x | 8 | 14 | 12 | 4 | 2 | 10 | 11 | 6 | 6 |
| x | 13 | 22 | 19 | 5 | 3 | 7 | 19 | 8 | 10 |
| x | 4 | 3 | 3 | 2 | 1 | 4 | 6 | 2 | 2 |
| x | 28 | 53 | 43 | 16 | 7 | 29 | 60 | 21 | 19 |
| x | 8 | 24 | 27 | 11 | 7 | 17 | 20 | 12 | 7 |
| x | 6 | 9 | 10 | 3 | 3 | 7 | 8 | 3 | 4 |
| x | 5 | 5 | 5 | 2 | 1 | 4 | 6 | 3 | 3 |
| x | 262 | 525 | 470 | 180 | 125 | 257 | 446 | 176 | 185 |
| x | 7 | 19 | 14 | 4 | 4 | 10 | 15 | 6 | 6 |
| x | 7 | 22 | 18 | 7 | 4 | 13 | 21 | 8 | 7 |
| x | 22 | 48 | 42 | 8 | 4 | 25 | 36 | 11 | 11 |
| x | 6 | 15 | 15 | 6 | 4 | 7 | 13 | 5 | 5 |
| x | 5 | 10 | 6 | 4 | 2 | 7 | 9 | 4 | 4 |
| x | 7 | 25 | 11 | 6 | 3 | 14 | 18 | 8 | 4 |
| x | 19 | 35 | 27 | 14 | 12 | 23 | 23 | 12 | 8 |
| x | 84 | 255 | 198 | 76 | 46 | 184 | 198 | 77 | 59 |
| x | 9 | 25 | 15 | 5 | 4 | 9 | 19 | 5 | 6 |
| x | 17 | 31 | 26 | 6 | 5 | 18 | 26 | 4 | 7 |
| x | 27 | 86 | 71 | 23 | 12 | 42 | 64 | 25 | 19 |
| x | 25 | 100 | 83 | 18 | 17 | 38 | 71 | 21 | 19 |
| x | 6 | 12 | 8 | 4 | 2 | 6 | 8 | 4 | 4 |
| x | 19 | 35 | 41 | 12 | 8 | 22 | 28 | 9 | 8 |
| x | 133 | 381 | 280 | 87 | 37 | 210 | 322 | 102 | 101 |
| x | 19 | 62 | 52 | 11 | 9 | 24 | 47 | 12 | 12 |
| x | 6 | 24 | 26 | 8 | 6 | 38 | 14 | 8 | 10 |
| x | 17 | 107 | 34 | 17 | 3 | 34 | 58 | 10 | 5 |

LIST OF REFERENCES

1. Grodstein, F., Manson, J. E., Colditz, G A., Willett, W. C., Speizer, F. E. & Stampfer, M. J. (2000) Annals of Internal Medicine 133, 933-41.
2. Barrett-Connor, E., Slone, S., Greendale, G., Kritz-Silverstein, D., Espeland, M., Johnson, S. R., Waclawiw, M. & Fineberg, S. E. (1997) Maturitas 27, 261-74.
3. Godsland, I. F. (2001) Fertility & Sterility 75, 898-915.
4. Nanda, K., Bastian, L. A., Hasselblad, V. & Simel, D. L. (1999) Obstetrics & Gynecology 93, 880-8.
5. Kawas, C., Resnick, S., Morrison, A., Brookmeyer, R., Corrada, M., Zonderman, A., Bacal, C., Lingle, D. D. & Metter, E. (1997) Neurology 48, 1517-21.
6. Worzala, K., Hiller, R., Sperduto, R. D., Mutalik, K., Murabito, J. M., Moskowitz, M., D'Agostino, R. B. & Wilson, P. W. (2001) Archives of Internal Medicine 161, 1448-54.
7. Kuiper, & G, Carlsson, B., Grandien, K., Enmark, E., Haggblad, J., Nilsson, S. & Gustafsson, J. A. (1997) Endocrinology 138, 863-70.
8. Hill, A. A., Hunter, C. P., Tsung, B. T., Tucker-Kellogg, G & Brown, E. L. (2000) Science 290, 809-12.
9. Shughrue, P., Scrimo, P., Lane, M., Askew, R. & Merchenthaler, I. (1997) Endocrinology 138, 5649-52.
10. Evans, M. J., Eckert, A., Lai, K., Adelman, S. J. & Hamish, D. C. (2001) Circulation Research 89, 823-830.
11. Kraichely, D. M., Sun, J., Katzenellenbogen, J. A. & Katzenellenbogen, B. S. (2000) Endocrinology 141, 3534-45.
12. Lubahn, D. B., Moyer, J. S., Golding, T. S., Couse, J. F., Korach, K. S. & Smithies, O. (1993) Proceedings of the National Academy of Sciences of the United States of America 90, 11162-6.
13. Pendaries, C., Darblade, B., Rochaix, P., Krust, A., Chambon, P., Korach, K. S., Bayard, F. & Arnal, J. F. (2002) Proceedings of the National Academy of Sciences of the United States of America 99, 2205-2210.
14. Couse, J. F., Curtis, S. W., Washburn, T. F., Lindzey, J., Golding, T. S., Lubahn, D. B., Smithies, O. & Korach, K. S. (1995) Molecular Endocrinology 9, 1441-54.
15. Berry, M., Metzger, D. & Chambon, R (1990) EMBO Journal 9, 2811-8.
16. Hall, J. M. & McDonnell, D. P. (1999) Endocrinology 140, 5566-78.
17. Weihua, Z., Saji, S., Makinen, S., Cheng, G., Jensen, E. V., Waamer, M. & Gustafsson, J. A. (2000) Proceedings of the National Academy of Sciences of the United States of America 97, 5936-41.
18. Trogan, E., Choudhury, R. P., Dansky, H. M., Rong, J. X., Breslow, J. L. & Fisher, E. A. (2002) Proceedings of the National Academy of Sciences of the United States of America 99, 2234-2239.
19. Evans, M. J., Lai, K., Shaw, L. J., Harnish, D. C. & Chadwick, C. C. (2002) Endocrinology, In press.
20. McIntire, J. J., Umetsu, S. E., Akbari, O., Potter, M., Kuchroo, V. K., Barsh, G. S., Freeman, Q J., Umetsu, D. T. & DeKruyff, R. H. (2001) Nature Immunology 2, 1109-16.

21. Ichimura, T., Bonventre, J. V., Bailly, V., Wei, H., Hession, C. A., Cate, R. L. & Sanicola, M. (1998) Journal of Biological Chemistry 273, 4135-42.
22. Davidoff, M., Caffier, H. & Schiebler, T. H. (1980) Histochemistry 69, 39-48.
23. Aitken, J. M., Lindsay, R. & Hart, D. M. (1974) Clinical Science-& Molecular Medicine 47, 179-87.
24. Pirani, B. B., Campbell, D. M. & MacGillivray, I. (1973) Journal of Obstetrics & Gynaecology of the British Commonwealth 80, 884-7.
25. Stachenfeld, N. S., DiPietro, L., Palter, S. F. & Nadel, E. R. (1998) American Journal of Physiology 274, R187-95.
26. Verlander, J. W., Tran, T M., Zhang, L., Kaplan, M. R. & Hebert, S. C. (1998) Journal of Clinical Investigation 101, 1661-9.
27. Farmer, M. K., Robbins, M. J., Medhurst, A. D., Campbell, D. A., Ellington, K., Duckworth, M., Brown, A. M., Middlemiss, D. N., Price, G. W. & Pangalos, M. N. (2000) Genomics 70, 241-52.
28. Reddy, M. M., Light, M. J. & Quinton, P. M. (1999) Nature 402, 301-4.
29. Fu, G. K., Lin, D., Zhang, M. Y., Bikle, D. D., Shackleton, C. H., Miller, W. L. & Portale, A. A. (1997) Molecular Endocrinology 11, 1961-70.
30. Tanaka, Y., Castillo, L. & DeLuca, H. F. (1976) Proceedings of the National Academy of Sciences of the United States of America 73, 2701-5.
31. McKane, W. R., Khosla, S., Burritt, M. F., Kao, P. C., Wilson, D. M., Ory, S. J. & Riggs, B. L. (1995) Journal of Clinical Endocrinology &-Metabolism 80, 3458-64.
32. Grey, A. B., Stapleton, J. P., Evans, M. C., Tatnell, M. A. & Reid, I. R. (1996) Annals of Internal Medicine 125, 360-8.
33. Johnson, J. A. & Kumar, R. (1994) Seminars in Nephrology 14, 119-28.
34. Hajjar, K. A. (2001) Journal of Clinical Investigation 107, 663-4.
35. Bostom, A. G., Silbershatz, H., Rosenberg, I. H., Selhub, J., D'Agostino, R. B., Wolf, P. A., Jacques, P. F. & Wilson, P W. (1999) Archives of Internal Medicine 159, 1077-80.
36. Walsh, B. W., Paul, S., Wild, R. A., Dean, R. A., Tracy, R. P., Cox, D. A. & Anderson, P. W. (2000) Journal of Clinical Endocrinology & Metabolism 85, 214-8.
37. Libert, F., Parmentier, M., Lefort, A., Dumont, J. E. & Vassart, G (1990) Nucleic Acids Research 18, 1917.
38. Kapas, S. & Clark, A. J. (1995) Biochemical & Biophysical Research Communications 217, 832-8.
39. Gangula, P. R., Zhao, H., Wimalawansa, S. J., Supowit, S. C., DiPette, D. J. & Yallampalli, C. (2001) Biology of Reproduction 64, 1776-83.
40. Cadnapaphomchai, M. A., Briner, V. A. & Schrier, R. W. (2001) in Diseases of the Kidney and Urinary Tract, ed. Schrier, R. W. (Lippincott Williams & Wilkins, Philadelphia), pp. 1459-1487.
41. Safe, S. (2001) Vitamins & Hormones 62, 231-52.
42. Paech, K., Webb, P., Kuiper, G. G., Nilsson, S., Gustafsson, J., Kushner, P. J. & Scanlan, T. S. (1997) Science 277, 1508-10.
43. Naka, T., Fujimoto, M. & Kishimoto, T. (1999) Trends in Biochemical Sciences 24, 394-8.

What is claimed is:

1. An isolated plurality of full-length genes comprising a first group and a second group of full-length genes, wherein said first group comprises the full-length genes NTT73, CYP7B 1 and ABCC3, and wherein said second group comprises the full-length genes BHMT and SAHH.

2. The isolated plurality of full-length genes of claim 1, wherein the first group of genes is differentially expressed at a higher level in kidney cells exposed to estrogen than in said kidney cells without exposure, and wherein each gene in said second group is differentially expressed at a lower level in said kidney cells exposed to estrogen than in said kidney cells without said exposure.

3. The plurality of claim 2, wherein said exposure is in vivo or in vitro.

4. The plurality of claim 3, wherein said higher level and said lower level are assessed using a predetermined statistical significance standard based on measurements of expression levels.

5. The plurality of claim 4, wherein said measurements are obtained using nucleotide arrays or nucleotide filters.

* * * * *